United States Patent
Levin et al.

(10) Patent No.: US 6,294,345 B1
(45) Date of Patent: Sep. 25, 2001

(54) GENES ENCODING PROTEINS ESSENTIAL FOR PLANT GROWTH AND METHODS OF USE

(75) Inventors: Joshua Zvi Levin, Durham; Michael William Bauer, Holly Springs, both of NC (US); Feng Zheng, West Lafayette, IN (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/586,719

(22) Filed: Jun. 5, 2000

Related U.S. Application Data

(60) Provisional application No. 60/287,572, filed on Mar. 27, 2000, provisional application No. 60/228,810, filed on Nov. 22, 1999, provisional application No. 60/240,929, filed on Aug. 20, 1999, provisional application No. 60/198,218, filed on Jul. 27, 1999, and provisional application No. 60/287,571, filed on May 22, 2000.

(51) Int. Cl.$^7$ ...................................................... G01N 33/53
(52) U.S. Cl. .............................. 435/7.1; 435/18; 435/195; 435/232; 530/370
(58) Field of Search .............................. 435/7.1, 18, 195; 435/232; 530/370

(56) References Cited

FOREIGN PATENT DOCUMENTS

| | | |
|---|---|---|
| WO 95/34659 | 12/1995 | (WO) . |
| WO 96/18739 | 6/1996 | (WO) . |
| WO 99/05286 | 2/1999 | (WO) . |
| WO 99/45125 | 10/1999 | (WO) . |

OTHER PUBLICATIONS

Correa et al. Studies on porphobilinogen–deaminase from *Saccharomyces cerevisiae*. Z Naturforsch [C] 1991 Nov.–Dec.;46(11–12):1017–1023 (abstract).*
Lin X et al., "Sequence and Analysis of Chromosome Z of the plant *Arabidopsis thaliana*", Accession No. AC002336 (Jul. 18, 1997).
Partial International Search, PCT/EP 00/05432, 3 pages, Nov. 17, 2000.
Witty et al., Planta 199: 557–564, 1996.
Saw Hoon Lim et al., Plant Molecular Biology 26: 863–872, 1994.
Louie et al., Proteins: Structure, Function and Genetics 25: 48–78, 1996.
Russell M. Jones and Pete M. Jordan, Biochem. J. 299: 895–902, 1994.
Steffen Reinbothe and Christian Reinbothe, Plant Physiol. 111: 1–7, 1996.
Suzuki et al., Annu. Rev. Genet. 31: 61–89, 1997.
Thomas et al., SWISS PROT Accession No. P06983 (1986).
Keng et al., SWISS PROT Accession No. P28789 (1992).
Grandchamp et al., SWISS PROT Accession No. P08397 (1987).
Witty et al., SWISS PROT Accession No. Q43082 (1993).
Bult et al., SWISS PROT Accession No. Q57989 (1996).
Lim et al., SWISS PROT Accession No. Q43316 (1994).
de Boer et al., Plant Molecular Biology 39:1197–1207, 1999.
de Boer et al., Plant Physiol. Biochem., 36(7): 473–486 1998.
Genbank Accession No. AC002560, 1–36 (Jan. 1998).
Grandchamp et al., Enzyme 28: 198–205 (1982).
Heath et al., Journal of Biological Chemistry, 274:16, 11110–11114, 1999.
Heath et al., The Journal of Biological Chemistry, 270:44, 26538–26542, 1995.
Heath et al., The Journal of Biological Chemistry, 273:46, 30316–30320, 1998.
Hoang et al., Journal of Bacteriology, 181:17, 5489–5497, 1999.
Hu, G., Plant Cell, 10: pp. 1095–1105 (1998).
Jones, R.M. and Jordan, P.M., Biochem J., 293: pp. 703–712 (1993).
Kater et al., Plant Molecular Biology, 17: 895–909, 1991.
Kruse et al., Planta 196: 796–803 (1995).
Kruse et al., The EMBO Journal 14(15): 3712–3720 (1995).
Louie et al., Proteins: Structure, Function, and Genetics, 25: 48–78, 1996.
Madsen et al., Plant Molecular Biology 23: 35–43 (1993).
Mock, H.–P. et al., Journal of Biological Chemistry, 274(7): pp. 4231–4238 (1999).
Mock, H.–P. et al., Plant Molecular Biology, 28: pp. 245–256 (1995).
Mou et. al., The Plant Cell, 12:405–417 (2000).
Negrutiu, et al., Mol. Gen Genet, 199:330–337 (1985).
Rafferty et. al., Structure, 3 (9):927–938 (1995).
Ravanel, et al., Plant Molecular Biology 29:875–882 (1995).
Ravanel, et al., Proc. Natl. Acad. Sci. USA, 95:7805–7812 (1998).
Reinbothe, S. and Reinbothe, C., Plant Physiol., 111: pp. 1–7 (1996).
Rounsley et al., The Institute for Genomic Research, Accession No. AAC95176, 1–2, 1998.

(List continued on next page.)

*Primary Examiner*—Nashaat T. Nashed
*Assistant Examiner*—Christian L. Fronda
(74) *Attorney, Agent, or Firm*—J. Timothy Meigs; Edouard G. Lebel; Larry W. Stults

(57) ABSTRACT

The present invention provides plant ENR-A, CBL, UROD, PBGD, and CPPO genes. Also disclosed are the recombinant production of ENR-A, CBL, UROD, PBGD, and CPPO enzymes in heterologous hosts, screening chemicals for herbicidal activity using these recombinantly produced enzymes, and the use of thereby identified herbicidal chemicals to suppress the growth of undesired vegetation. Furthermore, the present invention provides methods for the development of herbicide tolerance in plants, plant tissues, plant seeds, and plant cells using ENR-A, CBL, UROD, PBGD, and CPPO genes of the invention.

8 Claims, No Drawings

OTHER PUBLICATIONS

Russell M. Jones and Pete M. Jordan, Biochem. J., 299: 895–902, 1994.

Saw Hoon Lim, et al., Plant Molecular Biology, 26: 863–872, 1994.

Smith et al., Biochem. J. 292: 503–508 (1993).

Steffen Reinbothe and Christiane Reinbothe, Plant Physiol., 111: 1–7, 1996.

Suzuki et al., Annu. Rev. Genet., 31: 61–89, 1997.

Suzuki, J.Y. et al., Annu. Rev. Genet., 31: pp. 61–89 (1997).

Wagner et al., J. Mol. Biol., 243: 126–127, 1994.

* cited by examiner

SEQUENCE LISTING

<160> NUMBER OF SEQ ID NOS: 34

<210> SEQ ID NO 1
<211> LENGTH: 1173
<212> TYPE: DNA
<213> ORGANISM: Arabidopsis thaliana
<220> FEATURE:
<221> NAME/KEY: CDS
<222> LOCATION: (1)..(1173)

<400> SEQUENCE: 1

```
atg gcg gct aca gca gct tca agc ttg caa att gct aca cga agg ccg      48
Met Ala Ala Thr Ala Ala Ser Ser Leu Gln Ile Ala Thr Arg Arg Pro
 1               5                  10                  15 agc atg tct tcg ccc agc aaa gtt ctt aaa gca gga acc tac att gtt      96
Ser Met Ser Ser Pro Ser Lys Val Leu Lys Ala Gly Thr Tyr Ile Val
             20                  25                  30 ggt gcc tat cca gga aac gct tca tgg gat aaa ctt tca tgc act cgt     144
Gly Ala Tyr Pro Gly Asn Ala Ser Trp Asp Lys Leu Ser Cys Thr Arg
         35                  40                  45 caa tta tca aac ctt gga tgt ttg aga aac aac act gct gtt cca act     192
Gln Leu Ser Asn Leu Gly Cys Leu Arg Asn Asn Thr Ala Val Pro Thr
     50                  55                  60 tgt aaa aga ccg ttt tct ttt tcc aca agg gca atg tct gaa tcc agt     240
Cys Lys Arg Pro Phe Ser Phe Ser Thr Arg Ala Met Ser Glu Ser Ser
 65                  70                  75                  80 gaa aat aag gct cct tca ggg ctt cca att gat ttg aga ggg aaa aga     288
Glu Asn Lys Ala Pro Ser Gly Leu Pro Ile Asp Leu Arg Gly Lys Arg
                 85                  90                  95 gct ttc att gct ggt ata gct gat gat aat ggc tac ggt tgg gcc ata     336
Ala Phe Ile Ala Gly Ile Ala Asp Asp Asn Gly Tyr Gly Trp Ala Ile
            100                 105                 110 gca aaa tct ctt gct gct gct gga gct gaa ata ttg gtt ggg act tgg     384
Ala Lys Ser Leu Ala Ala Ala Gly Ala Glu Ile Leu Val Gly Thr Trp
        115                 120                 125 gtt cct gca ctt aat ata ttt gag aca agc ttg aga cgt gga aaa ttc     432
Val Pro Ala Leu Asn Ile Phe Glu Thr Ser Leu Arg Arg Gly Lys Phe
    130                 135                 140 gac cag tca cga gtg ttg ccg gat ggg tca ttg atg gag att aag aag     480
Asp Gln Ser Arg Val Leu Pro Asp Gly Ser Leu Met Glu Ile Lys Lys
```

```
            145                 150                 155                 160
gtc tat gct ttg gat gct gtg ttt gac aat cct gaa gat gtg cct gaa        528
Val Tyr Ala Leu Asp Ala Val Phe Asp Asn Pro Glu Asp Val Pro Glu
                    165                 170                 175 gat gtg aaa acg aat aag cga tat gca gga tcg tca aac tgg acc gta        576
Asp Val Lys Thr Asn Lys Arg Tyr Ala Gly Ser Ser Asn Trp Thr Val
                180                 185                 190 cag gaa gct gct gaa tgt gtg aaa aaa gat ttt gga agc att gac att        624
Gln Glu Ala Ala Glu Cys Val Lys Lys Asp Phe Gly Ser Ile Asp Ile
            195                 200                 205 ctt gtc cat tcc ctt gca aat ggt cca gag gtt agc aaa cct ctt ctg        672
Leu Val His Ser Leu Ala Asn Gly Pro Glu Val Ser Lys Pro Leu Leu
        210                 215                 220 gag aca tca agg aaa ggc tat ctc gct gtc atc tct gct tcg agt tac        720
Glu Thr Ser Arg Lys Gly Tyr Leu Ala Val Ile Ser Ala Ser Ser Tyr
225                 230                 235                 240 tcc ttt gtt tcc ttg ctg agg cat ttt ctg cca att atg aac cca gga        768
Ser Phe Val Ser Leu Leu Arg His Phe Leu Pro Ile Met Asn Pro Gly
                245                 250                 255 ggt gct tca ata tct ctt act tac att gca tct gaa aga atc att cct        816
Gly Ala Ser Ile Ser Leu Thr Tyr Ile Ala Ser Glu Arg Ile Ile Pro
            260                 265                 270 ggg tat ggt gga ggt atg agt tct gcc aaa gct gca cta gag agt gac        864
Gly Tyr Gly Gly Gly Met Ser Ser Ala Lys Ala Ala Leu Glu Ser Asp
        275                 280                 285 aca cgg gtg ctt gca tat gaa gct gga agg aaa tca aac att agg gtc        912
Thr Arg Val Leu Ala Tyr Glu Ala Gly Arg Lys Ser Asn Ile Arg Val
290                 295                 300 aac acc ata tct gcg ggt cct ttg gga agc cga gca gca aaa gcc att        960
Asn Thr Ile Ser Ala Gly Pro Leu Gly Ser Arg Ala Ala Lys Ala Ile
305                 310                 315                 320 ggg ttc ata gac acc atg att gag tat tcc tac aat aat gga cct att       1008
Gly Phe Ile Asp Thr Met Ile Glu Tyr Ser Tyr Asn Asn Gly Pro Ile
                325                 330                 335 cag aaa aca ctg acc gca gat gaa gtt ggg aat gca gca gcc ttc ttg       1056
Gln Lys Thr Leu Thr Ala Asp Glu Val Gly Asn Ala Ala Ala Phe Leu
            340                 345                 350 gca tct cca ttg gcc tct gcc ata acc ggt gca acc ata tat gtg gac       1104
Ala Ser Pro Leu Ala Ser Ala Ile Thr Gly Ala Thr Ile Tyr Val Asp
        355                 360                 365 aat ggt ttg aat gca atg ggc gtt gca ctg gac agc ccc gtg ttc aaa       1152
Asn Gly Leu Asn Ala Met Gly Val Ala Leu Asp Ser Pro Val Phe Lys
    370                 375                 380 gac ctt aac agc aag aat tag                                           1173
Asp Leu Asn Ser Lys Asn
385                 390

<210> SEQ ID NO 2
<211> LENGTH: 390
<212> TYPE: PRT
<213> ORGANISM: Arabidopsis thaliana

<400> SEQUENCE: 2

Met Ala Ala Thr Ala Ala Ser Ser Leu Gln Ile Ala Thr Arg Arg Pro
  1               5                  10                  15

Ser Met Ser Ser Pro Ser Lys Val Leu Lys Ala Gly Thr Tyr Ile Val
                 20                  25                  30

Gly Ala Tyr Pro Gly Asn Ala Ser Trp Asp Lys Leu Ser Cys Thr Arg
             35                  40                  45
```

```
Gln Leu Ser Asn Leu Gly Cys Leu Arg Asn Asn Thr Ala Val Pro Thr
     50                  55                  60
Cys Lys Arg Pro Phe Ser Phe Ser Thr Arg Ala Met Ser Glu Ser Ser
 65                  70                  75                  80
Glu Asn Lys Ala Pro Ser Gly Leu Pro Ile Asp Leu Arg Gly Lys Arg
                 85                  90                  95
Ala Phe Ile Ala Gly Ile Ala Asp Asp Asn Gly Tyr Gly Trp Ala Ile
            100                 105                 110
Ala Lys Ser Leu Ala Ala Gly Ala Glu Ile Leu Val Gly Thr Trp
        115                 120                 125
Val Pro Ala Leu Asn Ile Phe Glu Thr Ser Leu Arg Arg Gly Lys Phe
    130                 135                 140
Asp Gln Ser Arg Val Leu Pro Asp Gly Ser Leu Met Glu Ile Lys Lys
145                 150                 155                 160
Val Tyr Ala Leu Asp Ala Val Phe Asp Asn Pro Glu Asp Val Pro Glu
                165                 170                 175
Asp Val Lys Thr Asn Lys Arg Tyr Ala Gly Ser Ser Asn Trp Thr Val
            180                 185                 190
Gln Glu Ala Ala Glu Cys Val Lys Lys Asp Phe Gly Ser Ile Asp Ile
        195                 200                 205
Leu Val His Ser Leu Ala Asn Gly Pro Glu Val Ser Lys Pro Leu Leu
    210                 215                 220
Glu Thr Ser Arg Lys Gly Tyr Leu Ala Val Ile Ser Ala Ser Ser Tyr
225                 230                 235                 240
Ser Phe Val Ser Leu Leu Arg His Phe Leu Pro Ile Met Asn Pro Gly
                245                 250                 255
Gly Ala Ser Ile Ser Leu Thr Tyr Ile Ala Ser Glu Arg Ile Ile Pro
            260                 265                 270
Gly Tyr Gly Gly Gly Met Ser Ser Ala Lys Ala Ala Leu Glu Ser Asp
        275                 280                 285
Thr Arg Val Leu Ala Tyr Glu Ala Gly Arg Lys Ser Asn Ile Arg Val
    290                 295                 300
Asn Thr Ile Ser Ala Gly Pro Leu Gly Ser Arg Ala Ala Lys Ala Ile
305                 310                 315                 320
Gly Phe Ile Asp Thr Met Ile Glu Tyr Ser Tyr Asn Asn Gly Pro Ile
                325                 330                 335
Gln Lys Thr Leu Thr Ala Asp Glu Val Gly Asn Ala Ala Ala Phe Leu
            340                 345                 350
Ala Ser Pro Leu Ala Ser Ala Ile Thr Gly Ala Thr Ile Tyr Val Asp
        355                 360                 365
Asn Gly Leu Asn Ala Met Gly Val Ala Leu Asp Ser Pro Val Phe Lys
    370                 375                 380
Asp Leu Asn Ser Lys Asn
385                 390
```

<210> SEQ ID NO 3
<211> LENGTH: 1395
<212> TYPE: DNA
<213> ORGANISM: Arabidopsis thaliana
<220> FEATURE:
<221> NAME/KEY: CDS
<222> LOCATION: (1)..(1395)

<400> SEQUENCE: 3

```
atg aca tct tct ctg tca ctt cac tcc tcc ttc gta cct tcc ttc gct      48
Met Thr Ser Ser Leu Ser Leu His Ser Ser Phe Val Pro Ser Phe Ala
```

-continued

| | 1 | | | | 5 | | | | | 10 | | | | | 15 | | | |
|---|---|---|---|---|---|---|---|---|---|---|---|---|---|---|---|---|---|---|
| | gat | ctc | tcc | gac | cga | ggt | ttg | atc | agt | aag | aac | tct | ccg | acc | agt | gtt | | 96 |
| | Asp | Leu | Ser | Asp | Arg | Gly | Leu | Ile | Ser | Lys | Asn | Ser | Pro | Thr | Ser | Val | | |
| | | | | 20 | | | | | 25 | | | | | 30 | | | | |
| | tcc | att | tcc | aag | gtt | cca | act | tgg | gag | aag | aag | cag | atc | tca | aat | cgg | | 144 |
| | Ser | Ile | Ser | Lys | Val | Pro | Thr | Trp | Glu | Lys | Lys | Gln | Ile | Ser | Asn | Arg | | |
| | | | 35 | | | | | 40 | | | | | 45 | | | | | |
| | aac | tct | ttc | aag | ctg | aat | tgc | gtg | atg | gag | aaa | agt | gtc | gat | ggt | caa | | 192 |
| | Asn | Ser | Phe | Lys | Leu | Asn | Cys | Val | Met | Glu | Lys | Ser | Val | Asp | Gly | Gln | | |
| | | 50 | | | | | 55 | | | | | 60 | | | | | | |
| | act | cat | tct | acc | gtt | aac | aat | acc | act | gat | agc | tta | aat | act | atg | aat | | 240 |
| | Thr | His | Ser | Thr | Val | Asn | Asn | Thr | Thr | Asp | Ser | Leu | Asn | Thr | Met | Asn | | |
| | 65 | | | | 70 | | | | | 75 | | | | | 80 | | | |
| | atc | aaa | gaa | gaa | gct | agc | gtc | tct | aca | tta | ttg | gtg | aac | ttg | gat | aat | | 288 |
| | Ile | Lys | Glu | Glu | Ala | Ser | Val | Ser | Thr | Leu | Leu | Val | Asn | Leu | Asp | Asn | | |
| | | | | | 85 | | | | | 90 | | | | | 95 | | | |
| | aaa | ttt | gat | ccc | ttt | gat | gca | atg | agc | act | ccg | ctt | tac | caa | act | gct | | 336 |
| | Lys | Phe | Asp | Pro | Phe | Asp | Ala | Met | Ser | Thr | Pro | Leu | Tyr | Gln | Thr | Ala | | |
| | | | | 100 | | | | | 105 | | | | | 110 | | | | |
| | act | ttt | aag | cag | cct | tct | gct | att | gaa | aat | gga | cct | tat | gat | tat | aca | | 384 |
| | Thr | Phe | Lys | Gln | Pro | Ser | Ala | Ile | Glu | Asn | Gly | Pro | Tyr | Asp | Tyr | Thr | | |
| | | | 115 | | | | | 120 | | | | | 125 | | | | | |
| | aga | agt | ggc | aat | cct | aca | cgg | gat | gca | ttg | gaa | agc | ctc | ctt | gcg | aag | | 432 |
| | Arg | Ser | Gly | Asn | Pro | Thr | Arg | Asp | Ala | Leu | Glu | Ser | Leu | Leu | Ala | Lys | | |
| | | 130 | | | | | 135 | | | | | 140 | | | | | | |
| | ctt | gac | aag | gca | gat | aga | gca | ttt | tgc | ttt | act | agc | gga | atg | gct | gct | | 480 |
| | Leu | Asp | Lys | Ala | Asp | Arg | Ala | Phe | Cys | Phe | Thr | Ser | Gly | Met | Ala | Ala | | |
| | 145 | | | | 150 | | | | | 155 | | | | | 160 | | | |
| | ctt | agt | gct | gtt | aca | cat | ctt | atc | aaa | aat | ggc | gaa | gaa | att | gtt | gct | | 528 |
| | Leu | Ser | Ala | Val | Thr | His | Leu | Ile | Lys | Asn | Gly | Glu | Glu | Ile | Val | Ala | | |
| | | | | | 165 | | | | | 170 | | | | | 175 | | | |
| | gga | gat | gat | gta | tat | ggt | ggc | tct | gac | aga | tta | cta | tcc | caa | gtt | gtt | | 576 |
| | Gly | Asp | Asp | Val | Tyr | Gly | Gly | Ser | Asp | Arg | Leu | Leu | Ser | Gln | Val | Val | | |
| | | | | 180 | | | | | 185 | | | | | 190 | | | | |
| | cca | aga | tct | ggc | gtt | gtg | gta | aaa | cga | gta | aac | aca | act | aag | tta | gac | | 624 |
| | Pro | Arg | Ser | Gly | Val | Val | Val | Lys | Arg | Val | Asn | Thr | Thr | Lys | Leu | Asp | | |
| | | | 195 | | | | | 200 | | | | | 205 | | | | | |
| | gag | gtt | gct | gct | gca | att | ggt | ccc | caa | aca | aag | ctt | gtg | tgg | ctt | gag | | 672 |
| | Glu | Val | Ala | Ala | Ala | Ile | Gly | Pro | Gln | Thr | Lys | Leu | Val | Trp | Leu | Glu | | |
| | | 210 | | | | | 215 | | | | | 220 | | | | | | |
| | tct | cca | aca | aac | cca | aga | caa | caa | att | tct | gat | ata | cga | aaa | ata | tct | | 720 |
| | Ser | Pro | Thr | Asn | Pro | Arg | Gln | Gln | Ile | Ser | Asp | Ile | Arg | Lys | Ile | Ser | | |
| | 225 | | | | 230 | | | | | 235 | | | | | 240 | | | |
| | gag | atg | gct | cat | gct | caa | ggt | gct | ctt | gtg | ttg | gtg | gac | aac | agt | att | | 768 |
| | Glu | Met | Ala | His | Ala | Gln | Gly | Ala | Leu | Val | Leu | Val | Asp | Asn | Ser | Ile | | |
| | | | | | 245 | | | | | 250 | | | | | 255 | | | |
| | atg | tca | cca | gtg | ctc | tct | cgg | cca | tta | gaa | ctt | gga | gct | gac | atc | gtg | | 816 |
| | Met | Ser | Pro | Val | Leu | Ser | Arg | Pro | Leu | Glu | Leu | Gly | Ala | Asp | Ile | Val | | |
| | | | | 260 | | | | | 265 | | | | | 270 | | | | |
| | atg | cac | tcg | gct | act | aag | ttt | ata | gcc | gga | cac | agt | gac | gtg | atg | gca | | 864 |
| | Met | His | Ser | Ala | Thr | Lys | Phe | Ile | Ala | Gly | His | Ser | Asp | Val | Met | Ala | | |
| | | | 275 | | | | | 280 | | | | | 285 | | | | | |
| | ggt | gtg | ctt | gct | gta | aaa | ggc | gaa | aaa | ttg | gca | aag | gag | gtg | tat | ttc | | 912 |
| | Gly | Val | Leu | Ala | Val | Lys | Gly | Glu | Lys | Leu | Ala | Lys | Glu | Val | Tyr | Phe | | |
| | | 290 | | | | | 295 | | | | | 300 | | | | | | |
| | ctc | caa | aac | tca | gaa | ggt | tct | gga | tta | gct | cct | ttc | gac | tgt | tgg | ctt | | 960 |
| | Leu | Gln | Asn | Ser | Glu | Gly | Ser | Gly | Leu | Ala | Pro | Phe | Asp | Cys | Trp | Leu | | |
| | 305 | | | | 310 | | | | | 315 | | | | | 320 | | | |
| | tgc | ctt | cga | gga | atc | aag | aca | atg | gct | tta | cgg | ata | gaa | aag | caa | cag | | 1008 |

```
Cys Leu Arg Gly Ile Lys Thr Met Ala Leu Arg Ile Glu Lys Gln Gln
                325                 330                 335 gaa aac gca cgg aaa att gca atg tac ttg tct tct cat cca aga gta       1056
Glu Asn Ala Arg Lys Ile Ala Met Tyr Leu Ser Ser His Pro Arg Val
            340                 345                 350 aag aaa gtg tac tat gct ggt cta cca gat cat cct ggt cac cat ctc       1104
Lys Lys Val Tyr Tyr Ala Gly Leu Pro Asp His Pro Gly His His Leu
        355                 360                 365 cac ttc tct cag gcg aag ggt gca gga tca gtt ttt agc ttt ata act       1152
His Phe Ser Gln Ala Lys Gly Ala Gly Ser Val Phe Ser Phe Ile Thr
    370                 375                 380 gga tca gtt gcg ctt tca aag cat ctc gta gaa acc acc aaa tac ttc       1200
Gly Ser Val Ala Leu Ser Lys His Leu Val Glu Thr Thr Lys Tyr Phe
385                 390                 395                 400 agc ata gct gtc agt ttt ggg agt gtt aag tca ctg ata agc atg cca       1248
Ser Ile Ala Val Ser Phe Gly Ser Val Lys Ser Leu Ile Ser Met Pro
                405                 410                 415 tgc ttc atg tca cat gca agc ata cct gca gaa gtt cgt gag gcc aga       1296
Cys Phe Met Ser His Ala Ser Ile Pro Ala Glu Val Arg Glu Ala Arg
            420                 425                 430 ggt ttg acg gaa gat ctt gtc cgt ata tct gca gga att gaa gat gtt       1344
Gly Leu Thr Glu Asp Leu Val Arg Ile Ser Ala Gly Ile Glu Asp Val
        435                 440                 445 gat gat ttg ata tct gat ctt gac att gcc ttc aaa acc ttc cct ctc       1392
Asp Asp Leu Ile Ser Asp Leu Asp Ile Ala Phe Lys Thr Phe Pro Leu
    450                 455                 460 tag                                                                    1395
465

<210> SEQ ID NO 4
<211> LENGTH: 464
<212> TYPE: PRT
<213> ORGANISM: Arabidopsis thaliana

<400> SEQUENCE: 4

Met Thr Ser Ser Leu Ser Leu His Ser Ser Phe Val Pro Ser Phe Ala
 1               5                  10                  15

Asp Leu Ser Asp Arg Gly Leu Ile Ser Lys Asn Ser Pro Thr Ser Val
            20                  25                  30

Ser Ile Ser Lys Val Pro Thr Trp Glu Lys Lys Gln Ile Ser Asn Arg
        35                  40                  45

Asn Ser Phe Lys Leu Asn Cys Val Met Glu Lys Ser Val Asp Gly Gln
    50                  55                  60

Thr His Ser Thr Val Asn Asn Thr Thr Asp Ser Leu Asn Thr Met Asn
65                  70                  75                  80

Ile Lys Glu Glu Ala Ser Val Ser Thr Leu Leu Val Asn Leu Asp Asn
                85                  90                  95

Lys Phe Asp Pro Phe Asp Ala Met Ser Thr Pro Leu Tyr Gln Thr Ala
            100                 105                 110

Thr Phe Lys Gln Pro Ser Ala Ile Glu Asn Gly Pro Tyr Asp Tyr Thr
        115                 120                 125

Arg Ser Gly Asn Pro Thr Arg Asp Ala Leu Glu Ser Leu Leu Ala Lys
    130                 135                 140

Leu Asp Lys Ala Asp Arg Ala Phe Cys Phe Thr Ser Gly Met Ala Ala
145                 150                 155                 160

Leu Ser Ala Val Thr His Leu Ile Lys Asn Gly Glu Glu Ile Val Ala
                165                 170                 175

Gly Asp Asp Val Tyr Gly Gly Ser Asp Arg Leu Leu Ser Gln Val Val
```

```
                180                 185                 190
Pro Arg Ser Gly Val Val Lys Arg Val Asn Thr Thr Lys Leu Asp
        195                 200                 205
Glu Val Ala Ala Ala Ile Gly Pro Gln Thr Lys Leu Val Trp Leu Glu
    210                 215                 220
Ser Pro Thr Asn Pro Arg Gln Gln Ile Ser Asp Ile Arg Lys Ile Ser
225                 230                 235                 240
Glu Met Ala His Ala Gln Gly Ala Leu Val Leu Val Asp Asn Ser Ile
                245                 250                 255
Met Ser Pro Val Leu Ser Arg Pro Leu Glu Leu Gly Ala Asp Ile Val
                260                 265                 270
Met His Ser Ala Thr Lys Phe Ile Ala Gly His Ser Asp Val Met Ala
            275                 280                 285
Gly Val Leu Ala Val Lys Gly Glu Lys Leu Ala Lys Glu Val Tyr Phe
            290                 295                 300
Leu Gln Asn Ser Glu Gly Ser Gly Leu Ala Pro Phe Asp Cys Trp Leu
305                 310                 315                 320
Cys Leu Arg Gly Ile Lys Thr Met Ala Leu Arg Ile Glu Lys Gln Gln
                325                 330                 335
Glu Asn Ala Arg Lys Ile Ala Met Tyr Leu Ser Ser His Pro Arg Val
                340                 345                 350
Lys Lys Val Tyr Tyr Ala Gly Leu Pro Asp His Pro Gly His His Leu
                355                 360                 365
His Phe Ser Gln Ala Lys Gly Ala Gly Ser Val Phe Ser Phe Ile Thr
            370                 375                 380
Gly Ser Val Ala Leu Ser Lys His Leu Val Glu Thr Thr Lys Tyr Phe
385                 390                 395                 400
Ser Ile Ala Val Ser Phe Gly Ser Val Lys Ser Leu Ile Ser Met Pro
                405                 410                 415
Cys Phe Met Ser His Ala Ser Ile Pro Ala Glu Val Arg Glu Ala Arg
                420                 425                 430
Gly Leu Thr Glu Asp Leu Val Arg Ile Ser Ala Gly Ile Glu Asp Val
            435                 440                 445
Asp Asp Leu Ile Ser Asp Leu Asp Ile Ala Phe Lys Thr Phe Pro Leu
    450                 455                 460

<210> SEQ ID NO 5
<211> LENGTH: 1185
<212> TYPE: DNA
<213> ORGANISM: Arabidopsis thaliana
<220> FEATURE:
<221> NAME/KEY: CDS
<222> LOCATION: (1)..(1185)

<400> SEQUENCE: 5 atg tca atc ctt caa gtc tct act tcg tct ctt tct tct tct act ctt    48
Met Ser Ile Leu Gln Val Ser Thr Ser Ser Leu Ser Ser Ser Thr Leu
  1               5                  10                  15 ctc tcc ata tct ccc aga aaa tct ctc tca tct acc aag tca tgc cgg    96
Leu Ser Ile Ser Pro Arg Lys Ser Leu Ser Ser Thr Lys Ser Cys Arg
             20                  25                  30 ata gtt cga tgt tcc gtc gag gga act act gta acc gag aga aaa gtc   144
Ile Val Arg Cys Ser Val Glu Gly Thr Thr Val Thr Glu Arg Lys Val
         35                  40                  45 tcg gca acc agc gag cca ctt ctt ctg aga gct gtt aaa ggt gaa gtt   192
Ser Ala Thr Ser Glu Pro Leu Leu Leu Arg Ala Val Lys Gly Glu Val
     50                  55                  60
```

```
gtt gat aga cct ccg gtt tgg ctt atg agg caa gct ggg agg tac atg     240
Val Asp Arg Pro Pro Val Trp Leu Met Arg Gln Ala Gly Arg Tyr Met
 65                  70                  75                  80 aag agt tat caa act ctc tgt gag aag tat cct tct ttc aga gat aga     288
Lys Ser Tyr Gln Thr Leu Cys Glu Lys Tyr Pro Ser Phe Arg Asp Arg
                 85                  90                  95 tca gag aat gca gat ctt gtg gtg gaa att tct ttg cag cca tgg aag     336
Ser Glu Asn Ala Asp Leu Val Val Glu Ile Ser Leu Gln Pro Trp Lys
            100                 105                 110 gtg ttt aag cca gat ggg gtg att ctg ttc tca gac att ctc act cca     384
Val Phe Lys Pro Asp Gly Val Ile Leu Phe Ser Asp Ile Leu Thr Pro
        115                 120                 125 ttg tct gga atg aac ata cct ttc gac att gtt aaa gga aaa ggt cct     432
Leu Ser Gly Met Asn Ile Pro Phe Asp Ile Val Lys Gly Lys Gly Pro
    130                 135                 140 atc atc ttt aac ccg cct caa tca gct gcc gac gtt gct caa gtt aga     480
Ile Ile Phe Asn Pro Pro Gln Ser Ala Ala Asp Val Ala Gln Val Arg
145                 150                 155                 160 gaa ttc gta cca gag gaa tct gtt cct tat gtt gga gaa gca ctc aga     528
Glu Phe Val Pro Glu Glu Ser Val Pro Tyr Val Gly Glu Ala Leu Arg
                165                 170                 175 aga tta aga aat gag gtg aac aat gaa gcc gct gtt ctg gga ttt gtt     576
Arg Leu Arg Asn Glu Val Asn Asn Glu Ala Ala Val Leu Gly Phe Val
            180                 185                 190 gga gct cca ttt aca ctt tct tcg tat gta atc gaa ggt ggc tca tct     624
Gly Ala Pro Phe Thr Leu Ser Ser Tyr Val Ile Glu Gly Gly Ser Ser
        195                 200                 205 aag aac ttc aca cag ata aaa aga tta gct ttt tct caa ccc aag gtt     672
Lys Asn Phe Thr Gln Ile Lys Arg Leu Ala Phe Ser Gln Pro Lys Val
    210                 215                 220 cta cat gcc tta ctc cag aag ttc aca acc tcg atg ata acg tac ata     720
Leu His Ala Leu Leu Gln Lys Phe Thr Thr Ser Met Ile Thr Tyr Ile
225                 230                 235                 240 cgc tat caa gca gat agc gga gct caa gct gtg caa ata ttc gac tct     768
Arg Tyr Gln Ala Asp Ser Gly Ala Gln Ala Val Gln Ile Phe Asp Ser
                245                 250                 255 tgg gca acc gag ctt agc ccg gtg gat ttt gag gag ttt agc tta cct     816
Trp Ala Thr Glu Leu Ser Pro Val Asp Phe Glu Glu Phe Ser Leu Pro
            260                 265                 270 tat ctc aaa cag att gtg gaa gct gtg aaa caa act cac cca aac cta     864
Tyr Leu Lys Gln Ile Val Glu Ala Val Lys Gln Thr His Pro Asn Leu
        275                 280                 285 cct ctc ata cta tat gct agt gga tca gga ggt ttg cta gag aga ctg     912
Pro Leu Ile Leu Tyr Ala Ser Gly Ser Gly Gly Leu Leu Glu Arg Leu
    290                 295                 300 gct cgg acc ggt gtg gat gtt gtg agc ttg gac tgg act gtg gac atg     960
Ala Arg Thr Gly Val Asp Val Val Ser Leu Asp Trp Thr Val Asp Met
305                 310                 315                 320 gct gaa gga aga gac cgg cta gga aga gac ata gca gtt caa gga aac    1008
Ala Glu Gly Arg Asp Arg Leu Gly Arg Asp Ile Ala Val Gln Gly Asn
                325                 330                 335 gtt gat ccg gga gtt cta ttt gga tcg aaa gaa ttt atc aca agc cgg    1056
Val Asp Pro Gly Val Leu Phe Gly Ser Lys Glu Phe Ile Thr Ser Arg
            340                 345                 350 att cat gat act gtg aag aaa gct ggg aga gat aaa cac att ctc aac    1104
Ile His Asp Thr Val Lys Lys Ala Gly Arg Asp Lys His Ile Leu Asn
        355                 360                 365 ttg ggg cat ggt att aaa gtt gga acc cct gaa gag aat gta gca cac    1152
Leu Gly His Gly Ile Lys Val Gly Thr Pro Glu Glu Asn Val Ala His
```

```
              370                 375                 380
ttc ttt gag gtt gct caa gaa att aga tat taa                          1185
Phe Phe Glu Val Ala Gln Glu Ile Arg Tyr
385                 390                 395

<210> SEQ ID NO 6
<211> LENGTH: 394
<212> TYPE: PRT
<213> ORGANISM: Arabidopsis thaliana

<400> SEQUENCE: 6

Met Ser Ile Leu Gln Val Ser Thr Ser Ser Leu Ser Ser Ser Thr Leu
  1               5                  10                  15

Leu Ser Ile Ser Pro Arg Lys Ser Leu Ser Ser Thr Lys Ser Cys Arg
                 20                  25                  30

Ile Val Arg Cys Ser Val Glu Gly Thr Thr Val Thr Glu Arg Lys Val
             35                  40                  45

Ser Ala Thr Ser Glu Pro Leu Leu Arg Ala Val Lys Gly Glu Val
         50                  55                  60

Val Asp Arg Pro Pro Val Trp Leu Met Arg Gln Ala Gly Arg Tyr Met
 65                  70                  75                  80

Lys Ser Tyr Gln Thr Leu Cys Glu Lys Tyr Pro Ser Phe Arg Asp Arg
                 85                  90                  95

Ser Glu Asn Ala Asp Leu Val Val Glu Ile Ser Leu Gln Pro Trp Lys
            100                 105                 110

Val Phe Lys Pro Asp Gly Val Ile Leu Phe Ser Asp Ile Leu Thr Pro
            115                 120                 125

Leu Ser Gly Met Asn Ile Pro Phe Asp Ile Val Lys Gly Lys Gly Pro
        130                 135                 140

Ile Ile Phe Asn Pro Pro Gln Ser Ala Ala Asp Val Ala Gln Val Arg
145                 150                 155                 160

Glu Phe Val Pro Glu Glu Ser Val Pro Tyr Val Gly Glu Ala Leu Arg
                165                 170                 175

Arg Leu Arg Asn Glu Val Asn Asn Glu Ala Ala Val Leu Gly Phe Val
            180                 185                 190

Gly Ala Pro Phe Thr Leu Ser Ser Tyr Val Ile Glu Gly Gly Ser Ser
        195                 200                 205

Lys Asn Phe Thr Gln Ile Lys Arg Leu Ala Phe Ser Gln Pro Lys Val
    210                 215                 220

Leu His Ala Leu Leu Gln Lys Phe Thr Thr Ser Met Ile Thr Tyr Ile
225                 230                 235                 240

Arg Tyr Gln Ala Asp Ser Gly Ala Gln Ala Val Gln Ile Phe Asp Ser
                245                 250                 255

Trp Ala Thr Glu Leu Ser Pro Val Asp Phe Glu Glu Phe Ser Leu Pro
            260                 265                 270

Tyr Leu Lys Gln Ile Val Glu Ala Val Lys Gln Thr His Pro Asn Leu
        275                 280                 285

Pro Leu Ile Leu Tyr Ala Ser Gly Ser Gly Gly Leu Leu Glu Arg Leu
    290                 295                 300

Ala Arg Thr Gly Val Asp Val Val Ser Leu Asp Trp Thr Val Asp Met
305                 310                 315                 320

Ala Glu Gly Arg Asp Arg Leu Gly Arg Asp Ile Ala Val Gln Gly Asn
                325                 330                 335

Val Asp Pro Gly Val Leu Phe Gly Ser Lys Glu Phe Ile Thr Ser Arg
            340                 345                 350
```

```
Ile His Asp Thr Val Lys Lys Ala Gly Arg Asp Lys His Ile Leu Asn
            355                 360                 365

Leu Gly His Gly Ile Lys Val Gly Thr Pro Glu Glu Asn Val Ala His
        370                 375                 380

Phe Phe Glu Val Ala Gln Glu Ile Arg Tyr
385                 390

<210> SEQ ID NO 7
<211> LENGTH: 1149
<212> TYPE: DNA
<213> ORGANISM: Arabidopsis thaliana
<220> FEATURE:
<221> NAME/KEY: CDS
<222> LOCATION: (1)..(1149)

<400> SEQUENCE: 7 atg gat att gct tcg tca tct ctc tca caa gct cac aaa gtc gtt ctc      48
Met Asp Ile Ala Ser Ser Ser Leu Ser Gln Ala His Lys Val Val Leu
  1               5                  10                  15 acg cgt caa cct tct tcc cgg gtc aac acc tgc tcc ctt ggc tcg gtc      96
Thr Arg Gln Pro Ser Ser Arg Val Asn Thr Cys Ser Leu Gly Ser Val
             20                  25                  30 tcc gct atc gga ttc tct ctt ccg cag att agc tct cca gct tta ggt     144
Ser Ala Ile Gly Phe Ser Leu Pro Gln Ile Ser Ser Pro Ala Leu Gly
         35                  40                  45 aaa tgt cgc cgg aaa caa agc tct tct ggg ttc gtg aaa gct tgt gtt     192
Lys Cys Arg Arg Lys Gln Ser Ser Ser Gly Phe Val Lys Ala Cys Val
 50                  55                  60 gct gtt gaa cag aaa acc cga act gct atc atc aga att ggc aca agg     240
Ala Val Glu Gln Lys Thr Arg Thr Ala Ile Ile Arg Ile Gly Thr Arg
 65                  70                  75                  80 gga agt cct cta gca ctt gct caa gca tac gag acg cga gaa aag ctc     288
Gly Ser Pro Leu Ala Leu Ala Gln Ala Tyr Glu Thr Arg Glu Lys Leu
                 85                  90                  95 aag aag aaa cac cct gaa ctc gtt gaa gat gga gct att cat atc gag     336
Lys Lys Lys His Pro Glu Leu Val Glu Asp Gly Ala Ile His Ile Glu
            100                 105                 110 atc att aaa acg act ggt gat aag att ctt tcg caa ccg ctt gct gat     384
Ile Ile Lys Thr Thr Gly Asp Lys Ile Leu Ser Gln Pro Leu Ala Asp
        115                 120                 125 att ggt ggg aaa gga ctt ttc acc aaa gaa ata gac gag gcc ttg ata     432
Ile Gly Gly Lys Gly Leu Phe Thr Lys Glu Ile Asp Glu Ala Leu Ile
    130                 135                 140 aat ggt cat att gac ata gct gtg cac tca atg aaa gat gtc cca act     480
Asn Gly His Ile Asp Ile Ala Val His Ser Met Lys Asp Val Pro Thr
145                 150                 155                 160 tac tta cca gaa aaa acg att tta cct tgt aac ctt ccg cgt gag gat     528
Tyr Leu Pro Glu Lys Thr Ile Leu Pro Cys Asn Leu Pro Arg Glu Asp
                165                 170                 175 gtt cga gat gcg ttt att tgt cta act gca gcc acg tta gct gag ctt     576
Val Arg Asp Ala Phe Ile Cys Leu Thr Ala Ala Thr Leu Ala Glu Leu
            180                 185                 190 cca gct gga agc gtt gtg gga aca gct tct ctc agg aga aaa tcg cag     624
Pro Ala Gly Ser Val Val Gly Thr Ala Ser Leu Arg Arg Lys Ser Gln
        195                 200                 205 att ctc cac aaa tat cct gca tta cat gtt gag gaa aac ttc agg ggt     672
Ile Leu His Lys Tyr Pro Ala Leu His Val Glu Glu Asn Phe Arg Gly
    210                 215                 220 aat gtg cag aca aga cta tca aaa cta caa gga gga aag gtc caa gca     720
Asn Val Gln Thr Arg Leu Ser Lys Leu Gln Gly Gly Lys Val Gln Ala
```

```
                 225                 230                 235                 240
act cta tta gca cta gct ggt ctt aag aga ttg agt atg aca gag aat          768
Thr Leu Leu Ala Leu Ala Gly Leu Lys Arg Leu Ser Met Thr Glu Asn
                245                 250                 255 gtc gca tct atc tta tct ctc gat gaa atg ctt cca gct gtt gct caa          816
Val Ala Ser Ile Leu Ser Leu Asp Glu Met Leu Pro Ala Val Ala Gln
            260                 265                 270 gga gct att gga att gcc tgt aga act gat gat gat aaa atg gca act          864
Gly Ala Ile Gly Ile Ala Cys Arg Thr Asp Asp Asp Lys Met Ala Thr
                275                 280                 285 tac tta gcc tca ctg aac cac gag gaa aca aga cta gcg att tca tgc          912
Tyr Leu Ala Ser Leu Asn His Glu Glu Thr Arg Leu Ala Ile Ser Cys
        290                 295                 300 gag aga gct ttt ctt gaa acg cta gat ggc tca tgc cgt act cct att          960
Glu Arg Ala Phe Leu Glu Thr Leu Asp Gly Ser Cys Arg Thr Pro Ile
305                 310                 315                 320 gct gga tac gca tcc aag gac gaa gaa ggc aac tgc att ttc aga gga         1008
Ala Gly Tyr Ala Ser Lys Asp Glu Glu Gly Asn Cys Ile Phe Arg Gly
                325                 330                 335 ttg gtt gct tcc cct gac ggt act aaa gtt ctt gag acc tca aga aaa         1056
Leu Val Ala Ser Pro Asp Gly Thr Lys Val Leu Glu Thr Ser Arg Lys
            340                 345                 350 ggt cca tac gtg tat gaa gac atg gtg aag atg gga aaa gac gcg ggg         1104
Gly Pro Tyr Val Tyr Glu Asp Met Val Lys Met Gly Lys Asp Ala Gly
        355                 360                 365 caa gaa ttg cta tct cgt gct ggt cct ggc ttc ttc ggc aac tga             1149
Gln Glu Leu Leu Ser Arg Ala Gly Pro Gly Phe Phe Gly Asn
370                 375                 380
```

<210> SEQ ID NO 8
<211> LENGTH: 382
<212> TYPE: PRT
<213> ORGANISM: Arabidopsis thaliana

<400> SEQUENCE: 8

```
Met Asp Ile Ala Ser Ser Ser Leu Ser Gln Ala His Lys Val Val Leu
 1               5                  10                  15

Thr Arg Gln Pro Ser Ser Arg Val Asn Thr Cys Ser Leu Gly Ser Val
            20                  25                  30

Ser Ala Ile Gly Phe Ser Leu Pro Gln Ile Ser Ser Pro Ala Leu Gly
        35                  40                  45

Lys Cys Arg Arg Lys Gln Ser Ser Gly Phe Val Lys Ala Cys Val
     50                  55                  60

Ala Val Glu Gln Lys Thr Arg Thr Ala Ile Ile Arg Ile Gly Thr Arg
65                  70                  75                  80

Gly Ser Pro Leu Ala Leu Ala Gln Ala Tyr Glu Thr Arg Glu Lys Leu
                85                  90                  95

Lys Lys Lys His Pro Glu Leu Val Glu Asp Gly Ala Ile His Ile Glu
            100                 105                 110

Ile Ile Lys Thr Thr Gly Asp Lys Ile Leu Ser Gln Pro Leu Ala Asp
        115                 120                 125

Ile Gly Gly Lys Gly Leu Phe Thr Lys Glu Ile Asp Glu Ala Leu Ile
    130                 135                 140

Asn Gly His Ile Asp Ile Ala Val His Ser Met Lys Asp Val Pro Thr
145                 150                 155                 160

Tyr Leu Pro Glu Lys Thr Ile Leu Pro Cys Asn Leu Pro Arg Glu Asp
                165                 170                 175
```

```
Val Arg Asp Ala Phe Ile Cys Leu Thr Ala Ala Thr Leu Ala Glu Leu
            180                 185                 190

Pro Ala Gly Ser Val Val Gly Thr Ala Ser Leu Arg Arg Lys Ser Gln
            195                 200                 205

Ile Leu His Lys Tyr Pro Ala Leu His Val Glu Glu Asn Phe Arg Gly
            210                 215                 220

Asn Val Gln Thr Arg Leu Ser Lys Leu Gln Gly Gly Lys Val Gln Ala
225                 230                 235                 240

Thr Leu Leu Ala Leu Ala Gly Leu Lys Arg Leu Ser Met Thr Glu Asn
            245                 250                 255

Val Ala Ser Ile Leu Ser Leu Asp Glu Met Leu Pro Ala Val Ala Gln
            260                 265                 270

Gly Ala Ile Gly Ile Ala Cys Arg Thr Asp Asp Lys Met Ala Thr
            275                 280                 285

Tyr Leu Ala Ser Leu Asn His Glu Glu Thr Arg Leu Ala Ile Ser Cys
            290                 295                 300

Glu Arg Ala Phe Leu Glu Thr Leu Asp Gly Ser Cys Arg Thr Pro Ile
305                 310                 315                 320

Ala Gly Tyr Ala Ser Lys Asp Glu Gly Asn Cys Ile Phe Arg Gly
            325                 330                 335

Leu Val Ala Ser Pro Asp Gly Thr Lys Val Leu Glu Thr Ser Arg Lys
            340                 345                 350

Gly Pro Tyr Val Tyr Glu Asp Met Val Lys Met Gly Lys Asp Ala Gly
            355                 360                 365

Gln Glu Leu Leu Ser Arg Ala Gly Pro Gly Phe Phe Gly Asn
            370                 375                 380

<210> SEQ ID NO 9
<211> LENGTH: 1161
<212> TYPE: DNA
<213> ORGANISM: Arabidopsis thaliana
<220> FEATURE:
<221> NAME/KEY: CDS
<222> LOCATION: (1)..(1161)

<400> SEQUENCE: 9 atg gct tct cac tcg tcg act ctc ctc tct tct cct act ttc gct cct     48
Met Ala Ser His Ser Ser Thr Leu Leu Ser Ser Pro Thr Phe Ala Pro
 1               5                  10                  15 ttc tcc tct cat cgt ctt cat tat tct ccc aat ccc tct act ctc aga     96
Phe Ser Ser His Arg Leu His Tyr Ser Pro Asn Pro Ser Thr Leu Arg
            20                  25                  30 ttc tcc cgt cca atc aga aat aaa cct aat ctc gcc ttg cga tgt tca    144
Phe Ser Arg Pro Ile Arg Asn Lys Pro Asn Leu Ala Leu Arg Cys Ser
        35                  40                  45 gtc tca att gag aaa gaa gtt ccc gaa act gaa cga ccc ttt act ttc    192
Val Ser Ile Glu Lys Glu Val Pro Glu Thr Glu Arg Pro Phe Thr Phe
 50                  55                  60 ctt agg gat tct gat gac gtc act cca tct tct tct tct tct tcc gtc    240
Leu Arg Asp Ser Asp Asp Val Thr Pro Ser Ser Ser Ser Ser Ser Val
 65                  70                  75                  80 agg gct cgt ttc gag act atg att agg gct gct caa gac agt gtt tgt    288
Arg Ala Arg Phe Glu Thr Met Ile Arg Ala Ala Gln Asp Ser Val Cys
                85                  90                  95 gat gca att gaa gct ata gaa ggc ggt cct aag ttt aaa gaa gat gtt    336
Asp Ala Ile Glu Ala Ile Glu Gly Gly Pro Lys Phe Lys Glu Asp Val
            100                 105                 110 tgg tct cga cct ggt ggt ggc ggt gga atc agt cgt gtg ttg cag gac    384
```

|     |     |     |     |     |     |     |     |     |     |     |     |     |     |     |
|---|---|---|---|---|---|---|---|---|---|---|---|---|---|---|
| Trp | Ser | Arg | Pro | Gly | Gly | Gly | Gly | Ile | Ser | Arg | Val | Leu | Gln | Asp |
|     | 115 |     |     |     | 120 |     |     |     |     | 125 |     |     |     |     |

```
ggg aat gtc ttt gag aaa gct ggt gtt aat gtc tct gtg gtt tat ggt          432
Gly Asn Val Phe Glu Lys Ala Gly Val Asn Val Ser Val Val Tyr Gly
    130                 135                 140 gtt atg cct cct gaa gct tat aga gct gca aag ggc tca gct tct gat          480
Val Met Pro Pro Glu Ala Tyr Arg Ala Ala Lys Gly Ser Ala Ser Asp
145                 150                 155                 160 cag aaa cct ggt cct gtt ccg ttc ttc gct gct gga gtc agc tcg gtt          528
Gln Lys Pro Gly Pro Val Pro Phe Phe Ala Ala Gly Val Ser Ser Val
                165                 170                 175 ttg cat ccc aag aac cct ttt gcc cca acc ctg cat ttc aat tat cgc          576
Leu His Pro Lys Asn Pro Phe Ala Pro Thr Leu His Phe Asn Tyr Arg
                180                 185                 190 tat ttc gag aca gat gct cca aag gat gtt cct gga gct cca agg caa          624
Tyr Phe Glu Thr Asp Ala Pro Lys Asp Val Pro Gly Ala Pro Arg Gln
            195                 200                 205 tgg tgg ttt ggt ggt ggc act gat ttc act cct gct tac atc ttt gaa          672
Trp Trp Phe Gly Gly Gly Thr Asp Phe Thr Pro Ala Tyr Ile Phe Glu
    210                 215                 220 gaa gat gtc aag cat ttc cat tcg att caa aag caa gcc tgt gac aaa          720
Glu Asp Val Lys His Phe His Ser Ile Gln Lys Gln Ala Cys Asp Lys
225                 230                 235                 240 ttt gac cct tcc ttc tat ccc cga ttc aag aag tgg tgt gat gac tac          768
Phe Asp Pro Ser Phe Tyr Pro Arg Phe Lys Lys Trp Cys Asp Asp Tyr
                245                 250                 255 ttt tac atc aag cac cgt gat gag aga cga gga ctt gga ggg ata ttt          816
Phe Tyr Ile Lys His Arg Asp Glu Arg Arg Gly Leu Gly Gly Ile Phe
                260                 265                 270 ttt gat gat ctt aat gac tat gat cag gaa atg ctt ctg tca ttt gcc          864
Phe Asp Asp Leu Asn Asp Tyr Asp Gln Glu Met Leu Leu Ser Phe Ala
            275                 280                 285 act gaa tgc gca aac tca gtg gtg ccg gct tat ata cct ata gta gag          912
Thr Glu Cys Ala Asn Ser Val Val Pro Ala Tyr Ile Pro Ile Val Glu
    290                 295                 300 aaa agg aaa gac atg gaa ttt aca gag cag cac aag gca tgg caa cag          960
Lys Arg Lys Asp Met Glu Phe Thr Glu Gln His Lys Ala Trp Gln Gln
305                 310                 315                 320 ttg cga cga ggg cga tat gtc gaa ttc aac ttg gta tat gat cgg gga         1008
Leu Arg Arg Gly Arg Tyr Val Glu Phe Asn Leu Val Tyr Asp Arg Gly
                325                 330                 335 acg aca ttt ggt ctg aag aca gga gga cga ata gag agc att ctc gtc         1056
Thr Thr Phe Gly Leu Lys Thr Gly Gly Arg Ile Glu Ser Ile Leu Val
                340                 345                 350 tct ctt ccg ctt tca gca aga tgg gaa tat gac cat aaa ccg gaa gag         1104
Ser Leu Pro Leu Ser Ala Arg Trp Glu Tyr Asp His Lys Pro Glu Glu
            355                 360                 365 ggg acc gaa gag tgg aag cwa ttg gat gct tgc atc aac ccg aag gag         1152
Gly Thr Glu Glu Trp Lys Xaa Leu Asp Ala Cys Ile Asn Pro Lys Glu
    370                 375                 380 tgg atc tag                                                             1161
Trp Ile
385
```

```
<210> SEQ ID NO 10
<211> LENGTH: 386
<212> TYPE: PRT
<213> ORGANISM: Arabidopsis thaliana

<400> SEQUENCE: 10
```

```
Met Ala Ser His Ser Ser Thr Leu Leu Ser Ser Pro Thr Phe Ala Pro
 1               5                  10                  15

Phe Ser Ser His Arg Leu His Tyr Ser Pro Asn Pro Ser Thr Leu Arg
                20                  25                  30

Phe Ser Arg Pro Ile Arg Asn Lys Pro Asn Leu Ala Leu Arg Cys Ser
            35                  40                  45

Val Ser Ile Glu Lys Glu Val Pro Glu Thr Glu Arg Pro Phe Thr Phe
 50                  55                  60

Leu Arg Asp Ser Asp Asp Val Thr Pro Ser Ser Ser Ser Ser Ser Val
 65                  70                  75                  80

Arg Ala Arg Phe Glu Thr Met Ile Arg Ala Ala Gln Asp Ser Val Cys
                85                  90                  95

Asp Ala Ile Glu Ala Ile Glu Gly Gly Pro Lys Phe Lys Glu Asp Val
            100                 105                 110

Trp Ser Arg Pro Gly Gly Gly Gly Ile Ser Arg Val Leu Gln Asp
            115                 120                 125

Gly Asn Val Phe Glu Lys Ala Gly Val Asn Val Ser Val Val Tyr Gly
 130                 135                 140

Val Met Pro Pro Glu Ala Tyr Arg Ala Ala Lys Gly Ser Ala Ser Asp
145                 150                 155                 160

Gln Lys Pro Gly Pro Val Pro Phe Phe Ala Ala Gly Val Ser Ser Val
                165                 170                 175

Leu His Pro Lys Asn Pro Phe Ala Pro Thr Leu His Phe Asn Tyr Arg
            180                 185                 190

Tyr Phe Glu Thr Asp Ala Pro Lys Asp Val Pro Gly Ala Pro Arg Gln
                195                 200                 205

Trp Trp Phe Gly Gly Gly Thr Asp Phe Thr Pro Ala Tyr Ile Phe Glu
210                 215                 220

Glu Asp Val Lys His Phe His Ser Ile Gln Lys Gln Ala Cys Asp Lys
225                 230                 235                 240

Phe Asp Pro Ser Phe Tyr Pro Arg Phe Lys Lys Trp Cys Asp Tyr
                245                 250                 255

Phe Tyr Ile Lys His Arg Asp Glu Arg Arg Gly Leu Gly Gly Ile Phe
                260                 265                 270

Phe Asp Asp Leu Asn Asp Tyr Asp Gln Glu Met Leu Ser Phe Ala
            275                 280                 285

Thr Glu Cys Ala Asn Ser Val Val Pro Ala Tyr Ile Pro Ile Val Glu
            290                 295                 300

Lys Arg Lys Asp Met Glu Phe Thr Glu Gln His Lys Ala Trp Gln Gln
305                 310                 315                 320

Leu Arg Arg Gly Arg Tyr Val Glu Phe Asn Leu Val Tyr Asp Arg Gly
                325                 330                 335

Thr Thr Phe Gly Leu Lys Thr Gly Gly Arg Ile Glu Ser Ile Leu Val
                340                 345                 350

Ser Leu Pro Leu Ser Ala Arg Trp Glu Tyr Asp His Lys Pro Glu Glu
            355                 360                 365

Gly Thr Glu Glu Trp Lys Xaa Leu Asp Ala Cys Ile Asn Pro Lys Glu
 370                 375                 380

Trp Ile
385
```

<210> SEQ ID NO 11
<211> LENGTH: 4198
<212> TYPE: DNA

<213> ORGANISM: Arabidopsis thaliana

<400> SEQUENCE: 11

```
tctagacttg cacattatca ccaatactaa cggtcctagg aatttccaa tcttcatcgg      60
tctatgtaaa catagatcat ttattttgga gaacacattt atattatttt attttagct    120
ttttttggat catgtgatac atatggaaag tacaaaatga aaacttcac gaaaatatgg    180
atcgagatcc aagagatatt ctcaaactag cgaaaaacaa agacaatgct tggacgttag    240
cctgattgga ggttgcaaat gaattcaag cttcagtggc agttaagtcg gttaatataa    300
atctttcagg atattattgt ttcattgatg actcttggaa agatagtgac aagttttgg    360
gcatggatgt ttctgtattt tatcaaatga aggacatcca accatgtgtg ctggaagcac    420
tcgtttgggc aatgaaatgt atgattggcc aagaaaagcg aaaagtaacg tttttataa    480
actgtagatc tgatgaagat aatgtatttc caacaaaat ggccaacatt cgctacatac    540
ttacgattca ggaagatagt gatgagtttg aattttttta tttatctcta atgcttcgaa    600
atgtaaatgt taacacagac cactagatac gaaatgttcg gatataacca catatgatta    660
tctttgtaaa caatactttt tagcattgat ttattatttg agttaatcta ataaagttgt    720
cggaaaaaac tgaaaagtga gaagagaaaa agtcgaaaat tctgaaacgg tttaaagtta    780
accaggattc cggttttat aacagaaccg atcggttttg taattgagac gaaaacttct    840
gatatcactt aaaaacttca cagaaacaac acctcgatct catcgaagct cctctctctt    900
acatatcatc acttcacatc aaccaaacct acttctgtct ctctctctcg ctctctatct    960
ctcacgctct cacaggtttt tttctctctc tgtctctctc ttgttctcca tttgcgtctc   1020
tgtttgtttg atgagtttct gaatgttaaa tgcagatgtg ttttggtttt ctgtggaagt   1080
ttttatatct ctgttgattg agttttctc tgatgttgtt gggctgcgaa aaaaatcgaa   1140
acttgtatta tctctcgttt aggttcgtg ttctctgcat tgatctgctt cttttatttg   1200
ttaactatag tctcgtatgt gaaaaatgtg aactttgttt gttaactcta atccaaatca   1260
ttagaaaaat gcagattgag atttctctaa tgcagtgctt gaaattttgg aaactagggt   1320
tcttgttata atgtttcaag tagtgaactt atgtcaactt gtgctttagg tttgatctga   1380
ttcttaaatt ttgtttcata tgtggtcttt cttacaatgt ttctggattt gttgttttag   1440
tagaagaaaa aattagaaag gttgtgagaa tggcggctac agcagcttca agcttgcaaa   1500
ttgctacacg aaggccgagc atgtcttcgc ccagcaaagt tcttaaagca ggaacctaca   1560
ttgttggtgc ctatccagga aacgcttcat gggataaact ttcatgcact cgtcaattat   1620
caaaccttgg atgtttgaga aacaacactg ctgttccaac ttgtaaaaga ccgttttctt   1680
tttccacaag ggcaatgtct gaatccagtg aaaataaggc tccttcaggg cttccaattg   1740
atttgagagg ttggtttggc atatcttct ttatattcat taagatgctg ttgtggagaa   1800
gacttggtgc tatctgaact aagcaagtgt aaatggtaca gggaaaagag ctttcattgc   1860
tggtatagct gatgataatg ctacggttg gccatagca aaatctcttg ctgctgctgg   1920
agctgaaata ttggttggga cttgggttcc tgtaagtcat tttaggttca gctgctttta   1980
gtttccttca ttttgctaat tatactaacc tatgaatgga tggtctacta ggcacttaat   2040
atatttgaga caagcttgag acgtggaaaa ttcgaccagt cacgagtgta aggacttaca   2100
acatgatctt gtctggtttt atgtaatggg acattaattt tcccatccat atctatattc   2160
aggttgccgg atgggtcatt gatggagatt aagaaggtct atgctttgga tgctgtgttt   2220
gacaatcctg aagatgtgcc tgaagatgtg aaaacgaata agcgatatgc aggatcgtca   2280
```

```
aactggaccg tacaggtata gattagagat acacaaacac gcctgcaagt taagcatgtg    2340
ttactcctta atgctttttg ttgcttaaat caggaagctg ctgaatgtgt gaaaaaagat    2400
tttggaagca ttgacattct tgtccattcc cttgcaaatg gtccagaggt agagaactcg    2460
tatcgatgat tggttacagt aagtgcattg tgttgtatac aaactatttc cttatggtgt    2520
tcacatgtgg gtttaggtta gcaaacctct tctggagaca tcaaggaaag gctatctcgc    2580
tgtcatctct gcttcgagtt actcctttgt ttccttgctg aggcattttc tgccaattat    2640
gaacccaggc atgtaacaaa tttcgtatgt ctctttattc cttgtaaata tgttttctta    2700
tttggttctc tatgatgatt taggaggtgc ttcaatatct cttacttaca ttgcatctga    2760
aagaatcatt cctgggtaag gatggcttct tcacaagtta ttcaaaggaa caaactaatg    2820
cacacacata acgatgtcaa cacattctca caagtatctc tttcattctg tgcaggtatg    2880
gtggaggtat gagttctgcc aaagctgcac tagagagtga cacacgggtg agtttacaat    2940
tctgtttcgt aaactcaaag atgtattggt tagaagtctc ttagtccaaa ctgtgttttc    3000
aacataggtg cttgcatatg aagctggaag gaaatcaaac attagggtca acaccatatc    3060
tgcgggtaat ccatctttcc ctcttacacg cctcgtggta caaataacac gcctcgtctt    3120
ttgaaattat aaaagagtac tactgtttgg gtttcaggtc ctttgggaag ccgagcagca    3180
aaagccattg ggttcataga caccatgatt gagtattcct acaataatgg acctattcag    3240
aaaacactga ccgcaggttc atttccttca aaccatcacc tctcttgtgc ttgttttttt    3300
tcttggaatc ttacggtttt ataaatggcg atgatgtaga tgaagttggg aatgcagcag    3360
ccttcttggc atctccattg gcctctgcca taaccggtgc aaccatatat gtggacaatg    3420
gtttgaatgc aatgggcgtt gcactggaca gccccgtgtt caaagacctt aacagcaaga    3480
attagagtct tgatcgacga ctgaactcga gaaattccgt gttttcgtga gcttgcttgt    3540
ttctttatga gttagtatgt acggcatatg ttccccatcg gctgtctttt ttttctttc    3600 tttaagagaa taaattatgg ttctaggttg ggtcatttag caactatata tgtagtgatg    3660
gattattatt cctcttatga ttgaaaattt gcaagtgaga aaaactatca tgtttcttgt    3720
aagttgtctc ctccagtctc aaatctcaaa ccaatttaca agactcatga aacctaacag    3780
cctctatttg ctaactttg aaagttgtac ataaacctca caaacaatag cagttaattc    3840
tgcacatatc atctaaattt ggctttagta attgaaactg gcataaactt agaagctaat    3900
atgctaaatt tgggaggaaa acgttagcta tcatcttgag ttttttacat atgtaatctc    3960
aaatattact aataagttta gagctctgta tggttgataa tttactaatt agaaccatga    4020
catcaacaat gaagaataca aaacatgatg aatcaacgag aaataaaaag ctcttgaatt    4080
ccagaaagga gataaaaatg actattatat tacttcccctt ctggtcacca gtatcatagt    4140
attatacata aaaaaaaaaa ccaatggcat gttctatatt ccaccttaaa ggcaaaat     4198
```

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
cccagatcta atggcggcta cagcagctt                                        29

```
<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
catgccatgg ctaattcttg ctgttaagg                                      29

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
gatcgagctc cacgagaact gtctccg                                        27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
tcagccatgg gaagacaagt acattgc                                        27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
cttgccatgg cacgagaact gtctccg                                        27

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
catggagctc gaagacaagt acattgca                                       28

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
catcgagctc ctctgtttaa accacgagaa ctgtctccgt cgc                      43

<210> SEQ ID NO 19
```

```
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
tttggagagg acagacctgc                                              20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ggattttggt tttaggaatt agaa                                         24

<210> SEQ ID NO 21
<211> LENGTH: 2028
<212> TYPE: DNA
<213> ORGANISM: Arabidopsis thaliana

<400> SEQUENCE: 21
atgtcaatcc ttcaagtctc tacttcgtct ctttcttctt ctactcttct ctccatatct    60
cccagaaaat ctctctcatc taccaagtca tgccggatag ttcgatgttc cgtcgagggt   120
acttatttct aactctcaat tttgattcat tttgatgaag tttttggtga gttaatatct   180
gggtagttat aaagttgtga attttccaca agtttctctc tttttggca aataggaaac    240 gaattgggtg tttcgtgtag tacttgaatt gattgttttg gttaatctgt tatggattta   300
atagatgggg acaatggtaa tatgaagaaa ctttcagttt ctcttgtacc aataatctct   360
ctggtagaaa tttaggattt ttcgagtttg ttctgcagaa gctatatgat cttctcgtgc   420
ttcttcgaag taacgtatat tgcttaattc tagaattgga acgtttctat ggggtttcat   480
ttgtttcccc tgaattgagt ttgatcatgg aatgtgcaaa agcttacgag tcttaatctt   540
tatgcttaat gggattcaaa ttctttgttt aggaactact gtaaccgaga gaaagtctc    600 ggcaaccagc gagccacttc ttctgagagc tgttaaaggt gaagttgttg atagacctcc   660
ggtttggctt atgaggcaag ctgggaggta catgaaggca agcttgcttc catttatttt   720
gtttactaac tcacattttg cttgttccta tttctttcga attcgtgtga cctgagtgtt   780
tattaatgtg atgaacagag ttatcaaact ctctgtgaga agtatccttc tttcagagat   840
agatcagaga atgcagatct tgtggtggaa atttctttgc agccatggaa ggtgtttaag   900
ccagatgggg tgagttcttt cttctctatg tccatttagt tttggagttt ttctttttat   960
gatctcttaa gttgacatgt ctgtgtttca aaatgtatga aaaggtgatt ctgttctcag  1020
acattctcac tccattgtct ggaatgaaca taccttttcga cattgttaaa ggaaaaggtc  1080
ctatcatctt taacccgcct caatcagctg ccgacgttgc tcaagttaga gaattcgtac  1140
cagaggaatc tgttccttat gttggagaag cactcagaag attaagaaat gaggtactaa  1200
agatagtgtg atgatcgaag caacaaatgc tcttaatctc tttatccaaa aaacaaaaaa  1260
taacaaatgc tcttaagctg aagaatatgt tttatttcag gtgaacaatg aagccgctgt  1320
tctgggattt gttggagctc catttacact ttcttcgtat gtaatcgaag gtggctcatc  1380
taagaacttc acacagataa aaagattagc ttttttctcaa cccaaggtgg attagtaaaa  1440
```

-continued

```
gcttaaagca attgtacaac ttgacaattt ggttaatatc tcagagattg aacagatttt      1500
ctttcttctc aggttctaca tgccttactc cagaagttca caacctcgat gataacgtac      1560
atacgctatc aagcagatag cggagctcaa gctgtgcaaa tattcgactc ttgggcaacc      1620
gagcttagcc cggtggattt tgaggagttt agcttacctt atctcaaaca gattgtggaa      1680
gctgtgaaac aaactcaccc aaacctacct ctcatacttt atgctagtgg atcaggaggt      1740
ttgctagaga gactggctcg gaccggtgtg gatgttgtga gcttggactg gactgtggac      1800
atggctgaag aagagaccg gctaggaaga gacatagcag ttcaaggaaa cgttgatccg       1860
ggagttctat ttggatcgaa agaatttatc acaagccgga ttcatgatac tgtgaagaaa      1920
gctgggagag ataaacacat tctcaacttg gggcatggta ttaaagttgg aacccctgaa      1980
gagaatgtag cacacttctt tgaggttgct caagaaatta gatattaa                   2028
```

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
gggtttccat atgtcaatcc ttcaagtctc      30

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
ttgcgcggcc gcttaatatc taatttcttg agc      33

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
cccggatcca tgtcaatcct tcaagtc      27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
cccacatgta tatctaattt cttgagc      27

<210> SEQ ID NO 26
<211> LENGTH: 3422
<212> TYPE: DNA
<213> ORGANISM: Arabidopsis thaliana -continued

```
<400> SEQUENCE: 26
gagctcttca gaaaaattat gaataaacgt attctgtaaa atctttcaat agtaaaaagt      60
ttcattttcg tatccatcgt tggtacttgg tagacaaatg gtgtacatat acataaccca     120
ggaagatcaa agatgcatat acataaaccc aacggcttcc aaatttcatt tcactgaatc     180
atgttcgaag caagtagtta catacataaa tggagaacaa ccgaaacagt aagcaaaaac     240
cagaatcaca atcatcatca aagcatatat gaaatgaaac cagttcacgg gatatttcag     300
ctgaccagaa tcactagact caatggtttt aacaaactag atagtgttgg gaagctcgat     360
tagtaacggt atttggtgga gtaatctttt ggagcaatca ccaacccacg acccttcctt     420
gcaccacggt agacagtctc aatgatatca atgaactcct gcttgtcctt gagagcccag     480
ttgatcttgt tgttgttacc agttccaaga tcgatcatga tgtgcttgtt cctgaagaag     540
aacatgaccg tagaaggatc gtacagctcg tacatggtgt tgaagtctgg aacctcagtg     600
atgtccacca gataaatgac tgcaaagttc ttaatcgtct cagcaacaga cgcaagcacc     660
tcatccatct acaaaaatca aaacttcga atcaaacag aaaccagaaa ctgaatacta      720
gaatcaattg taagtgaagc cctaaaattt taatcagttc caagataata aagatcacac     780
gaatggctaa agtttcaaac aatcaacaca acatatccgg aatattccaa gtcaccaaat     840
tcgcaagaac aaaacgaagc tataaatcac agaaatggac actaaaacgg acacattcaa     900
aaccttctac atagtaacca actccaacaa ctaggatttt tttgagtgaa accctaattt     960
catcagttct gagctaagga acacaatttt caaacaatca ccacaaagta tcgcaatttt    1020
ccagtacgaa aggatccaaa tcgagagcta tgaactacaa atcgaatcaa aaacatataa    1080
tcaagctcaa gatcgaaata taagataag agaggaagaa acgtttgaca gacctgcata    1140
caggtctcat cccagtcatg gccgaaacga atgacgacga gacgctcttc ctcggccaga    1200
atcgactgat caacagccca accggagtgc agatgtggaa gaagatacga cattctctct    1260
ctctctctct ctctctctct cgacgatttt ccgatctgtt tcgattcaac cttttttctc    1320
tcttgcccta attttatatt ctcttcccaa ttttgttgac ggtgacggcg cgtcgattcc    1380
acgcgtgaac cgcataaagc gtttgggcta agcccttgat aatacttact ttccggccca    1440
ataaaagata aatcgacgag attgcgaaac agacggtgat taaggtagta gaacaccata    1500
atctggtatg agtcattcgt agaggaataa agctctaaaa tctaattatc ctatccaata    1560
tcctctcata gaggtgagag ctaagatttt cccatcaact ccatttgaag cgaaattctc    1620
tgatctctct tcatttattt ttccctctac atctctccca acgatttcca aatctcactt    1680
cactttggct cctccacctg aatccatgga tattgcttcg tcatctctct cacaagctca    1740
caaagtcgtt ctcacgcgtc aaccttcttc ccgggtcaac acctgctccc ttggctcggt    1800
ctccgctatc ggattctctc ttccgcagat tagctctcca gctttaggta atgtcgccg     1860
gaaacaaagc tcttctgggt tcgtgaaagc ttgtgttgct gttgaacaga aaacccgaac    1920
tgctatcatc agaattggca caggggaag gtaaaaatct ctccttttat tctttgtcaa    1980
ctcttttgag tcttaagggg cttgaatgct attggattgg ctttggttcc ttaattctat    2040
taccaagtat cgatttcatg acgaagttcg ttgttcttcc ttgaacttct ctgtcttgat    2100
ccaaagtcag gttgttgaag aacaaatgaa tcaatggtga atgagtttag tttctgagct    2160
gcttatcttc attattttct gcttaatact ctcactatgt aggacagtcc tctagcactt    2220
gctcaagcat acgagacgcg agaaaagctc aagaagaaac accctgaact cgttgaagat    2280
ggagctattc atatcgagat cattaaaacg actggtgata agattctttc gcaaccgctt    2340
```

```
gctgatattg gtgggaaagg acttttcacc aaagaaatag acgaggcctt gataaatggt   2400
catattgaca tagctgtgca ctcaatgaaa gatgtcccaa cttacttacc agaaaaaacg   2460
attttacctt gtaaccttcc gcgtgaggat gttcgagatg cgtttatttg tctaactgca   2520
gccacgttag ctgagcttcc agctggaagc gttgtgggaa cagcttctct caggagaaaa   2580
tcgcagattc tccacaaata tcctgcatta catgtaagtt ttcacaacat agatcacaac   2640
atagaaactg ccatttctta tggatcagtt ttgtctttct atttattgat acatgtcttt   2700
attgcctttt gcaggttgag gaaaacttca ggggtaatgt gcagacaaga ctatcaaaac   2760
tacaaggagg aaaggtccaa gcaactctat tagcactagc tggtcttaag agattgagta   2820
tgacagagaa tgtcgcatct atcttatctc tcgatgaaat gcttccagct gttgctcaag   2880
gagctattgg aattgcctgt agaactgatg atgataaaat ggtatgtcaa gctctcttgg   2940
aatttacatt atttgatgat gtttctattt atgggatctt tggattggca tctatgattt   3000
gtagtaaatg atcggactgg tgttttacat ctgtaggcaa cttacttagc ctcactgaac   3060
cacgaggaaa caagactagc gatttcatgc gagagagctt ttcttgaaac gctagatggc   3120
tcatgccgta ctcctattgc tggatacgca tccaaggacg aagaaggcaa ctgcattttc   3180
agaggattgg ttgcttcccc tgacggtact aaaggtatga aaacatttct acaataacac   3240
atgagaggat aaacacattt cccattgaga aacatcactc atttctcata tcttccatct   3300
ttgtgtcagt tcttgagacc tcaagaaaag gtccatacgt gtatgaagac atggtgaaga   3360
tgggaaaaga cgcggggcaa gaattgctat ctcgtgctgg tcctggcttc ttcggcaact   3420
ga                                                                   3422
```

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27

```
cccagatctc catggatatt gcttcgtc                                         28
```

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28

```
ccctcatgaa gatagcaatt cttgccc                                          27
```

<210> SEQ ID NO 29
<211> LENGTH: 515
<212> TYPE: DNA
<213> ORGANISM: Arabidopsis thaliana

<400> SEQUENCE: 29

```
atggcttctc actcgtcgac tctcctctct tctcctactt tcgctccttt ctcctctcat    60
cgtcttcatt attctcccaa tccctctact ctcagattct cccgtccaat cagaaataaa   120
cctaatctcg ccttgcgatg ttcagtctca attgagaaag aagttcccga aactgaacga   180
```

```
cccttttactt tccttaggga ttctgatgac gtcactccat cttcttcttc ttcttccgtc    240
agggctcgtt tcgagactat gattagggct gctcaagaca gtgtttgtga tgcaattgaa    300
gctatagaag gcggtcctaa gtttaaagaa gatgtttggt ctcgacctgg tggtggcggt    360
ggaatcagtc gtgtgttgca ggacgggaat gtctttgaga aagctggtgt taatgtctct    420
gtggtttatg gtgttatgcc tcctgaagct tatagagctg caaagggctc agcttctgat    480
cagaaacctg gtcctgttcc gttcttcgct gctgg                               515
```

```
<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
ttgacccttc cttctatccc cgattc                                          26
```

```
<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
gttgccatgc cttgtgctgc tctgta                                          26
```

```
<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
gtacctcgag tctagactcg ag                                              22
```

```
<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
cccagatcta tggcttctca ctcgtcg                                         27
```

```
<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
catgccatgg tattcccatc ttgctgaaa                                       29
```

GENES ENCODING PROTEINS ESSENTIAL FOR PLANT GROWTH AND METHODS OF USE

This application claims the benefit of U.S. Provisional Application No. 60/287,571, filed May 22, 2000 now abandoned. This application also claims the benefit of U.S. Provisional Application No. 60/198,218, filed Jul. 27, 1999 now abandoned. This application also claims the benefit of U.S. Provisional Application No. 60/240,929, filed Aug. 20, 1999 now abandoned. This application also claims the benefit of U.S. Provisional Application No. 60/228,810, filed Nov. 22, 1999 now abandoned. This application also claims the benefit of U.S. Provisional Application No. 60/287,572, filed Mar. 27, 2000 now abandoned. The disclosures of these priority documents are hereby expressly incorporated by reference in their entirety into the instant disclosure.

FIELD OF THE INVENTION

The invention relates generally to enzymatic activity involved in ENR-A, CBL, UROD, PBGD, or CPPO in plants. In particular, the invention relates to plant genes that encode a polypeptide having ENR-A, CBL, UROD, PBGD, or CPPO activity. The invention has various utilities, including the recombinant production of polypeptides having ENR-A, CBL, UROD, PBGD, or CPPO activity in heterologous hosts, the screening of chemicals for herbicidal activity, and the use of thereby identified herbicidal chemicals to control the growth of undesired vegetation. The invention may also be applied to the development of herbicide tolerance in plants, plant tissues, plant seeds, and plant cells.

BACKGROUND OF THE INVENTION

The use of herbicides to control undesirable vegetation such as weeds in crop fields has become almost a universal practice. The herbicide market exceeds 15 billion dollars annually. Despite this extensive use, weed control remains a significant and costly problem for farmers.

For example, present herbicides often impose special limitations on farming practices, and the time and method of application and stage of weed plant development often are critical for good weed control with such herbicides, thus creating farm management constraints. Furthermore, since only a few target enzymes are inhibited by currently used herbicides, various weed species are, or may become, resistant to these herbicides. For all of these reasons, the discovery and development of effective new herbicides, in particular those acting on novel target enzymes, is increasingly important.

Novel herbicides can now be discovered using high-throughput screens that implement recombinant DNA technology. Once identified, metabolic enzymes essential to plant growth and development can be recombinantly produced through standard molecular biological techniques and utilized as herbicide targets in screens for novel inhibitors of the enzyme's activity. The novel inhibitors discovered through such screens may then be used as herbicides to control undesirable vegetation. Such herbicides are also useful for selecting herbicide tolerant plants, and seed plants tolerant to the herbicide can be produced, for example by genetic engineering techniques. Thus, herbicides that exhibit greater potency, broader weed spectrum, and more rapid degradation in soil can be applied to crops that are resistant or tolerant to herbicides in order to kill weeds without attendant risk of damage to the crop.

Therefore, in order to meet the future food requirements of the world's growing population in a cost-effective and environmentally safe manner, there exists a long felt and unfulfilled need for novel target enzymes for herbicides, for new and better herbicides inhibiting such target enzymes and for plants tolerant to these new and better herbicides.

SUMMARY OF THE INVENTION

In view of these long felt yet unfulfilled needs, one object of the invention is to provide a method for identifying new or improved herbicides. Another object of the invention is to provide a method for using such new or improved herbicides to suppress the growth of plants such as weeds. Still another object of the invention is to provide improved crop plants, and seed thereof, that are tolerant to such new or improved herbicides.

In furtherance of these and other objects, the present invention provides a DNA molecule comprising a nucleotide sequence, preferably isolated from a plant, that encodes a polypeptide having ENR-A, CBL, UROD, PBGD, or CPPO activity. The inventors are the first to demonstrate that the ENR-A, CBL, UROD, PBGD, or CPPO genes are essential for the growth of a plant, and is therefore good target enzymes for identifying new herbicides. According to one embodiment, the present invention provides a DNA molecule comprising a nucleotide sequence isolated from a plant that encodes the polypeptide set forth in any one of SEQ ID NO:2, SEQ ID NO:4, SEQ ID NO:6, SEQ ID NO:8, or SEQ ID NO:10. For example, the DNA molecule of the invention may comprise a nucleotide sequence set forth in SEQ ID NO:1, SEQ ID NO:3, SEQ ID NO:5, SEQ ID NO:7, or SEQ ID NO:9, respectively. In another example, the DNA molecule of the invention comprises a nucleotide sequence that is substantially similar to any one of the coding sequence set forth in SEQ ID NO:1, SEQ ID NO:3, SEQ ID NO:5, SEQ ID NO:7, or SEQ ID NO:9, and that encodes a polypeptide having ENR-A, CBL, UROD, PBGD, or CPPO activity, respectively. Although a nucleotide sequence provided in SEQ ID NO:1, SEQ ID NO:3, SEQ ID NO:5, SEQ ID NO:7, or SEQ ID NO:9, is isolated from *Arabidopsis thaliana*, using the information provided by the present invention, other nucleotide sequences that encode a polypeptide having ENR-A, CBL, UROD, PBGD, or CPPO activity are obtained from other sources, e.g. from other plants, using standard methods known in the art.

The present invention also provides a nucleotide sequence construct comprising a promoter operatively linked to a DNA molecule of the invention. Further, the present invention provides methods to stably transform such a nucleotide sequence construct into a host cell, and host cells comprising such a nucleotide sequence construct, wherein the host cell is capable of expressing the DNA molecule encoding a polypeptide having ENR-A, CBL, UROD, PBGD, or CPPO activity, respectively. Any suitable cell may be used as a host cell, e.g. a bacterial cell, a yeast cell, or a plant cell.

In accordance with another embodiment, the present invention also relates to the recombinant production of a ENR-A, CBL, UROD, PBGD, or CPPO polypeptide and methods of use of ENR-A, CBL, UROD, PBGD, or CPPO in assays for identifying compounds that interact with ENR-A, CBL, UROD, PBGD, or CPPO polypeptide, respectively. In a preferred embodiment, the present invention provides a plant polypeptide having ENR-A, CBL, UROD, PBGD, or CPPO activity useful for identifying inhibitors of ENR-A, CBL, UROD, PBGD, or CPPO activity, respectively, in in vivo and in vitro assays. Preferably the isolated polypeptide of the present invention comprises an amino acid sequence substantially similar to any one of the amino acid sequence set forth in SEQ ID NO:2, SEQ ID NO:4, SEQ ID NO:6, SEQ ID NO:8, or SEQ ID NO:10, respectively. More preferably, this enzyme comprises the amino acid sequence set forth in SEQ ID NO:2, SEQ ID NO:4, SEQ ID NO:6, SEQ ID NO:8, or SEQ ID NO:10.

The present invention further provides methods of using purified polypeptides having ENR-A, CBL, UROD, PBGD, or CPPO activity, preferably polypeptides derived from plant sources, in assays to screen for and identify compounds that interact with a ENR-A, CBL, UROD, PBGD, or CPPO polypeptide, respectively. Such compounds are preferably inhibitors of ENR-A, CBL, UROD, PBGD, or CPPO activity, and are potentially herbicides of future commercial interest. The inhibitors are used as herbicides to suppress the growth of undesirable vegetation in fields where crops are grown, particularly agronomically important crops such as maize and other cereal crops such as wheat, oats, rye, sorghum, rice, barley, millet, turf and forage grasses, and the like, as well as cotton, sugar cane, sugar beet, oilseed rape, and soybeans.

Thus, an assay useful for identifying inhibitors of essential plant genes, such as plant ENR-A, CBL, UROD, PBGD, or CPPO genes, comprises the steps of:
a) reacting a plant ENR-A, CBL, UROD, PBGD, or CPPO enzyme, and a substrate thereof in the presence of a suspected inhibitor of the enzyme's function;
b) comparing the rate of enzymatic activity in the presence of the suspected inhibitor to the rate of enzymatic activity under the same conditions in the absence of the suspected inhibitor; and
c) determining whether the suspected inhibitor inhibits the ENR-A, CBL, UROD, PBGD, or CPPO enzyme, respectively.

For example, the inhibitory effect on plant ENR-A, CBL, UROD, PBGD, or CPPO may be determined by a reduction or complete inhibition of ENR-A, CBL, UROD, PBGD, or CPPO activity in the assay. Such a determination may be made by comparing, in the presence and absence of the candidate inhibitor, the amount of substrate used or intermediate or product made during the reaction.

The present invention further embodies plants, plant tissues, plant seeds, and plant cells that have modified ENR-A, CBL, UROD, PBGD, or CPPO activity, and that are therefore tolerant to inhibition by a chemical at levels normally inhibitory to naturally occurring ENR-A, CBL, UROD, PBGD, or CPPO enzyme activity, respectively. Herbicide tolerant plants encompassed by the invention include those that would otherwise be potential targets for normally inhibiting herbicides, particularly the agronomically important crops mentioned above. According to one aspect of this embodiment, plants, plant tissue, plant seeds, or plant cells are stably transformed with a recombinant DNA molecule comprising a suitable promoter functional in plants operatively linked to a nucleotide sequence that encodes an enzyme having modified ENR-A, CBL, UROD, PBGD, or CPPO activity, that is tolerant to a concentration of a ENR-A, CBL, UROD, PBGD, or CPPO inhibitor, respectively, that would normally inhibit the activity of wild-type, unmodified ENR-A, CBL, UROD, PBGD, or CPPO, in the plant. Modified ENR-A, CBL, UROD, PBGD, or CPPO activity, may also be conferred upon a plant by increasing expression of wild-type (i.e. sensitive) ENR-A, CBL, UROD, PBGD, or CPPO enzyme, by providing multiple copies of wild-type ENR-A, CBL, UROD, PBGD, or CPPO genes, to the plant or by overexpression of the endogenous wild-type ENR-A, CBL, UROD, PBGD, or CPPO gene, or genes, under control of a stronger-than-wild-type promoter (e.g. either a promoter that drives expression at a higher rate, or a promoter that drives expression for a longer duration). The transgenic plants, plant tissue, plant seeds, or plant cells thus created are then selected by conventional selection techniques, whereby inhibitor tolerant descendants (lines) are isolated, characterized, and developed. Alternately, random or site-specific mutagenesis may be used to generate ENR-A, CBL, UROD, PBGD, or CPPO inhibitor, tolerant lines. Still further, inhibitor tolerant lines can be developed via selection of natural variants.

Therefore, the present invention provides a plant, plant cell, plant seed, or plant tissue comprising a DNA molecule comprising a nucleotide sequence, preferably isolated from a plant, that encodes an enzyme having ENR-A, CBL, UROD, PBGD, or CPPO activity, and wherein the DNA molecule confers upon the plant, plant cell, plant seed, or plant tissue tolerance to a ENR-A, CBL, UROD, PBGD, or CPPO inhibitor, in amounts that normally naturally occurring ENR-A, CBL, UROD, PBGD, or CPPO activity. According to one example of this embodiment, the enzyme comprises an amino acid sequence substantially similar to any one of the amino acid sequence set forth in SEQ ID NO:2, SEQ ID NO:4, SEQ ID NO:6, SEQ ID NO:8, or SEQ ID NO:10. According to another example of this embodiment, the DNA molecule is substantially similar to any one of the coding sequence set forth in SEQ ID NO:1, SEQ ID NO:3, SEQ ID NO:5, SEQ ID NO:7, or SEQ ID NO:9. In a related aspect, the present invention is directed to a method for selectively suppressing the growth of weeds in a field containing a crop of planted crop seeds or plants, comprising applying to crops or crop seeds that are tolerant to an inhibitor that inhibits naturally occurring ENR-A, CBL, UROD, PBGD, or CPPO activity, and the weeds in the field an ENR-A, CBL, UROD, PBGD, or CPPO inhibitor, respectively, in amounts that inhibit naturally occurring ENR-A, CBL, UROD, PBGD, or CPPO activity, respectively, wherein the inhibitor suppresses the growth of the weeds without significantly suppressing the growth of the crops.

Other objects and advantages of the present invention will become apparent to those skilled in the art from a study of the following description of the invention and non-limiting examples.

The invention thus provides:

An isolated DNA molecule comprising a nucleotide sequence substantially similar to any one of SEQ ID NO:1, SEQ ID NO:3, SEQ ID NO:5, SEQ ID NO:7, or SEQ ID NO:9. In a preferred embodiment, the nucleotide sequence encodes an amino acid sequence substantially similar to any one of SEQ ID NO:2, SEQ ID NO:4, SEQ ID NO:6, SEQ ID NO:8, or SEQ ID NO:10. In another preferred embodiment, the nucleotide sequence is SEQ ID NO:1, SEQ ID NO:3, SEQ ID NO:5, SEQ ID NO:7, or SEQ ID NO:9. In yet another preferred embodiment, the nucleotide sequence encodes the amino acid sequence of SEQ ID NO:2, SEQ ID NO:4, SEQ ID NO:6, SEQ ID NO:8, or SEQ ID NO:10. Preferably, the nucleotide sequence is a plant nucleotide sequence, which preferably encodes a polypeptide having ENR-A, CBL, UROD, PBGD, or CPPO activity.

The invention further provides:

A polypeptide comprising an amino acid sequence encoded by a nucleotide sequence substantially similar to any one of SEQ ID NO:1, SEQ ID NO:3, SEQ ID NO:5, SEQ ID NO:7, or SEQ ID NO:9 . Preferably, the amino acid sequence is encoded by SEQ ID NO:1, SEQ ID NO:3, SEQ ID NO:5, SEQ ID NO:7, or SEQ ID NO:9. Preferably, the polypeptide comprises an amino acid sequence substantially similar to any one of SEQ ID NO:2, SEQ ID NO:4, SEQ ID NO:6, SEQ ID NO:8, or SEQ ID NO:10. Preferably the amino acid sequence is SEQ ID NO:2, SEQ ID NO:4, SEQ ID NO:6, SEQ ID NO:8, or SEQ ID NO:10. The amino acid sequence preferably has ENR-A, CBL, UROD, PBGD, or CPPO activity. In another preferred embodiment, the amino acid sequence comprises at least 20 consecutive amino acid residues of the amino acid sequence encoded by any one of SEQ ID NO:1, SEQ ID NO:3, SEQ ID NO:5, SEQ ID NO:7, or SEQ ID NO:9. Or, alternatively, the amino acid sequence comprises at least 20 consecutive amino acid residues of the amino acid sequence of any one of SEQ ID NO:2, SEQ ID NO:4, SEQ ID NO:6, SEQ ID NO:8, or SEQ ID NO:10.

The invention further provides:

An expression cassette comprising a promoter operatively linked to a DNA molecule according to the present invention, wherein the promoter is preferably functional in a eukaryote, wherein the promoter is preferably heterologous to the DNA molecule. The present invention further provides recombinant vector comprising an expression cassette according to the present invention, wherein said vector is preferably capable of being stably transformed into a host cell, a host cell comprising a DNA molecule according to the present invention, wherein said DNA molecule is preferably expressible in the cell. The host cell is preferably selected from the group consisting of an insect cell, a yeast cell, a prokaryotic cell and a plant cell. The invention further provides a plant or seed comprising a plant cell of the present invention, wherein the plant or seed is preferably tolerant to an inhibitor of ENR-A, CBL, UROD, PBGD, or CPPO activity.

The invention further provides:

A process for making nucleotides sequences encoding gene products having altered ENR-A, CBL, UROD, PBGD, or CPPO activity, comprising: a) shuffling an unmodified nucleotide sequence of the present invention, b) expressing the resulting shuffled nucleotide sequences, and c) selecting for altered ENR-A, CBL, UROD, PBGD, or CPPO activity, as compared to the ENR-A, CBL, UROD, PBGD, or CPPO activity, respectively, of the gene product of said unmodified nucleotide sequence.

In a preferred embodiment, the unmodified nucleotide sequence is identical or substantially similar to any one of SEQ ID NO:1, SEQ ID NO:3, SEQ ID NO:5, SEQ ID NO:7, or SEQ ID NO:9, or a homolog thereof. The present invention further provides a DNA molecule comprising a shuffled nucleotide sequence obtainable by the process described above, a DNA molecule comprising a shuffled nucleotide sequence produced by the process described above. Preferably, a shuffled nucleotide sequence obtained by the process described above has enhanced tolerance to an inhibitor of ENR-A, CBL, UROD, PBGD, or CPPO activity. The invention further provides an expression cassette comprising a promoter operatively linked to a DNA molecule comprising a shuffled nucleotide sequence a recombinant vector comprising such an expression cassette, wherein said vector is preferably capable of being stably transformed into a host cell, a host cell comprising such an expression cassette, wherein said nucleotide sequence is preferably expressible in said cell. A preferred host cell is selected from the group consisting of an insect cell, a yeast cell, a prokaryotic cell and a plant cell. The invention further provides a plant or seed comprising such plant cell, wherein the plant is preferably tolerant to an inhibitor of ENR-A, CBL, UROD, PBGD, or CPPO activity, respectively.

The invention further provides:

A method for selecting compounds that interact with the protein encoded by SEQ ID NO:1, SEQ ID NO:3, SEQ ID NO:5, SEQ ID NO:7, or SEQ ID NO:9, comprising: a) expressing a DNA molecule comprising SEQ ID NO:1, SEQ ID NO:3, SEQ ID NO:5, SEQ ID NO:7, or SEQ ID NO:9, or a sequence substantially similar to SEQ ID NO:1, SEQ ID NO:3, SEQ ID NO:5, SEQ ID NO:7, or SEQ ID NO:9, or a homolog thereof, to generate the corresponding protein, b) testing a compound suspected of having the ability to interact with the protein expressed in step (a), and c) selecting compounds that interact with the protein in step (b).

The invention further provides:

A process of identifying an inhibitor of ENR-A, CBL, UROD, PBGD, or CPPO activity, comprising: a) introducing a DNA molecule comprising a nucleotide sequence of SEQ ID NO:1, SEQ ID NO:3, SEQ ID NO:5, SEQ ID NO:7, or SEQ ID NO:9, and having ENR-A, CBL, UROD, PBGD, or CPPO activity, or nucleotide sequences substantially similar thereto, or a homolog thereof, into a plant cell, such that said sequence is functionally expressible at levels that are higher than wild-type expression levels, b) combining said plant cell with a compound to be tested for the ability to inhibit the ENR-A, CBL, UROD, PBGD, or CPPO activity, respectively, under conditions conducive to such inhibition, c) measuring plant cell growth under the conditions of step (b), d) comparing the growth of said plant cell with the growth of a plant cell having unaltered ENR-A, CBL, UROD, PBGD, or CPPO activity, respectively, under identical conditions, and e) selecting said compound that inhibits plant cell growth in step (d).

The invention further comprises a compound having herbicidal activity identifiable according to the process described immediately above.

The invention further comprises:

A process of identifying compounds having herbicidal activity comprising: a) combining a protein of the present invention and a compound to be tested for the ability to interact with said protein, under conditions conducive to interaction, b) selecting a compound identified in step (a) that is capable of interacting with said protein, c) applying identified compound in step (b) to a plant to test for herbicidal activity, and d) selecting compounds having herbicidal activity.

The invention further comprises a compound having herbicidal activity identifiable according to the process described immediately above.

The invention further comprises:

A method for suppressing the growth of a plant comprising, applying to said plant a compound that inhibits the activity of a polypeptide of the present invention in an amount sufficient to suppress the growth of said plant.

The invention further comprises:

A method for recombinantly expressing a protein having ENR-A, CBL, UROD, PBGD, or CPPO activity comprising introducing a nucleotide sequence encoding a protein having one of the above activities into a host cell and expressing the nucleotide sequence in the host cell. A preferred host cell is selected from the group consisting of an insect cell, a yeast cell, a prokaryotic cell and a plant cell. A preferred prokaryotic cell is a bacterial cell, e.g. *E. coli*.

BRIEF DESCRIPTION OF THE SEQUENCES IN THE SEQUENCE LISTING

SEQ ID NO:1 is a cDNA sequence encoding ENR-A from *Arabidopsis thaliana*.

SEQ ID NO:2 is the predicted amino acid sequence of *Arabidopsis thaliana* ENR-A encoded by SEQ ID NO:1.

SEQ ID NO:3 is cDNA coding sequence for the CBL gene from *Arabidopsis thaliana*.

SEQ ID NO:4 amino acid sequence encoded by the *Arabidopsis thaliana* CBL sequence shown in SEQ ID NO:3.

SEQ ID NO:5 is a cDNA sequence encoding UROD from *Arabidopsis thaliana*.

SEQ ID NO:6 is the predicted amino acid sequence of *Arabidopsis thaliana* UROD encoded by SEQ ID NO:5.

SEQ ID NO:7 is a cDNA sequence encoding PBGD from *Arabidopsis thaliana*.

SEQ ID NO:8 is the predicted amino acid sequence of *Arabidopsis thaliana* PBGD encoded by SEQ ID NO:7.

SEQ ID NO:9 is a cDNA sequence encoding CPPO from *Arabidopsis thaliana*.

SEQ ID NO:10 is the predicted amino acid sequence of *Arabidopsis thaliana* CPPO encoded by SEQ ID NO:9.

SEQ ID NO:11 is the genomic sequence of the ENR-A gene from *Arabidopsis thaliana*.

SEQ ID NO:12 is the oligonucleotide ENR-A-F2

SEQ ID NO:13 is the oligonucleotide ENR-A-R2

SEQ ID NO:14 is the sequence for oligonucleotide DG354.

SEQ ID NO:15 is the sequence for oligonucleotide DG357.

SEQ ID NO:16 is the sequence for oligonucleotide CBL1

SEQ ID NO:17 is the sequence for oligonucleotide CBL2.

SEQ ID NO:18 is the sequence for oligonucleotide CBL3.

SEQ ID NO:19 is the sequence for oligonucleotide ASV1.

SEQ ID NO:20 is the sequence for oligonucleotide ASV2.

SEQ ID NO:21 is the genomic sequence of *Arabidopsis thaliana* UROD

SEQ ID NO:22 is the sequence for oligonucleotide UROD-N-Nde

SEQ ID NO:23 is the sequence for oligonucleotide UROD-C-Not

SEQ ID NO:24 is the sequence for oligonucleotide UROD-F2

SEQ ID NO:25 is the sequence for oligonucleotide UROD-R2

SEQ ID NO:26 is the genomic sequence of *Arabidopsis thaliana* PBGD.

SEQ ID NO:27 is the sequence for oligonucleotide PORD-F2.

SEQ ID NO:28 is the sequence for oligonucleotide PORD-R2.

SEQ ID NO:29 is the genomic sequence of the CPPO gene from *Arabidopsis thaliana*.

SEQ ID NO:30 is the sequence for oligonucleotide CR73.

SEQ ID NO:31 is the sequence for oligonucleotide CR75.

SEQ ID NO:32 is the sequence for oligonucleotide JG-L.

SEQ ID NO:33 is the sequence for oligonucleotide CPPGO-F2.

SEQ ID NO:34 is the sequence for oligonucleotide CPPGO-R2.

DEFINITIONS

For clarity, certain terms used in the specification are defined and used as follows:

Activatable DNA Sequence: a DNA sequence that regulates the expression of genes in a genome, desirably the genome of a plant. The activatable DNA sequence is complementary to a target gene endogenous in the genome, in this case the gene encoding ENR-A, CBL, UROD, PBGD, or CPPO. When the activatable DNA sequence is introduced and expressed in a cell, it inhibits expression of the target gene. An activatable DNA sequence useful in conjunction with the present invention includes those encoding or acting as dominant inhibitors, such as a translatable or untranslatable sense sequence capable of disrupting gene function in stably transformed plants to positively identify one or more genes essential for normal growth and development of a plant. A preferred activatable DNA sequence is an antisense DNA sequence. The interaction of the antisense sequence and the target gene results in substantial inhibition of the expression of the target gene so as to kill the plant, or at least inhibit normal plant growth or development.

Activatable DNA Construct: a recombinant DNA construct comprising a synthetic promoter operatively linked to the activatable DNA sequence, which when introduced into a cell, desirably a plant cell, is not expressed, i.e. is silent, unless a complete hybrid transcription factor capable of binding to and activating the synthetic promoter is present. The activatable DNA construct is introduced into cells, tissues, or plants to form stable transgenic lines capable of expressing the activatable DNA sequence.

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Co-factor: natural reactant, such as an organic molecule or a metal ion, required in an enzyme-catalyzed reaction. A co-factor is e.g. NAD(P), riboflavin (including FAD and FMN), folate, molybdopterin, thiamin, biotin, lipoic acid, pantothenic acid and coenzyme A, S-adenosylmethionine, pyridoxal phosphate, ubiquinone, menaquinone. Optionally, a co-factor can be regenerated and reused.

Complementary: "Complementary" refers to two nucleotide sequences which comprise antiparallel nucleotide sequences capable of pairing with one another upon formation of hydrogen bonds between the complementary base residues in the antiparallel nucleotide sequences.

DNA shuffling: DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Enzyme activity: means herein the ability of an enzyme to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Essential: An "essential" gene is a gene encoding a protein such as e.g. a biosynthetic enzyme, receptor, signal transduction protein, structural gene product, or transport protein that is essential to the growth or survival of the plant.

Expression cassette: "Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue or organ or stage of development. In the case of a plastid expression cassette, for expression of the nucleotide sequence from a plastid genome, additional elements, i.e. ribosome binding sites, may be required.

Herbicide: a chemical substance used to kill or suppress the growth of plants, plant cells, plant seeds, or plant tissues.

Heterologous DNA Sequence: a DNA sequence not naturally associated with a host cell into which it is introduced, including non-naturally occurring multiple copies of a naturally occurring DNA sequence.

Homologous DNA Sequence: a DNA sequence naturally associated with a host cell.

Inhibitor: a chemical substance that inactivates the enzymatic activity of ENR-A, CBL, UROD, PBGD, or CPPO. The term "herbicide" is used herein to define an inhibitor when applied to plants, plant cells, plant seeds, or plant tissues.

Isogenic: plants which are genetically identical, except that they may differ by the presence or absence of a heterologous DNA sequence.

Isolated: in the context of the present invention, an isolated DNA molecule or an isolated enzyme is a DNA molecule or enzyme which, by the hand of man, exists apart from its native environment and is therefore not a product of nature. An isolated DNA molecule or enzyme may exist in a purified form or may exist in a non-native environment such as, for example, in a transgenic host cell.

Mature protein: protein which is normally targeted to a cellular organelle, such as a chloroplast, and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in a plant (i.e. enzyme activity that occurs naturally in the absence of direct or indirect manipulation of such activity by man), which is tolerant to inhibitors that inhibit the naturally occurring enzyme activity.

Native: A "native" refers to a gene which is present in the genome of the untransformed plant cell.

Plant: A "plant" refers to any plant or part of a plant at any stage of development. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

With respect to CBL, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least 65%, more desirably at least 75%, preferably at least 85%, more preferably at least 90%, still more preferably at least 95%, yet still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "CBL gene" refers to a DNA molecule comprising SEQ ID NO:3 or comprising a nucleotide sequence substantially similar to SEQ ID NO:3. Homologs of the CBL gene include nucleotide sequences that encode an amino acid sequence that is at least 30% identical to SEQ ID NO:4 as measured, using the parameters described below, wherein the amino acid sequence encoded by the homolog has the biological activity of the CBL protein.

With respect to CBL, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is at least 65%, more desirably at least 75%, preferably at least 85%, more preferably at least 90%, still more preferably at least 95%, yet still more preferably at least 99%, using default BLAST analysis parameters. As used herein the term "CBL protein" refers to an amino acid sequence encoded by a DNA molecule comprising a nucleotide sequence substantially similar to SEQ ID NO:3. Homologs of the CBL protein are amino acid sequences that are at least 30% identical to SEQ ID NO:4, as measured using the parameters described above, wherein the amino acid sequence encoded by the homolog has the biological activity of the CBL protein.

With respect to UROD, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. Preferably, "substantially similar" refers to nucleotide sequences that encode a protein having at least 85% identity to SEQ ID NO:6, wherein said protein sequence comparisons are conducted using GAP analysis as described below. A nucleotide sequence "substantially similar" to the reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NapO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "UROD gene" refers to a DNA molecule comprising SEQ ID NO:5 or comprising a nucleotide sequence substantially similar to SEQ ID NO:5. Homologs of the UROD gene include nucleotide sequences that encode an amino acid sequence that is at least 30% identical to SEQ ID NO:6 as measured, using the parameters described below, wherein the amino acid sequence encoded by the homolog has the biological activity of the UROD protein. Preferable are dicot homologs.

With respect to UROD, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is preferably at least 85%, more preferably at least 90%, still more preferably at least 95%, yet still more preferably at least 99%, using default GAP analysis parameters with the University of Wisconsin GCG, SEQWEB application of GAP, based on the algorithm of Needleman and Wunsch (Needleman and Wunsch (1970) J Mol. Biol. 48: 443–453). As used herein the term "UROD protein" refers to an amino acid sequence encoded by a DNA molecule comprising a nucleotide sequence substantially similar to SEQ ID NO:5. Homologs of the UROD protein are amino acid sequences that are at least 30% identical to SEQ ID NO:6, as measured using the parameters described above, wherein the amino acid sequence encoded by the homolog has the biological activity of the UROD protein. Preferable are dicot homologs.

With respect to PBGD, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. Preferably, "substantially similar" refers to nucleotide sequences that encode a protein having at least 85% identity to SEQ ID NO:8, wherein said protein sequence comparisons are conducted using GAP analysis as described below. A nucleotide sequence "substantially similar" to the reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "PBGD gene" refers to a DNA molecule comprising SEQ ID NO:7 or comprising a nucleotide sequence substantially similar to SEQ ID NO:7. Homologs of the PBGD gene include nucleotide sequences that encode an amino acid sequence that is at least 30% identical to SEQ ID NO:8 as measured, using the parameters described below, wherein the amino acid sequence encoded by the homolog has the biological activity of the PBGD protein. Preferable are dicot homologs.

With respect to PBGD, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is preferably at least 85%, more preferably at least 90%, still more preferably at least 95%, yet still more preferably at least 99%, using default GAP analysis parameters with the University of Wisconsin GCG, SEQWEB application of GAP, based on the algorithm of Needleman and Wunsch (Needleman and Wunsch (1970) J Mol. Biol. 48: 443–453). As used herein the term "PBGD protein" refers to an amino acid sequence encoded by a DNA molecule comprising a nucleotide sequence substantially similar to SEQ ID NO:7. Homologs of the PBGD protein are amino acid sequences that are at least 30% identical to SEQ ID NO:8, as measured using the parameters described above, wherein the amino acid sequence encoded by the homolog has the biological activity of the PBGD protein. Preferable are dicot homologs.

With respect to CPPO, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence. Desirably, the substantially similar nucleotide sequence encodes the polypeptide encoded by the reference nucleotide sequence. The term "substantially similar" is specifically intended to include nucleotide sequences wherein the sequence has been modified to optimize expression in particular cells. Preferably, "substantially similar" refers to nucleotide sequences that encode a protein having at least 81% identity, more preferably at least 85% identity, still more preferably at least 90% identity, still more preferably at least 95% identity, yet still more preferably at least 99% identity, to SEQ ID NO:10, wherein said protein sequence comparisons are conducted using GAP analysis as described below. Also, "substantially similar" preferably also refers to nucleotide sequences having at least 75% identity, more preferably at least 80% identity, still more preferably at least 85% identity, still more preferably at least 90% identity, still more preferably 95% identity, yet still more preferably at least 99% identity, to SEQ ID NO:9, wherein said nucleotide sequence comparisons are conducted using GAP analysis as described below. A nucleotide sequence "substantially similar" to the reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C. more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "CPPO gene" refers to a DNA molecule comprising SEQ ID NO:9 or comprising a nucleotide sequence substantially similar to SEQ ID NO:9. Homologs of the CPPO gene include nucleotide sequences that encode an amino acid sequence that is at least 50% identical to SEQ ID NO:10, more preferably at least 60% identical, still more preferably at least 65% identical, still more preferably at least 70%, yet still more preferably at least 80%, as measured, using the parameters described below, wherein the amino acid sequence encoded by the homolog has the biological activity of the CPPO protein.

With respect to CPPO, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is preferably at least 81%, more preferably at least 85%, still more preferably at least 90%, more preferably at least 95%, still more preferably at least 99% using default GAP analysis parameters with the University of Wisconsin GCG (version 10), SEQWEB application of GAP, based on the algorithm of Needleman and Wunsch (Needleman and Wunsch (1970) J Mol. Biol. 48: 443–453). As used herein the term "CPPO protein" refers to an amino acid sequence encoded by a DNA molecule comprising a nucleotide sequence substantially similar to SEQ ID NO:9. Homologs of the CPPO protein are amino acid sequences that are at least 50% identical to SEQ ID NO:10, as measured using the parameters described above, wherein the amino acid sequence encoded by the homolog has the biological activity of the CPPO protein.

With respect to ENR-A, in its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence. Desirably, the substantially similar nucleotide sequence encodes the polypeptide encoded by the reference nucleotide sequence. The term "substantially similar" is specifically intended to include nucleotide sequences wherein the sequence has been modified to optimize expression in particular cells. Preferably, "substantially similar" refers to nucleotide sequences that encode a protein having at least 90% identity, more preferably at least 95% identity, yet still more preferably at least 99% identity, to SEQ ID NO:2, wherein said protein sequence comparisons are conducted using GAP analysis as described below. Also, "substantially similar" preferably also refers to nucleotide sequences having at least 85% identity, more preferably at least 90% identity, still more preferably 95% identity, yet still more preferably at least 99% identity, to SEQ ID NO:1, wherein said nucleotide sequence comparisons are conducted using GAP analysis as described below. A nucleotide sequence "substantially similar" to the reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C. As used herein the term "ENR-A gene" refers to a DNA molecule comprising SEQ ID NO:1 or comprising a nucleotide sequence substantially similar to SEQ ID NO:1. Homologs of the ENR-A gene include nucleotide sequences that encode an amino acid sequence that is at least 30% identical to SEQ ID NO:2, more preferably at least 70%, still more preferably at least 85%, yet still more preferably at least 90%, as measured, using the parameters described below, wherein the amino acid sequence encoded by the homolog has the biological activity of the ENR-A protein.

With respect to ENR-A, the term "substantially similar", when used herein with respect to a protein, means a protein corresponding to a reference protein, wherein the protein has substantially the same structure and function as the reference protein, e.g. where only changes in amino acids sequence not affecting the polypeptide function occur. When used for a protein or an amino acid sequence the percentage of identity between the substantially similar and the reference protein or amino acid sequence desirably is preferably at least 90%, more preferably at least 95%, still more preferably at least 99% using default GAP analysis parameters with the University of Wisconsin GCG (version 10), SEQWEB application of GAP, based on the algorithm of Needleman and Wunsch (Needleman and Wunsch (1970) J Mol. Biol. 48: 443–453). As used herein the term "ENR-A protein" refers to an amino acid sequence encoded by a DNA molecule comprising a nucleotide sequence substantially similar to SEQ ID NO:1. Homologs of the ENR-A protein are amino acid sequences that are at least 30% identical to SEQ ID NO:2, as measured using the parameters described above, wherein the amino acid sequence encoded by the homolog has the biological activity of the ENR-A protein.

Substrate: a substrate is the molecule that an enzyme naturally recognizes and converts to a product in the biochemical pathway in which the enzyme naturally carries out its function, or is a modified version of the molecule, which is also recognized by the enzyme and is converted by the enzyme to a product in an enzymatic reaction similar to the naturally-occurring reaction.

Target gene: A "target gene" is any gene in a plant cell. For example, a target gene is a gene of known function or is a gene whose function is unknown, but whose total or partial nucleotide sequence is known. Alternatively, the function of a target gene and its nucleotide sequence are both unknown. A target gene is a native gene of the plant cell or is a heterologous gene which had previously been introduced into the plant cell or a parent cell of said plant cell, for example by genetic transformation. A heterologous target gene is stably integrated in the genome of the plant cell or is present in the plant cell as an extrachromosomal molecule, e.g. as an autonomously replicating extrachromosomal molecule.

Tolerance: the ability to continue essentially normal growth or function (i.e. no more than 5% of herbicide tolerant plants show phytotoxicity) when exposed to an inhibitor or herbicide in an amount sufficient to suppress the normal growth or function of native, unmodified plants.

Transformation: a process for introducing heterologous DNA into a cell, tissue, or plant. Transformed cells, tissues, or plants are understood to encompass not only the end product of a transformation process, but also transgenic progeny thereof.

Transgenic: stably transformed with a recombinant DNA molecule that preferably comprises a suitable promoter operatively linked to a DNA sequence of interest.

DETAILED DESCRIPTION OF THE INVENTION

I. Plant ENR-A, CBL, UROD, PBGD, or CPPO Genes, Respectively

In the present invention, the following abbreviations are used for the above plant genes. ENR-A is the abbreviation for enoyl-acyl carrier protein reductase; CBL is the abbreviation for cystathionine beta lyase; UROD is the abbreviation for uroporphyrinogen decarboxylase; PBGD is the abbreviation for porphobilinogen deaminase; and CPPO is the abbreviation for coproporphyrinogen oxidase.

CBL (EC 4.4.1.8) is an enzyme catalyzing a biochemical reaction required for the biosynthesis of the amino acid methionine. The methionine biosynthetic pathway in plants is outlined in FIG. 1 of Ravenel et al., (1998) *Proc. Natl. Acad. Sci. USA* 95:7805–7812, incorporated herein by reference. This enzyme catalyzes the conversion of cystathionine to homocysteine by cleaving cystathionine to produce homocysteine, pyruvate, and ammonia. The sequence of a cDNA for the Arabidopsis CBL gene has been identified (EMBL accession #L40511; Ravanel et al. (1995) *Plant Mol. Biol.* 29: 875–882). The CBL gene has been cloned from other organisms, including *E. coli* (SWISS PROT accession #P06721), *S. typhimurium* (PIR accession #JV0020), *S. cerevisiae* (SWISS PROT accession #P43623), *B. subtilis* (GenPept accession #Z99110 AL009126), *Emericella nidulans* (GenPept accession #U28383),and human (GenPept accession #S52784). Results from GAP analysis of the above sequences show the following identities relative to *Arabidopsis thaliana*: *E. coli* (28% identical); *S. cerevisiae* (28% identical); humans (41% identical); *B. subtilis* (46% identical), and *Emericella nidulans* (47% identical).

UROD (EC 4.1.1.37) is an enzyme catalyzing a biochemical reaction required for the biosynthesis of porphyrin and heme. The porphyrin biosynthetic pathway in plants is outlined in FIG. 1 of Reinbothe & Reinbothe, *Plant Physiol.* 111:1–7 (1996), incorporated herein by reference. This enzyme catalyzes the conversion of uroporphyrinogen III to coproporphyrinogen III. Coproporphyrinogen III is synthesized by plants, microorganisms, and animals as a precursor for the production of porphyrin and heme. In most organisms, heme is required as a prosthetic group for many enzymes, e.g. cytochrome oxidase. In plants, the porphyrin pathway produces chlorophyll (reviewed in Suzuki et al., *Annu. Rev. Genet.* 31:61–89 (1997) and Reinbothe & Reinbothe, *Plant Physiol.* 111:1–7 (1996). The UROD gene has been cloned from many organisms, including *E. coli* (SWISS PROT accession #P29680), *S. cerevisiae* (SWISS PROT accession #P32347), humans (SWISS PROT accession #P06132), maize (SWISS PROT accession #O081220), and tobacco (SWISS PROT accession #Q42967).

PBGD (also known as hydroxymethylbilane synthase or preuroporphyrinogen synthase) (EC 4.3.1.8) is an enzyme catalyzing a biochemical reaction required for the biosynthesis of porphyrin and heme. The porphyrin biosynthetic pathway in plants is outlined in FIG. 1 of Reinbothe & Reinbothe, *Plant Physiol.* 111:1–7 (1996), incorporated herein by reference. This enzyme catalyzes the condensation of four molecules of porphobilinogen to form hydroxymethylbilane. Hydroxymethylbilane is synthesized by plants, microorganisms, and animals as a precursor for the production of porphyrin and heme. In most organisms, heme is required as a prosthetic group for many enzymes, e.g. cytochrome oxidase. In plants, the porphyrin pathway produces chlorophyll (reviewed in Suzuki et al., *Annu. Rev. Genet.* 31:61–89 (1997) and Reinbothe & Reinbothe, *Plant Physiol.* 111:1–7 (1996). The PBGD gene has been cloned from many organisms, including *E. coli* (SWISS PROT accession #P06983), *S. cerevisiae* (SWISS PROT accession #P28789), humans (SWISS PROT accession #P08397), pea (SWISS PROT accession #Q43082), *Methanococcus jannaschii* (SWISS PROT accession #Q57989), and *Arabidopsis thaliana* (SWISS PROT accession #Q43316) (Lim et al., *Plant Mol. Biol.* 26:863–872 (1994)). Results from GAP analysis of the above sequences show the following identities relative to *Arabidopsis thaliana: E. coli* (45% identical); *S. cerevisiae* (35% identical); humans (37% identical); pea (78% identical), and *Methanococcus jannaschii* (41% identical).

CPPO (EC 1.3.3.3) is an enzyme catalyzing a biochemical reaction required for the biosynthesis of porphyrin and heme. The porphyrin biosynthetic pathway in plants is outlined in FIG. 1 of Reinbothe & Reinbothe, *Plant Physiol.* 111:1–7 (1996), incorporated herein by reference. This enzyme catalyzes the conversion of coproporphyrinogen III to protoporphyrinogen IX. Protoporphyrinogen IX is synthesized by plants, microorganisms, and animals as a precursor for the production of porphyrin and heme. In most organisms, heme is required as a prosthetic group for many enzymes, e.g. cytochrome oxidase. In plants, the porphyrin pathway produces chlorophyll (reviewed in Suzuki et al., *Annu. Rev. Genet.* 31:61–89 (1997) and Reinbothe & Reinbothe, *Plant Physiol.* 111:1–7 (1996). The CPPO gene has been cloned from many organisms, including *E. coli*, aerobic form (SWISS PROT accession #P36553), *S. cerevisiae* (SWISS PROT accession #P11353), humans (SWISS PROT accession #P36551), barley (SWISS PROT accession #Q42480), tobacco (SWISS PROT accession #Q42946), and soybean (SWISS PROT accession #P35055). Results from GAP analysis of the above sequences show the following identities at the amino acid level relative to *Arabidopsis thaliana: E. coli*, aerobic form (48% identical), *S. cerevisiae* (52% identical), humans (53% identical), barley (75% identical), tobacco (79% identical), and soybean (80% identical), and the following identities at the nucleotide level relative to *Arabidopsis thaliana:* barley (65% identical), soybean (73% identical).

ENR-A, also known as NADH enoyl-ACP reductase, (EC 1.3.1.9) is an enzyme catalyzing a biochemical reaction required for the final reducing step in the fatty acid biosynthesis cycle. The fatty acid biosynthetic pathway in plants is outlined in FIG. 6.6 of Dey & Harborne, *Plant Biochemistry, Academic Press* (1997) incorporated herein by reference. This enzyme catalyzes the reduction of enoyl-acyl-ACP derivatives of carbon chain length from 4 to 16, by reducing a trans-unsaturated double bond to produce a saturated acyl-ACP, which can be elongated in the next condensation reaction. In plants, fatty acids act as energy stores, membrane constituents, and play key roles in metabolic control via second messenger signaling. The ENR-A gene has been cloned from many organisms, including *E. coli* (SWISS PROT accession #P29132), Petunia (GenBank accession #CAA05879), rice (GenBank accession #CAA05816), *Arabidopsis thaliana* (GenBank accession #CAA74175), and rape (SWISS PROT accession #P80030). Results from GAP analysis of the above sequences show the following identities at the amino acid level relative to *Arabidopsis thaliana: E. coli* (34% identical), Petunia (71% identical), rice (73% identical), and rape (90% identical), and the following identities at the nucleotide level relative to *Arabidopsis thaliana:* rape (85% identical). The sequences controlling the expression of the *Arabidopsis thaliana* enr-A gene have been described (de Boer, G. -J. et. al. (1999) Plant Mol. Biol. 39:1197–1207). The corresponding *E. coli* gene, FabI, has been shown to be inhibited by triclosan, an antimicrobial biocide (Heath, R. J. et al. (1999) J. Biol. Chem. 274:11110–11114).

In one aspect, the present invention is directed to a DNA molecule comprising a nucleotide sequence isolated from a plant source that encodes ENR-A, CBL, UROD, PBGD, or CPPO. In particular, the present invention provides a DNA molecule isolated from *Arabidopsis thaliana* that encodes ENR-A, CBL, UROD, PBGD, or CPPO, and DNA molecules substantially similar thereto that encode enzymes having ENR-A, CBL, UROD, PBGD, or CPPO activity, respectively. The DNA coding sequence for ENR-A, CBL, UROD, PBGD, or CPPO, from *Arabidopsis thaliana* is provided in SEQ ID NO:1, SEQ ID NO:3, SEQ ID NO:5, SEQ ID NO:7, or SEQ ID NO:9, respectively. The DNA sequence of the genomic sequence of the UROD, PBGD, CPPO, or ENR-A gene, from *Arabidopsis thaliana* is set forth in SEQ ID NO:21, SEQ ID NO:26, SEQ ID NO:29, or SEQ ID NO: 11, respectively.

Based on Applicants' disclosure of the present invention, ENR-A, CBL, UROD, PBGD, or CPPO homologs, i.e. DNA sequences encoding ENR-A, CBL, UROD, PBGD, or CPPO enzymes, respectively, are isolated from the genome of any desired plant.

Alternatively, ENR-A, CBL, UROD, PBGD, or CPPO gene sequences, can be isolated from any plant according to well known techniques based on their sequence similarity to the *Arabidopsis thaliana* coding sequences (SEQ ID NO:1, SEQ ID NO:3, SEQ ID NO:5, SEQ ID NO:7, or SEQ ID NO:9, respectively) taught by the present invention. In these techniques, all or part of a known ENR-A, CBL, UROD, PBGD, or CPPO gene's coding sequence, respectively, is used as a probe that selectively hybridizes to other ENR-A, CBL, UROD, PBGD, or CPPO gene sequences, present in a population of cloned genomic DNA fragments or cDNA fragments (i.e. genomic or cDNA libraries) from a chosen source organism. Such techniques include hybridization screening of plated DNA libraries (either plaques or colonies; see, e.g. Sambrook et al., "Molecular Cloning", eds., Cold Spring Harbor Laboratory Press. (1989)) and amplification by PCR using oligonucleotide primers corresponding to sequence domains conserved among known ENR-A, CBL, UROD, PBGD, or CPPO enzyme's amino acid sequences, respectively (see, e.g. Innis et al., "PCR Protocols, a Guide to Methods and Applications", Academic Press (1990)). These methods are particularly well suited to the isolation of ENR-A, CBL, UROD, PBGD, or CPPO gene sequences, from organisms closely related to the organism from which the probe sequence is derived. The application of these methods using the Arabidopsis coding sequences as probes is well suited for the isolation of ENR-A, CBL, UROD, PBGD, or CPPO gene sequences, from any source organism, preferably other plant species, including monocotyledons and dicotyledons.

The isolated ENR-A, CBL, UROD, PBGD, or CPPO gene sequences, taught by the present invention the manipulated according to standard genetic engineering techniques to suit any desired purpose. For example, an entire plant ENR-A, CBL, UROD, PBGD, or CPPO gene sequence, or portions thereof may be used as a probe capable of specifically hybridizing to coding sequences and messenger RNAs. To achieve specific hybridization under a variety of conditions, such probes include, e.g. sequences that are unique among plant ENR-A, CBL, UROD, PBGD, or CPPO gene sequences, and are at least 10 nucleotides in length, preferably at least 20 nucleotides in length, and most preferably at least 50 nucleotides in length. Such probes are used to amplify and analyze ENR-A, CBL, UROD, PBGD, or CPPO gene sequences, respectively, from a chosen organism via PCR. This technique is useful to isolate additional plant ENR-A, CBL, UROD, PBGD, or CPPO gene sequences, respectively, from a desired organism or as a diagnostic assay to determine the presence of ENR-A, CBL, UROD, PBGD, or CPPO gene sequences, in an organism. This technique also is used to detect the presence of altered ENR-A, CBL, UROD, PBGD, or CPPO gene sequences, associated with a particular condition of interest such as herbicide tolerance, poor health, etc.

ENR-A, CBL, UROD, PBGD, or CPPO, specific hybridization probes also are used to map the location of these native genes in the genome of a chosen plant using standard techniques based on the selective hybridization of the probe to genomic sequences. These techniques include, but are not limited to, identification of DNA polymorphisms identified or contained within the probe sequence, and use of such polymorphisms to follow segregation of the gene relative to other markers of known map position in a mapping population derived from self fertilization of a hybrid of two polymorphic parental lines (see e.g. Helentaris et al., *Plant Mol. Biol.* 5: 109 (1985); Sommer et al. *Biotechniques* 12:82 (1992); D'Ovidio et al., *Plant Mol. Biol.* 15: 169 (1990)). While any plant ENR-A, CBL, UROD, PBGD, or CPPO gene sequence, is contemplated to be useful as a probe for mapping ENR-A, CBL, UROD, PBGD, or CPPO genes, respectively, preferred probes are those gene sequences from plant species more closely related to the chosen plant species, and most preferred probes are those gene sequences from the chosen plant species. Mapping of ENR-A, CBL, UROD, PBGD, or CPPO genes, in this manner is contemplated to be particularly useful for breeding purposes. For instance, by knowing the genetic map position of a mutant ENR-A, CBL, UROD, PBGD, or CPPO gene, that confers herbicide resistance, flanking DNA markers are identified from a reference genetic map (see, e.g., Helentjaris, *Trends Genet.* 3: 217 (1987)). During introgression of the herbicide resistance trait into a new breeding line, these markers are used to monitor the extent of linked flanking chromosomal DNA still present in the recurrent parent after each round of back-crossing.

ENR-A, CBL, UROD, PBGD, or CPPO, specific hybridization probes also are used to quantify levels of ENR-A, CBL, UROD, PBGD, or CPPO gene mRNA, respectively, in a plant using standard techniques such as Northern blot analysis. This technique is useful as a diagnostic assay to detect altered levels of ENR-A, CBL, UROD, PBGD, or CPPO gene expression, respectively, that are associated with particular conditions such as enhanced tolerance to herbicides that target ENR-A, CBL, UROD, PBGD, or CPPO genes.

II. Essentiality of ENR-A, CBL, UROD, PBGD, or CPPO Genes, in Plants Demonstrated by Antisense Inhibition As shown in the examples below, the essentiality of ENR-A, CBL, UROD, PBGD, or CPPO genes, for normal plant growth and development has been demonstrated by antisense inhibition of expression of the ENR-A, CBL, UROD, PBGD, or CPPO gene, respectively, in plants using the antisense validation system described in co-owned and co-pending application Ser. No. 09/199,025 entitled "Methods and Compositions Useful for the Activation of Silent Transgenes", filed Nov. 26, 1997, incorporated herein by reference. In this system, a hybrid transcription factor gene is made that comprises a DNA-binding domain and an activation domain. In addition, an activatable DNA construct is made that comprises a synthetic promoter operatively linked to an activatable DNA sequence. The hybrid transcription factor gene and synthetic promoter are selected such that the DNA binding domain of the hybrid transcription factor is capable of binding specifically to the synthetic promoter, which then activates expression of the activatable DNA sequence. A first plant is transformed with the hybrid transcription factor gene, and a second plant is transformed with the activatable DNA construct. The first plant and second plants are crossed to produce a progeny plant containing both the sequence encoding the hybrid transcription factor and the synthetic promoter, wherein the activatable DNA sequence is expressed in the progeny plant. In the preferred embodiment, the activatable DNA sequence is an antisense sequence capable of inactivating expression of ENR-A, CBL, UROD, PBGD, or CPPO, respectively. Hence, the progeny plant will be unable to normally express the endogenous gene.

This antisense validation system is especially useful for allowing expression of traits that might otherwise be unrecoverable as constitutively driven transgenes. For instance, foreign genes with potentially lethal effect or antisense genes or dominant-negative mutations designed to abolish function of essential genes, while of great interest in basic studies of plant biology, present inherent experimental problems. Decreased transformation frequencies are often cited as evidence of lethality associated with a particular constitutively driven transgene, but negative results of this type are laden with alternative trivial explanations. The antisense validation system is described in greater detail below:

A. Hybrid Transcription Factor Gene

A hybrid transcription factor gene for use in the antisense validation system described herein comprises DNA sequences encoding (1) a DNA-binding domain and (2) an activation domain that interacts with components of transcriptional machinery assembling at a promoter.

B. Activatable DNA Construct

An activatable DNA construct for use in the antisense validation system described herein comprises (1) a synthetic promoter operatively linked to (2) an activatable DNA sequence. The synthetic promoter comprises at least one DNA binding site recognized by the DNA binding domain of the hybrid transcription factor, and a minimal promoter, preferably a TATA element derived from a promoter recognized by plant cells. More particularly the TATA element is derived from a promoter recognized by the plant cell type into which the synthetic promoter will be incorporated. Desirably, the DNA binding site is repeated multiple times in the synthetic promoter so that the minimal promoter may be more effectively activated, such that the activatable DNA sequence associated with the synthetic promoter is more effectively expressed.

The activatable DNA sequence encompasses a DNA sequence, in this case ENR-A, CBL, UROD, PBGD, or CPPO, for which stable introduction and expression in a plant cell is desired. The activatable DNA sequence is operatively linked to the synthetic promoter to form the activatable DNA construct. The activatable DNA sequence in the activatable DNA construct is not expressed, i.e. is silent, in transgenic lines, unless a hybrid transcription factor capable of binding to and activating the synthetic promoter, is also present. The activatable DNA construct subsequently is introduced into cells, tissues or plants to form stable transgenic lines expressing the activatable DNA sequence, as described more fully below.

C. Transgenic Plants Containing the Hybrid Transcription Factor Gene or the Activatable DNA Construct The antisense validation system utilizes a first plant containing the hybrid transcription factor gene and a second plant containing the activatable DNA construct. The hybrid transcription factor genes and activatable DNA constructs described above are introduced into the plants by methods well known and routinely used in the art, including but not limited to crossing, Agrobacterium-mediated transformation, protoplast transformation, Ti plasmid vectors, direct DNA uptake such as microprojectile bombardment, liposome mediated uptake, microinjection, etc. Transformants are screened for the presence and functionality of the transgenes according to standard methods known to those skilled in the art.

D. Transgenic Plants Containing Both the Hybrid Transcription Factor Gene and the Activatable DNA Construct F1 plants containing both the hybrid transcription factor gene and the activatable DNA construct are generated by crossing said first and second plants and selected for the presence of an appropriate marker. In contrast to plants containing the activatable DNA construct alone, the F1 plants generate high levels of activatable DNA sequence expression product. Expression of ENR-A, CBL, UROD, PBGD, or CPPO antisense molecules, respectively, in such plants results in death or abnormal growth or development, indicating that ENR-A, CBL, UROD, PBGD, or CPPO, respectively, is essential for normal plant growth and development.

III. Recombinant Production of Plant ENR-A, CBL, UROD, PBGD, or CPPO Enzymes, and Uses Thereof For recombinant production of a plant ENR-A, CBL, UROD, PBGD, or CPPO enzyme, in a host organism, a ENR-A, CBL, UROD, PBGD, or CPPO coding sequence, respectively, preferably a plant coding sequence, is inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements operably linked in proper reading frame, is inserted into a vector capable of being transformed into the host cell. Suitable expression vectors and methods for recombinant production of proteins are well known for host organisms such as *E. coli,* yeast, and insect cells (see, e.g., Luckow and Summers, *Bio/Technol.* 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pV111392/Sf21 cells (Invitrogen, La Jolla, Calif.).

Recombinantly produced ENR-A, CBL, UROD, PBGD, or CPPO enzymes, respectively, are isolated and purified using a variety of standard techniques. The actual techniques used varies depending upon the host organism used, whether the enzyme is designed for secretion, and other such factors. Such techniques are well known to the skilled artisan (see, e.g. chapter 16 of Ausubel, F. et al., "Current Protocols in Molecular Biology", pub. by John Wiley & Sons, Inc. (1994).

Recombinantly produced ENR-A, CBL, UROD, PBGD, or CPPO enzymes are useful for a variety of purposes. For example, they are used in in vitro assays to screen known herbicidal chemicals, whose target has not been identified, to determine if they inhibit ENR-A, CBL, UROD, PBGD, or CPPO enzymes, respectively. Such in vitro assays also are useful as screens to identify new chemicals that inhibit such enzymatic activity and that are therefore novel herbicide candidates. Alternatively, recombinantly produced ENR-A, CBL, UROD, PBGD, or CPPO enzymes, are used to further characterize their association with known inhibitors in order to rationally design new inhibitory herbicides as well as herbicide tolerant forms of the enzymes.

In Vitro Inhibitor Assays: Discovery of Small Molecule Ligand that Interacts with the Gene Product of SEQ ID NO:1, SEQ ID NO:3, SEQ ID NO:5, SEQ ID NO:7, and SEQ ID NO:9

Once a protein has been identified as a potential herbicide target, the next step is to develop an assay that allows screening large number of chemicals to determine which ones interact with the protein. Although it is straightforward to develop assays for proteins of known function, developing assays with proteins of unknown functions is more difficult. This difficulty can be overcome by using technologies that can detect interactions between a protein and a compound without knowing the biological function of the protein. A short description of three methods is presented, including fluorescence correlation spectroscopy, surface-enhanced laser desorption/ionization, and biacore technologies.

Fluorescence Correlation Spectroscopy (FCS) theory was developed in 1972 but it is only in recent years that the technology to perform FCS became available (Madge et al. (1972) Phys. Rev. Lett., 29: 705–708; Maiti et al. (1997) Proc. Natl. Acad. Sci. USA, 94: 11753–11757). FCS measures the average diffusion rate of a fluorescent molecule within a small sample volume. The sample size can be as low as $10^3$ fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding. In a typical experiment, the target to be analyzed is expressed as a recombinant protein with a sequence tag, such as a poly-histidine sequence, inserted at the N or C-terminus. The expression takes place in *E. coli,* yeast or insect cells. The protein is purified by chromatography. For example, the poly-histidine tag can be used to bind the expressed protein to a metal chelate column such as NI2+ chelated on iminodiacetic acid agarose. The protein is then labeled with a fluorescent tag such as carboxytetramethyl-rhodamine or BODIPY® (Molecular Probes, Eugene, Oreg.). The protein is then exposed in solution to the potential ligand, and its diffusion rate is determined by FCS using instrumentation available from Carl Zeiss, Inc. (Thornwood, N.Y.). Ligand binding is determined by changes in the diffusion rate of the protein.

Surface-Enhanced Laser Desorption/Ionization (SELDI) was invented by Hutchens and Yip during the late 1980's (Hutchens and Yip (1993) Rapid Commun. Mass Spectrom. 7: 576–580). When coupled to a time-of-flight mass spectrometer (TOF), SELDI provides a mean to rapidly analyze molecules retained on a chip. It can be applied to ligand-protein interaction analysis by covalently binding the target protein on the chip and analyze by MS the small molecules that bind to this protein (Worrall et al. (1998) Anal. Biochem. 70: 750–756). In a typical experiment, the target to be analyzed is expressed as described for FCS. The purified protein is then used in the assay without further preparation. It is bound to the SELDI chip either by utilizing the poly-histidine tag or by other interaction such as ion exchange or hydrophobic interaction. The chip thus prepared is then exposed to the potential ligand via, for example, a delivery system capable to pipet the ligands in a sequential manner (autosampler). The chip is then submitted to washes of increasing stringency, for example a series of washes with buffer solutions containing an increasing ionic strength. After each wash, the bound material is analyzed by submitting the chip to SELDI-TOF. Ligands that specifically bind the target will be identified by the stringency of the wash needed to elute them.

Biacore relies on changes in the refractive index at the surface layer upon binding of a ligand to a protein immobilized on the layer. In this system, a collection of small ligands is injected sequentially in a 2–5 microliter cell with the immobilized protein. Binding is detected by surface plasmon resonance (SPR) by recording laser light refracting from the surface. In general, the refractive index change for a given change of mass concentration at the surface layer, is practically the same for all proteins and peptides, allowing a single method to be applicable for any protein (Liedberg et al. (1983) Sensors Actuators 4: 299–304; Malmquist (1993) Nature, 361: 186–187). In a typical experiment, the target to be analyzed is expressed as described for FCS. The purified protein is then used in the assay without further preparation. It is bound to the Biacore chip either by utilizing the poly-histidine tag or by other interaction such as ion exchange or hydrophobic interaction. The chip thus prepared is then exposed to the potential ligand via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics on rate and off rate allows the discrimination between non-specific and specific interaction.

Also, an assay for small molecule ligands that interact with a polypeptide is an inhibitor assay. For example, such an inhibitor assay useful for identifying inhibitors of essential plant genes, such as plant ENR-A, CBL, UROD, PBGD, or CPPO genes, comprises the steps of:

a) reacting a plant ENR-A, CBL, UROD, PBGD, or CPPO enzyme, and a substrate thereof in the presence of a suspected inhibitor of the enzyme's function;

b) comparing the rate of enzymatic activity in the presence of the suspected inhibitor to the rate of enzymatic activity under the same conditions in the absence of the suspected inhibitor; and c) determining whether the suspected inhibitor inhibits the ENR-A, CBL, UROD, PBGD, or CPPO enzyme, respectively.

For example, the inhibitory effect on plant ENR-A, CBL, UROD, PBGD, or CPPO, may be determined by a reduction or complete inhibition of ENR-A, CBL, UROD, PBGD, or CPPO activity, respectively, in the assay. Such a determination may be made by comparing, in the presence and absence of the candidate inhibitor, the amount of substrate used or intermediate or product made during the reaction.

IV. In Vivo Inhibitor Assay

In one embodiment, a suspected herbicide, for example identified by in vitro screening, is applied to plants at various concentrations. The suspected herbicide is preferably sprayed on the plants. After application of the suspected herbicide, its effect on the plants, for example death or suppression of growth is recorded.

In another embodiment, an in vivo screening assay for inhibitors of the ENR-A, CBL, UROD, PBGD, or CPPO activity, uses transgenic plants, plant tissue, plant seeds or plant cells capable of overexpressing a nucleotide sequence having ENR-A, CBL, UROD, PBGD, or CPPO activity, respectively, wherein the ENR-A, CBL, UROD, PBGD, or CPPO gene product, is enzymatically active in the transgenic plants, plant tissue, plant seeds or plant cells. The nucleotide sequence is preferably derived from an eukaryote, such as a yeast, but is preferably derived from a plant. In a further preferred embodiment, the nucleotide sequence is identical or substantially similar to the nucleotide sequence set forth in SEQ ID NO:1, SEQ ID NO:3, SEQ ID NO:5, SEQ ID NO:7, or SEQ ID NO:9, or encodes an enzyme having ENR-A, CBL, UROD, PBGD, or CPPO activity, respectively, whose amino acid sequence is identical or substantially similar to the amino acid sequence set forth in SEQ ID NO:2, SEQ ID NO:4, SEQ ID NO:6, SEQ ID NO:8, or SEQ ID NO:10. In another preferred embodiment, the nucleotide sequence is derived from a prokaryote.

A chemical is then applied to the transgenic plants, plant tissue, plant seeds or plant cells and to the isogenic non-transgenic plants, plant tissue, plant seeds or plant cells, and the growth or viability of the transgenic and non-transformed plants, plant tissue, plant seeds or plant cells are determined after application of the chemical and compared. Compounds capable of inhibiting the growth of the non-transgenic plants, but not affecting the growth of the transgenic plants are selected as specific inhibitors of ENR-A, CBL, UROD, PBGD, or CPPO activity, respectively.

V. Herbicide Tolerant Plants

Development of tolerance can allow application of a herbicide to a crop where its use was previously precluded or limited (e.g. to pre-emergence use) due to sensitivity of the crop to the herbicide. For example, U.S. Pat. No. 4,761,373 to Anderson et al. is directed to plants resistant to various imidazolinone or sulfonamide herbicides. The resistance is conferred by an altered acetohydroxyacid synthase (AHAS) enzyme. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659 to Bedbrook et al. is directed to plants expressing a mutant acetolactate synthase that renders the plants resistant to inhibition by sulfonylurea herbicides. U.S. Pat. No. 5,162,602 to Somers et al. discloses plants tolerant to inhibition by cyclohexanedione and aryloxyphenoxypropanoic acid herbicides. The tolerance is conferred by an altered acetyl coenzyme A carboxylase (ACCase).

The present invention is further directed to plants, plant tissue, plant seeds, and plant cells tolerant to herbicides that inhibit the naturally occurring ENR-A, CBL, UROD, PBGD, or CPPO, in these plants, wherein the tolerance is conferred by altered ENR-A, CBL, UROD, PBGD, or CPPO ENR-A enzyme activity, respectively. Altered ENR-A, CBL, UROD, PBGD, or CPPO enzyme activity, is conferred upon a plant according to the invention by increasing expression of wild-type herbicide-sensitive ENR-A, CBL, UROD, PBGD, or CPPO enzyme, by providing additional wild-type ENR-A, CBL, UROD, PBGD, or CPPO genes, to the plant, by expressing modified herbicide-tolerant ENR-A, CBL, UROD, PBGD, or CPPO enzymes, in the plant, or by a combination of these techniques. Representative plants include any plants to which these herbicides are applied for their normally intended purpose. Preferred are agronomically important crops such as cotton, soybean, oilseed rape, sugar beet, maize, rice, wheat, barley, oats, rye, sorghum, millet, turf, forage, turf grasses, and the like.

A. Increased Expression of Wild-Type ENR-A, CBL, UROD, PBGD, or CPPO Enzymes

Achieving altered ENR-A, CBL, UROD, PBGD, or CPPO enzyme activity, through increased expression results in a level of a ENR-A, CBL, UROD, PBGD, or CPPO enzyme, respectively, in the plant cell at least sufficient to overcome growth inhibition caused by the herbicide. The level of expressed enzyme generally is at least two times, preferably at least five times, and more preferably at least ten times the natively expressed amount. Increased expression is conferred in a number of ways, e.g., providing multiple copies of a wild-type ENR-A, CBL, UROD, PBGD, or CPPO gene, respectively; multiple occurrences of the coding sequence within the gene (i.e. gene amplification) or a mutation in the non-coding, regulatory sequence of the endogenous gene in the plant cell. Plants having such altered gene activity are obtained by direct selection in plants by methods known in the art (see, e.g. U.S. Pat. Nos. 5,162,602, and 4,761,373, and references cited therein). These plants also may be obtained by genetic engineering techniques known in the art. Increased expression of a herbicide-sensitive ENR-A, CBL, UROD, PBGD, or CPPO gene, also is accomplished by stably transforming a plant cell with a recombinant or chimeric DNA molecule comprising a promoter capable of driving expression of an associated structural gene in a plant cell operatively linked to a homologous or heterologous structural gene encoding the ENR-A, CBL, UROD, PBGD, or CPPO enzyme.

B. Expression of Modified Herbicide-Tolerant ENR-A, CBL, UROD, PBGD, or CPPO Enzymes According to this embodiment, plants, plant tissue, plant seeds, or plant cells are stably transformed with a recombinant DNA molecule comprising a suitable promoter functional in plants operatively linked to a coding sequence encoding a herbicide tolerant form of a ENR-A, CBL, UROD, PBGD, or CPPO enzyme. A herbicide tolerant form of the enzyme has at least one amino acid substitution, addition or deletion that confers tolerance to an amount of a herbicide effective to inhibit the unmodified, naturally occurring form of the ENR-A, CBL, UROD, PBGD, or CPPO enzyme. The transgenic plants, plant tissue, plant seeds, or plant cells thus created are selected by conventional selection techniques, whereby herbicide tolerant lines are isolated, characterized, and developed. Below are described methods for obtaining genes that encode herbicide tolerant forms of ENR-A, CBL, UROD, PBGD, or CPPO enzymes.

One strategy involves direct or indirect mutagenesis procedures on microbes. For instance, a genetically manipulatable microbe such as *E. coli* or *S. cerevisiae* may be subjected to random mutagenesis in vivo with mutagens such as UV light or ethyl or methyl methane sulfonate. Mutagenesis procedures are described, for example, in Miller, *Experiments in Molecular Genetics,* Cold Spring Harbor Laboratory, Cold Spring Harbor, N.Y. (1972); Davis et al., *Advanced Bacterial Genetics,* Cold Spring Harbor Laboratory, Cold Spring Harbor, N.Y. (1980); Sherman et al., *Methods in Yeast Genetics,* Cold Spring Harbor Laboratory, Cold Spring Harbor, N.Y. (1983); and U.S. Pat. No. 4,975,374. The microbe selected for mutagenesis contains a normal, inhibitor-sensitive ENR-A, CBL, UROD, PBGD, or CPPO gene, and is dependent upon the activity conferred by this gene. The mutagenized cells are grown in the presence of the inhibitor at concentrations that inhibit the unmodified gene. Colonies of the mutagenized microbe that grow better than the unmutagenized microbe in the presence of the inhibitor (i.e. exhibit resistance to the inhibitor) are selected for further analysis. ENR-A, CBL, UROD, PBGD, or CPPO genes, from these colonies are isolated, either by cloning or by PCR amplification, and their sequences are elucidated. Sequences encoding altered gene products are then cloned back into the microbe to confirm their ability to confer inhibitor tolerance.

A method of obtaining mutant herbicide-tolerant alleles of a plant ENR-A, CBL, UROD, PBGD, or CPPO gene, involves direct selection in plants. For example, the effect of a mutagenized ENR-A, CBL, UROD, PBGD, or CPPO gene, on the growth inhibition of plants such as Arabidopsis, soybean, or maize is determined by plating seeds sterilized by art-recognized methods on plates on a simple minimal salts medium containing increasing concentrations of the inhibitor. Such concentrations are in the range of 0.001, 0.003, 0.01, 0.03, 0.1, 0.3, 1, 3, 10, 30, 110, 300, 1000 and 3000 parts per million (ppm). The lowest dose at which significant growth inhibition can be reproducibly detected is used for subsequent experiments.

Mutagenesis of plant material is utilized to increase the frequency at which resistant alleles occur in the selected population. Mutagenized seed material is derived from a variety of sources, including chemical or physical mutagenesis of seeds, or chemical or physical mutagenesis of pollen (Neuffer, In *Maize for Biological Research* Sheridan, ed. Univ. Press, Grand Forks, N. Dak., pp. 61–64 (1982)), which is then used to fertilize plants and the resulting $M_1$ mutant seeds collected. Typically for Arabidopsis $M_2$ seeds, which are progeny seeds of plants grown from seeds mutagenized with chemicals, such as ethyl methane sulfonate, or with physical agents, such as gamma rays or fast neutrons, are plated at densities of up to 10,000 seeds/plate (10 cm diameter) on minimal salts medium containing an appropriate concentration of inhibitor to select for tolerance. Seedlings that continue to grow and remain green 7–21 days after plating are transplanted to soil and grown to maturity and seed set. Progeny of these seeds are tested for tolerance to a ENR-A, CBL, UROD, PBGD, or CPPOinhibitor. If the tolerance trait is dominant, plants whose seed segregate 3:1/resistant:sensitive are presumed to have been heterozygous for the resistance at the $M_2$ generation. Plants that give rise to all resistant seed are presumed to have been homozygous for the resistance at the $M_2$ generation. Such mutagenesis on intact seeds and screening of their M2 progeny seed can also be carried out on other species, for instance soybean (see, e.g. U.S. Pat. No. 5,084,082). Alternatively, mutant seeds to be screened for herbicide tolerance are obtained as a result of fertilization with pollen mutagenized by chemical or physical means.

Confirmation that the genetic basis of the herbicide tolerance is a modified ENR-A, CBL, UROD, PBGD, or CPPO gene, is ascertained as exemplified below. First, alleles of the ENR-A, CBL, UROD, PBGD, or CPPO gene, from plants exhibiting resistance to the inhibitor are isolated using PCR with primers based either upon conserved regions in the Arabidopsis cDNA coding sequences shown in SEQ ID NO:1 or, more preferably, based upon the unaltered ENR-A, CBL, UROD, PBGD, or CPPO gene sequence, from the plant used to generate tolerant alleles. After sequencing the alleles to determine the presence of mutations in the coding sequence, the alleles are tested for their ability to confer tolerance to the inhibitor on plants into which the putative tolerance-conferring alleles have been transformed. These plants are Arabidopsis plants or any other plant whose growth is susceptible to the inhibitors. Second, the ENR-A, CBL, UROD, PBGD, or CPPO genes, are mapped relative to known restriction fragment length polymorphisms (RFLPs) (See, for example, Chang et al. *Proc. Natl. Acad, Sci, USA* 85: 6856–6860 (1988); Nam et al., *Plant Cell* 1:

699–705 (1989). The tolerance trait is independently mapped using the same markers. When tolerance is due to a mutation in that ENR-A, CBL, UROD, PBGD, or CPPO gene, the tolerance trait maps to a position indistinguishable from the position of the ENR-A, CBL, UROD, PBGD, or CPPO gene.

Another method of obtaining herbicide-tolerant alleles of a ENR-A, CBL, UROD, PBGD, or CPPO gene, is by selection in plant cell cultures. Explants of plant tissue, e.g. embryos, leaf disks, etc. or actively growing callus or suspension cultures of a plant of interest are grown on medium in the presence of increasing concentrations of a ENR-A, CBL, UROD, PBGD, or CPPO, inhibitor. Varying degrees of growth are recorded in different cultures. In certain cultures, fast-growing variant colonies arise that continue to grow even in the presence of normally inhibitory concentrations of inhibitor. The frequency with which such faster-growing variants occur can be increased by treatment with a chemical or physical mutagen before exposing the tissues or cells to the inhibitor. Putative tolerance-conferring alleles of the ENR-A, CBL, UROD, PBGD, or CPPO gene, are isolated and tested as described in the foregoing paragraphs. Those alleles identified as conferring herbicide tolerance may then be engineered for optimal expression and transformed into the plant. Alternatively, plants can be regenerated from the tissue or cell cultures containing these alleles.

Still another method involves mutagenesis of wild-type, herbicide sensitive plant ENR-A, CBL, UROD, PBGD, or CPPO genes, in bacteria or yeast, followed by culturing the microbe on medium that contains inhibitory concentrations of the inhibitor and then selecting those colonies that grow in the presence of the inhibitor. More specifically, a plant cDNA, such as the Arabidopsis cDNA encoding ENR-A (SEQ ID NO:1), CBL (SEQ ID NO:3), UROD (SEQ ID NO:5), PBGD (SEQ ID NO:7), or CPPO (SEQ ID NO:9), is cloned into a microbe that otherwise lacks the selected gene's activity. The transformed microbe is then subjected to in vivo mutagenesis or to in vitro mutagenesis by any of several chemical or enzymatic methods known in the art, e.g. sodium bisulfite (Shortle et al., *Methods Enzymol.* 100:457–468 (1983); methoxylamine (Kadonaga et al., *Nucleic Acids Res.* 13:1733–1745 (1985); oligonucleotide-directed saturation mutagenesis (Hutchinson et al., *Proc. Natl. Acad. Sci. USA*, 83:710–714 (1986); or various polymerase misincorporation strategies (see, e.g. Shortle et al., Proc. Natl. Acad. Sci. USA, 79:1588–1592 (1982); Shiraishi et al., *Gene* 64:313–319 (1988); and Leung et al., *Technique* 1:11–15 (1989). Colonies that grow in the presence of normally inhibitory concentrations of inhibitor are picked and purified by repeated restreaking. Their plasmids are purified and tested for the ability to confer tolerance to the inhibitor by retransforming them into the microbe lacking ENR-A, CBL, UROD, PBGD, or CPPO gene activity. The DNA sequences of cDNA inserts from plasmids that pass this test are then determined.

Herbicide resistant ENR-A, CBL, UROD, PBGD, or CPPO proteins, are also obtained using methods involving in vitro recombination, also called DNA shuffling. By DNA shuffling, mutations, preferably random mutations, are introduced into nucleotide sequences encoding ENR-A, CBL, UROD, PBGD, or CPPO activity, respectively. DNA shuffling also leads to the recombination and rearrangement of sequences within a ENR-A, CBL, UROD, PBGD, or CPPO gene, or to recombination and exchange of sequences between two or more different of ENR-A, CBL, UROD, PBGD, or CPPO genes, respectively. These methods allow for the production of millions of mutated ENR-A, CBL, UROD, PBGD, or CPPO coding sequences. The mutated genes, or shuffled genes, are screened for desirable properties, e.g. improved tolerance to herbicides and for mutations that provide broad spectrum tolerance to the different classes of inhibitor chemistry. Such screens are well within the skills of a routineer in the art.

In a preferred embodiment, a mutagenized ENR-A, CBL, UROD, PBGD, or CPPO gene, is formed from at least one template ENR-A, CBL, UROD, PBGD, or CPPO gene, wherein the template ENR-A, CBL, UROD, PBGD, or CPPO gene, has been cleaved into double-stranded random fragments of a desired size, and comprising the steps of adding to the resultant population of double-stranded random fragments one or more single or double-stranded oligonucleotides, wherein said oligonucleotides comprise an area of identity and an area of heterology to the double-stranded random fragments; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide, wherein the mutagenized polynucleotide is a mutated ENR-A, CBL, UROD, PBGD, or CPPO gene, having enhanced tolerance to a herbicide which inhibits naturally occurring ENR-A, CBL, UROD, PBGD, or CPPO activity. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles. Such method is described e.g. in Stemmer et al. (1994) Nature 370: 389–391, in U.S. Pat. Nos. 5,605,793, 5,811,238 and in Crameri et al. (1998) Nature 391: 288–291, as well as in WO 97/20078, and these references are incorporated herein by reference.

In another preferred embodiment, any combination of two or more different ENR-A, CBL, UROD, PBGD, or CPPO genes, are mutagenized in vitro by a staggered extension process (StEP), as described e.g. in Zhao et al. (1998) Nature Biotechnology 16: 258–261. The two or more ENR-A, CBL, UROD, PBGD, or CPPO genes, respectively, are used as template for PCR amplification with the extension cycles of the PCR reaction preferably carried out at a lower temperature than the optimal polymerization temperature of the polymerase. For example, when a thermostable polymerase with an optimal temperature of approximately 72° C. is used, the temperature for the extension reaction is desirably below 72° C., more desirably below 65° C., preferably below 60° C., more preferably the temperature for the extension reaction is 55° C. Additionally, the duration of the extension reaction of the PCR cycles is desirably shorter than usually carried out in the art, more desirably it is less than 30 seconds, preferably it is less than 15 seconds, more preferably the duration of the extension reaction is 5 seconds. Only a short DNA fragment is polymerized in each extension reaction, allowing template switch of the extension products between the starting DNA molecules after each cycle of denaturation and annealing, thereby generating diversity among the extension products. The optimal number of cycles in the PCR reaction depends on the length of the ENR-A, CBL, UROD, PBGD, or CPPO genes, to be mutagenized but desirably over 40 cycles, more desirably over 60 cycles, preferably over 80 cycles are used. Optimal extension conditions and the optimal number of PCR cycles for every combination of ENR-A, CBL, UROD, PBGD, or CPPO genes, are determined as described in using procedures well-known in the art. The other parameters for the PCR reaction are essentially the same as commonly used in the art. The primers for the amplification reaction are preferably designed to anneal to DNA sequences located outside of the ENR-A, CBL, UROD, PBGD, or CPPO genes, e.g. to DNA sequences of a vector comprising the ENR-A, CBL, UROD, PBGD, or CPPO genes, whereby the different ENR-A, CBL, UROD, PBGD, or CPPO genes, used in the PCR reaction are preferably comprised in separate vectors. The primers desirably anneal to sequences located less than 500 bp away from ENR-A, CBL, UROD, PBGD, or CPPO sequences, preferably less than 200 bp away from the ENR-A, CBL, UROD, PBGD, or CPPO sequences, more preferably less than 120 bp away from the ENR-A, CBL, UROD, PBGD, or CPPO sequences. Preferably, the ENR-A, CBL, UROD, PBGD, or CPPO sequences, are surrounded by restriction sites, which are included in the DNA sequence amplified during the PCR reaction, thereby facilitating the cloning of the amplified products into a suitable vector. In another preferred embodiment, fragments of ENR-A, CBL, UROD, PBGD, or CPPO genes, having cohesive ends are produced as described in WO 98/05765. The cohesive ends are produced by ligating a first oligonucleotide corresponding to a part of a ENR-A, CBL, UTROD, PBGD, or CPPO gene, to a second oligonucleotide not present in the gene or corresponding to a part of the gene not adjoining to the part of the gene corresponding to the first oligonucleotide, wherein the second oligonucleotide contains at least one ribonucleotide. A double-stranded DNA is produced using the first oligonucleotide as template and the second oligonucleotide as primer. The ribonucleotide is cleaved and removed. The nucleotide(s) located 5' to the ribonucleotide is also removed, resulting in double-stranded fragments having cohesive ends. Such fragments are randomly reassembled by ligation to obtain novel combinations of gene sequences.

Any ENR-A, CBL, UROD, PBGD, or CPPO gene, or any combination of ENR-A, CBL, UROD, PBGD, or CPPO genes, or homologs thereof, is used for in vitro recombination in the context of the present invention, for example, a ENR-A, CBL, UROD, PBGD, or CPPO gene, derived from a plant, such as, e.g. *Arabidopsis thaliana,* e.g. a ENR-A gene set forth in SEQ ID NO:1, CBL gene set forth in SEQ ID NO:3, UROD gene set forth in SEQ ID NO:5, PBGD gene set forth in SEQ ID NO:7, or CPPO gene set forth in SEQ ID NO:9. Whole ENR-A, CBL, UROD, PBGD, or CPPO genes, or portions thereof are used in the context of the present invention. The library of mutated ENR-A, CBL, UROD, PBGD, or CPPO genes, obtained by the methods described above are cloned into appropriate expression vectors and the resulting vectors are transformed into an appropriate host, for example a plant cell, an algae like Chlamydomonas, a yeast or a bacteria. An appropriate host requires ENR-A, CBL, UROD, PBGD, or CPPO gene product activity, for growth. Host cells transformed with the vectors comprising the library of mutated ENR-A, CBL, UROD, PBGD, or CPPO genes, are cultured on medium that contains inhibitory concentrations of the inhibitor and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined.

An assay for identifying a modified ENR-A, CBL, UROD, PBGD, or CPPO gene, that is tolerant to an inhibitor may be performed in the same manner as the assay to identify inhibitors of the ENR-A, CBL, UROD, PBGD, or CPPO enzyme, respectively, (Inhibitor Assay, above) with the following modifications: First, a mutant ENR-A, CBL, UROD, PBGD, or CPPO enzyme, is substituted in one of the reaction mixtures for the wild-type ENR-A, CBL, UROD, PBGD, or CPPO enzyme, respectively, of the inhibitor assay. Second, an inhibitor of wild-type enzyme is present in both reaction mixtures. Third, mutated activity (activity in the presence of inhibitor and mutated enzyme) and unmutated activity (activity in the presence of inhibitor and wild-type enzyme) are compared to determine whether a significant increase in enzymatic activity is observed in the mutated activity when compared to the unmutated activity. Mutated activity is any measure of activity of the mutated enzyme while in the presence of a suitable substrate and the inhibitor. Unmutated activity is any measure of activity of the wild-type enzyme while in the presence of a suitable substrate and the inhibitor. A significant increase is defined as an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, most preferably an increase by about 10-fold or greater.

In addition to being used to create herbicide-tolerant plants, genes encoding herbicide tolerant ENR-A, CBL, UROD, PBGD, or CPPO enzymes, also are used as selectable markers in plant cell transformation methods. For example, plants, plant tissue, plant seeds, or plant cells transformed with a transgene are transformed with a gene encoding an altered ENR-A, CBL, UROD, PBGD, or CPPO enzyme, capable of being expressed by the plant. The transformed cells are transferred to medium containing an ENR-A, CBL, UROD, PBGD, or CPPO inhibitor, in an amount sufficient to inhibit the survivability of plant cells not expressing the modified gene, wherein only the transformed cells will survive. The method is applicable to any plant cell capable of being transformed with a modified ENR-A, CBL, UROD, PBGD, or CPPO enzyme-encoding gene, and can be used with any transgene of interest. Expression of the transgene and the inhibitor-tolerant CBL, UROD, PBGD, CPPO, or ENR-A gene, can be driven by the same promoter functional in plant cells, or by separate promoters.

VI. Plant Transformation Technology

A wild-type or herbicide-tolerant form of the ENR-A, CBL, UROD, PBGD, or CPPO gene, can be incorporated in plant or bacterial cells using conventional recombinant DNA technology. Generally, this involves inserting a DNA molecule encoding the ENR-A, CBL, UROD, PBGD, or CPPO enzyme, into an expression system to which the DNA molecule is heterologous (i.e., not normally present) using standard cloning procedures known in the art. The vector contains the necessary elements for the transcription and translation of the inserted protein-coding sequences in a host cell containing the vector. A large number of vector systems known in the art can be used, such as plasmids, bacteriophage viruses and other modified viruses. The components of the expression system optionally are modified to increase expression. For example, truncated sequences, nucleotide substitutions or other modifications optionally are employed. Expression systems known in the art are used to transform virtually any crop plant cell under suitable conditions. Transformed cells are regenerated into whole plants such that the chosen form of the ENR-A, CBL, UROD, PBGD, or CPPO gene, confers herbicide tolerance in the transgenic plants.

A. Requirements for Construction of Plant Expression Cassettes

Gene sequences intended for expression in transgenic plants are first operably linked to a suitable promoter expressible in plants. Such expression cassettes optionally comprise further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes are easily transferred to the plant transformation vectors described infra. The following is a description of various components of typical expression cassettes.

1. Promoters

The selection of the promoter used determines the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters known in the at can be used. For example, for constitutive expression, the CaMV 35S promoter, the rice actin promoter, or the ubiquitin promoter may be used. For regulatable expression, the chemically inducible PR-1 promoter from tobacco or Arabidopsis may be used (see, e.g., U.S. Pat. No. 5,689,044).

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons.

3. Sequences for the Enhancement or Regulation of Expression

Numerous sequences are known to enhance gene expression from within the transcriptional unit and these sequences can be used in conjunction with the genes of this invention to increase their expression in transgenic plants. For example, various intron sequences such as introns of the maize AdhI gene have been shown to enhance expression, particularly in monocotyledonous cells. In addition, a number of non-translated leader sequences derived from viruses also are known to enhance expression, and these are particularly effective in dicotyledonous cells.

4. Coding Sequence Optimization

The coding sequence of the selected gene optionally is genetically engineered by altering the coding sequence for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); and Koziel et al., *Bio/technol.* 11: 194 (1993); Fennoy and Bailey-Serres. *Nucl. Acids Res.* 21: 5294–5300 (1993). Methods for modifying coding sequences by taking into account codon usage in plant genes and in higher plants, green algae, and cyanobacteria are well known (see table 4 in: Murray et al. *Nucl. Acids Res.* 17: 477–498 (1989); Campbell and Gowri *Plant Physiol.* 92: 1–11(1990).

5. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. *J. Biol. Chem.* 26: 15104–15109 (1988)). Other gene products are localized to other organelles such as the mitochondrion and the peroxisome (e.g. Unger et al. *Plant Molec. Biol.* 13: 411–418 (1989)). The cDNAs encoding these products are manipulated to effect the targeting of heterologous gene products to these organelles. In addition, sequences have been characterized which cause the targeting of gene products to other cell compartments. Amino terminal sequences are responsible for targeting to the ER, the apoplast, and extracellular secretion from aleurone cells (Koehler & Ho, *Plant Cell* 2: 769–783 (1990)). Additionally, amino terminal sequences in conjunction with carboxy terminal sequences are responsible for vacuolar targeting of gene products (Shinshi et al. *Plant Molec. Biol.* 14: 357–368 (1990)). By the fusion of the appropriate targeting sequences described above to transgene sequences of interest one skilled in the art is able to direct the transgene product to any organelle or cell compartment.

B. Construction of Plant Transformation Vectors

Numerous transformation vectors available for plant transformation are known to those of ordinary skill in the plant transformation arts, and the genes pertinent to this invention are used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. *Gene* 19: 259–268 (1982); Bevan et al., *Nature* 304:184–187 (1983)), the bar gene, which confers resistance to the herbicide phosphinothricin (White et al., *Nucl. Acids Res* 18: 1062 (1990), Spencer et al. *Theor. Appl. Genet* 79: 625–631 (1990)), the hph gene, which confers resistance to the antibiotic hygromycin (Blochinger & Diggelmann, *Mol Cell Biol* 4: 2929–2931), and the dhfr gene, which confers resistance to methotrexate (Bourouis et al., *EMBO J.* 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)). Typical vectors suitable for Agrobacterium transformation include the binary vectors pCIB200 and pCIB2001, as well as the binary vector pCIB10 and hygromycin selection derivatives thereof. (See, for example, U.S. Pat. No. 5,639,949).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Typical vectors suitable for non-Agrobacterium transformation include pCIB3064, pSOG19, and pSOG35. (See, for example, U.S. Pat. No. 5,639,949).

C. Transformation Techniques

Once the coding sequence of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells.

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. In each case the transformed cells are regenerated to whole plants using standard techniques known in the art.

Transformation of most monocotyledon species has now also become routine. Preferred techniques include direct gene transfer into protoplasts using PEG or electroporation techniques, particle bombardment into callus tissue, as well as Agrobacterium-mediated transformation.

D. Plastid Transformation

In another preferred embodiment, a nucleotide sequence encoding a polypeptide having ENR-A, CBL, UROD, PBGD, or CPPO activity, is directly transformed into the plastid genome. Plastid expression, in which genes are inserted by homologous recombination into the several thousand copies of the circular plastid genome present in each plant cell, takes advantage of the enormous copy number advantage over nuclear-expressed genes to permit expression levels that can readily exceed 10% of the total soluble plant protein. In a preferred embodiment, the nucleotide sequence is inserted into a plastid targeting vector and transformed into the plastid genome of a desired plant host. Plants homoplasmic for plastid genomes containing the nucleotide sequence are obtained, and are preferentially capable of high expression of the nucleotide sequence.

Plastid transformation technology is for example extensively described in U.S. Pat. Nos. 5,451,513, 5,545,817, 5,545,818, and 5,877,462 in PCT application no. WO 95/16783 and WO 97/32977, and in McBride et al. (1994) Proc. Natl. Acad. Sci. USA 91, 7301–7305, all incorporated herein by reference in their entirety. The basic technique for plastid transformation involves introducing regions of cloned plastid DNA flanking a selectable marker together with the nucleotide sequence into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). The presence of cloning sites between these markers allowed creation of a plastid targeting vector for introduction of foreign genes (Staub, J. M., and Maliga, P. (1993) *EMBO J.* 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci.* USA 90, 913–917). Other selectable markers useful for plastid transformation are known in the art and encompassed within the scope of the invention.

VII. Breeding

The wild-type or altered form of a ENR-A, CBL, UROD, PBGD, or CPPO gene, of the present invention is utilized to confer herbicide tolerance to a wide variety of plant cells, including those of gymnosperms, monocots, and dicots. Although the gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The high-level expression of a wild-type ENR-A, CBL, UROD, PBGD, or CPPO gene, and/or the expression of herbicide-tolerant forms of a ENR-A, CBL, UROD, PBGD, or CPPO gene, conferring herbicide tolerance in plants, in combination with other characteristics important for production and quality, is incorporated into plant lines through breeding approaches and techniques known in the art.

Where a herbicide tolerant ENR-A, CBL, UROD, PBGD, or CPPO gene allele, is obtained by direct selection in a crop plant or plant cell culture from which a crop plant can be regenerated, it is moved into commercial varieties using traditional breeding techniques to develop a herbicide tolerant crop without the need for genetically engineering the allele and transforming it into the plant.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by Sambrook, et al., *Molecular Cloning,* eds., Cold Spring Harbor Laboratory Press, Cold Spring Harbor, N.Y. (1989)

and by T. J. Silhavy, M. L. Berman, and L. W. Enquist, *Experiments with Gene Fusions,* Cold Spring Harbor Laboratory, Cold Spring Harbor, N.Y. (1984) and by Ausubel, F. M. et al., *Current Protocols in Molecular Biology,* pub. by Greene Publishing Assoc. and Wiley-Interscience (1987).

Example 1

Regulation of the Expression of the CBL Gene

The CBL gene encodes a protein that carries out a step in the methionine biosynthesis pathway. CBL catalyzes the conversion of cystathionine to homocysteine (reviewed in Ravanel et al. (1998) *Proc. Natl. Acad, Sci, USA* 95: 7805–7812). The sequence of a cDNA for the Arabidopsis CBL gene has been identified (Ravanel et al. (1995) *Plant Mol. Biol.* 29: 875–882). The effect of the regulation of its expression in plants is tested using constructs for sense RNA expression (sense construct), antisense RNA expression (antisense construct) and antisense and sense RNA expression (antisense/sense construct).

A. Antisense construct: binary BASTA vector pJG261 is used containing a fragment from the pJG304ΔXhoI vector with an insertion of part of the CBL gene in an antisense orientation (nucleotides #13–1159, Genbank accession #L40511). pJG304/aCBL: Plasmid pJG304ΔXhoI is digested with NcoI and SacI to excise the GUS gene. The GUS gene from pJG304ΔXhoI is replaced with a CBL PCR product also digested with NcoI and SacI. This product is generated using primers DG354 (5' GAT CGA GCT CCA CGA GAA CTG TCT CCG 3'; SEQ ID NO:14) and DG357 (5' TCA GCC ATG GGA AGA CAA GTA CAT TGC 3'; SEQ ID NO:15) and the pFL61 Arabidopsis cDNA library (Minet et al. (1992) *Plant J.* 2: 417–422) as a template. Plasmid pJG304/aCBL is constructed from the pJG304ΔXhoI-digested vector ligated to the CBL PCR product. pJG261/aCBL: pJG304/aCBL is cut with XhoI to excise the cassette containing the GAL4 DNA binding site/35S minimal promoter/antisense CBL/CaMV terminator fusion. This cassette is ligated into XhoI-digested pJG261 (Guyer, et al, *Genetics* (1998), 149: 633–639.), producing pJG261/aCBL.

B. Sense construct: same as antisense construct, except the CBL fragment is in the opposite orientation. This construct contains the ATG start codon and most of the CBL ORF and serves as a control for regulation of the expression of the CBL gene. pJG304/sCBL: Plasmid pJG304ΔXhoI is digested with NcoI and SacI to excise the GUS gene. The GUS gene from pJG304ΔXhoI is replaced with a CBL PCR product also digested with NcoI and SacI. This product is generated using primers CBL1 (5' CTT GCC ATG GCA CGA GAA CTG TCT CCG 3'; SEQ ID NO:8) and CBL2 (5' CAT GGA GCT CGA AGA CAA GTA CAT TGC A 3'; SEQ ID NO:17) and the pFL61 Arabidopsis cDNA library as a template. Plasmid pJG304/sCBL is constructed from the pJG304ΔXhoI-digested vector ligated to the CBL PCR product. pJG261/sCBL: pJG304/sCBL is cut with XhoI to excise the cassette containing the GAL4 DNA binding site/35S minimal promoter/sense CBL/CaMV terminator fusion. This cassette is ligated into XhoI-digested pJG261, producing pJG261/sCBL.

C. Antisense/sense construct: A CBL gene fragment (nucleotides #13–1159, Genbank accession #L40511) in the sense orientation is inserted into the SalI site of vector pJG304ΔXhoI downstream of the antisense orientation version of the CBL gene. A linker of about 10 bp is present between the two copies of CBL. pJG304/dsCBL: Plasmid pJG304/aCBL is digested with SacI. A CBL PCR product also digested with SacI is inserted so that the inserted CBL gene is in the sense orientation. This product is generated using CBL2 (5' CAT GGA GCT CGA AGA CAA GTA CAT TGC A 3'; SEQ ID NO:17) and CBL3 (5' CAT CGA GCT CCT CTG TTT AAA CCA CGA GAA CTG TCT CCG TCG C 3'; SEQ ID NO:18) and the pFL61 Arabidopsis cDNA library as a template. The plasmid construct with the desired orientation of the inserted DNA is identified by digestion with HindIII. Plasmid pJG304/dsCBL is constructed from the pJG304/aCBL-digested vector ligated to the CBL PCR product. SURE2 (Stratagene, LaJolla, Calif.) is used as the bacterial host to stabilize the construct. pJG261/dsCBL: pJG304/dsCBL is cut with XbaI to excise the cassette containing the GAL4 DNA binding site/35S minimal promoter/antisense CBL/sense CBL/CaMV terminator fusion. This cassette is ligated into SpeI-digested pJG261, producing pJG261/dsCBL. XL1-BLUE MRF' (Stratagene, LaJolla, Calif.) is used as the bacterial host to partially stabilize the construct. Unrearranged DNA for this construct is isolated by agarose gel purification.

D. Production of GAL4 Binding Site/Minimal CaMV 35S/CBL Transgenic Plants

The three described pJG261/CBL constructs are electro-transformed (Bio-Rad Laboratories, Hercules, Calif.) into *Agrobacterium tumefaciens* recA⁻ strain AGL1 (Lazo et al. (1991) *Bio/Technology* 9: 963–967), and Arabidopsis plants (Ecotype Columbia) are transformed by infiltration (Bechtold et al., (1993) *C. R. Acad. Sci. Paris,* 316: 1188–1193). Seeds from the infiltrated plants are selected on germination medium (Murashige-Skoog salts at 4.3 g/liter, Mes at 0.5 g/liter, 1% sucrose, thiamine at 10 ug/liter, pyridoxine at 5 ug/liter, nicotinic acid at 5 ug/liter, myo-inositol at 1 mg/liter, pH 5.8) containing Basta at 15 mg/liter.

E. Comparison of the Inhibition of CBL Using a GAL4/C1 Transactivator and a GAL4 Binding Site/Minimal 35S Promoter Transgenic plants containing a GAL4 binding site/minimal CaMV 35S promoter/ CBL construct are transplanted to soil and grown to maturity in the greenhouse. The presence of a transgenic CBL fragment in each line is confirmed by PCR. To test for the antisense construct, primers ASV1 (5' TTT GGA GAG GAC AGA CCT GC 3'; SEQ ID NO:19) and CBL3 (5' CAT CGA GCT CCT CTG TTT AAA CCA CGA GAA CTG TCT CCG TCG C 3'; SEQ ID NO:18) are used to verify the presence of an approximately 1200 bp product. Six transgenic lines with the antisense construct are identified. To test for the sense construct, primers ASV2 (5' GGA TTT TGG TTT TAG GAA TTA GAA 3'; SEQ ID NO:20) and CBL3 (5' CAT CGA GCT CCT CTG TTT AAA CCA CGA GAA CTG TCT CCG TCG C 3'; SEQ ID NO:18) are used to verify the presence of an approximately 1200 bp product. Thirteen transgenic lines with the sense construct are identified. To test for the antisense/sense construct, primers ASV2 (5' GGA TTT TGG TTT TAG GAA TTA GAA 3'; SEQ ID NO:20) and CBL3 (5' CAT CGA GCT CCT CTG TTT AAA CCA CGA GAA CTG TCT CCG TCG C 3'; SEQ ID NO:18) are used to verify the presence of an approximately 1200 bp product. In addition, to test for the antisense/sense construct, primers ASV1 (5' TTT GGA GAG GAC AGA CCT GC 3'; SEQ ID NO:19) and CBL3 (5' CAT CGA GCT CCT CTG TTT AAA CCA CGA GAA CTG TCT CCG TCG C 3'; SEQ ID NO:18) are used to verify the presence of an approximately 1200 bp product. Eleven transgenic lines with the antisense/sense construct are identified.

Flowers borne on the primary transformants are crossed to pollen from the homozygous GAL4/C1 transactivator line pAT53-103 (Guyer et al, *Genetics* (1998)149: 633–649). F1seeds are plated on MS+2% sucrose medium (Murashige-Skoog salts at 4.3 g/liter, Mes at 0.5 g/liter, 2% sucrose). None of the lines comprising the antisense construct show an abnormal phenotype for the F1 progeny on plates. Two of thirteen lines comprising the sense construct show a weak phenotype for approximately half of the F1 progeny on each plate. The other eleven of thirteen lines comprising the sense construct do not show an abnormal phenotype for the F1 progeny on plates. Ten of eleven lines comprising the antisense/sense construct show phenotypes ranging from weak to strong for approximately half of the F1 progeny on each plate. Plants with a strong phenotype do not survive and have an increase in purple coloration, lose green pigmentation, and fail to form leaves after fourteen days on the plates. Plants with weaker phenotypes have some purple coloration, are paler green than normal, and form smaller leaves after fourteen days on the plates. Thus, the inventors are the first to demonstrate that the CBL gene is essential for the growth of a plant. Previously, it has been shown that tobacco mutants lacking CBL activity were unable to grow without exogenously-supplied methionine (Negrutiu et al. (1985) *Mol. Gen. Genet.* 199: 330–337), but the molecular nature of the mutation has not been shown.

Example 2

Isolation of a cDNA Encoding UROD from Arabidopsis

Primers UROD-N-Nde (5'-GGGTTTCCATATGTCAATCCTTCAAGTCTC-3'; SEQ ID NO:22) and UROD-C-Not (5'-TTGCGCGGCCGCTTAATATCTAATTTCTTGAGC-3'; SEQ ID NO:23) are designed to the 5' and 3' ends of the predicted UROD ORF (Open Reading Frame) from BAC genomic sequence (GenBank accession #AC002336), and PCR is performed using DNA from the pFL61 Arabidopsis Landsberg cDNA library (Minet et al. (1992) *Plant J.* 2: 417–422) as the template. Another RT-PCR is also performed using RNA isolated from Arabidopsis Col-0 leaf tissue. The resulting PCR products are digested with NdeI and NotI and ligated to pET 32a vector DNA (Stratagene) treated with the same restriction enzymes and sequenced. The UROD sequences from Col-0 and Landsberg are the same. Both are identical with the predicted ORF. The prior indicated exon/intron boundaries are: 48272 . . . 48787, 48874 . . . 48999, 49107 . . . 49295, 49391 . . . 49501, 49603 . . . 49727, 50182 . . . 50299, in the current version of Genbank accession #AC002336 annotated as 36805 . . . 36922, 37377 . . . 37501, 37603 . . . 37713, 37809 . . . 37997, 38105 . . . 38230, 38317 . . . 38832. The cDNA sequence is the same as the sequence predicted in the Genbank annotation, thus validating for the first time the putative open reading frame annotation.

The Arabidopsis cDNA sequence encoding the UROD ORF is set forth in SEQ ID NO:5 and the encoded amino acid sequence is set forth in SEQ ID NO:6.

Example 3

Construction of a Vector Containing a GAL4 Binding Site/Minimal 35S CaMV Promoter Fused to Antisense UROD pJG304/UD Plasmid pJG304ΔXhoI (Guyer, et al, *Genetics* (1998), 149: 633–639) is digested with NcoI and BglII to excise the GUS gene. The GUS gene from pJG304ΔXhoI is replaced with a UROD PCR product digested with AflII (compatible with NcoI) and BamHI (compatible with BglII). This product is generated using primers UROD-F2 (5'-CCCGGATCCATGTCAATCCTTCAAGTC-3'; SEQ ID NO:24) and UROD-R2 (5'-CCCACATGTATATCTAATTTCTTGAGC-3'; SEQ ID NO:25) and the pFL61 cDNA library as a template. Plasmid pJG304/UD is constructed from the pJG304ΔXhoI digested vector ligated to the UROD PCR product.

Example 4

Plant Transformation Vectors for UROD Antisense Expression from the GAL4 Binding Site/CaMV Minimal 35S Promoter pJG261/UD pJG304/UD is cut with XhoI to excise the cassette containing the GAL4 DNA binding site/35S minimal promoter/antisense UROD/CaMV terminator fusion. This cassette is ligated into XhoI-digested pJG261 (Guyer, et al, *Genetics* (1998), 149:633–639.), producing pJG261/UD.

Example 5

Production of GAL4 Binding Site/Minimal CaMV 35S Antisense UROD Transgenic Plants pJG261/UD was electro-transformed (Bio-Rad Laboratories, Hercules, Calif.) into *Agrobacterium tumefaciens* strain GV3101, and Arabidopsis plants (Ecotype Columbia) were transformed by infiltration (Bechtold, et al., (1993) *C. R. Acad. Sci. Paris*, 316: 1188–93). Seeds from the infiltrated plants were selected on germination medium (Murashige-Skoog salts at 4.3 g/liter, Mes at 0.5 g/liter, 1% sucrose, thiamine at 10 ug/liter, pyridoxine at 5 ug/liter, nicotinic acid at 5 ug/liter, myo-inositol at 1 mg/liter, pH 5.8) containing Basta at 15 mg/liter.

Example 6

Antisense Inhibition of UROD Using a GAL4/C1 Transactivator and a GAL4 Binding Site/Minimal CaMV 35S Promoter Fifteen transgenic plants containing the GAL4 binding site/minimal CaMV 35S promoter/antisense UROD construct were transplanted to soil and grown to maturity in the greenhouse. Flowers borne on the primary transformants were crossed to pollen from the homozygous GAL4/C1 transactivator line pAT53-103 (Guyer et al, *Genetics* (1998) 149:633–649). F1 seeds were plated on MS+2% sucrose medium (Murashige-Skoog salts at 4.3 g/liter, Mes at 0.5 g/liter, 2% sucrose) 6 lines segregated about 50% seedlings with a bleached lethal phenotype on plates. Thus, the inventors are the first to demonstrate that the UROD gene is essential for the growth of a dicot. Previously, it has been shown that maize plants homozygous for a loss-of-function mutation in this gene are dead (Hu et al, *Plant Cell* (1998) 10:1095–1105). In addition, it has been shown that tobacco plants, expressing a transgenic antisense construct, with 45% residual UROD activity exhibit necrosis, but not lethality (Mock et al, *Plant Physiol.* (1997) 113:1101–1112).

Example 7

Construction of a Vector Containing a GAL4 Binding Site/Minimal 35S CaMV Promoter Fused to Antisense PBGD pJG304/UD Plasmid pJG304ΔXhoI (Guyer, et al, *Genetics* (1998), 149: 633–639) is digested with NcoI and BglII to excise the GUS gene. The GUS gene from pJG304ΔXhoI is replaced with a PBGD PCR product digested with BspHI (compatible with NcoI) and BglII. This product is generated using primers PORD-F2 (5'-CCC AGA TCT CCA TGG ATA TTG CTT CGT C-3'; SEQ ID NO:27) and PORD-R2 (5'-CCC TCA TGA AGA TAG CAA TTC TTG CCC-3'; SEQ ID NO:28) and the pFL61 cDNA library as a template. Plasmid pJG304/PD is constructed from the pJG304ΔXhoI digested vector ligated to the PBGD PCR product.

Example 8

Plant Transformation Vectors for PBGD Antisense Expression from the GAL4 Binding Site/CaMV Minimal 35S Promoter pJG261/PD pJG304/PD is cut with XhoI to excise the cassette containing the GAL4 DNA binding site/35S minimal promoter/antisense PBGD/CaMV terminator fusion. This cassette is ligated into XhoI-digested pJG261 (Guyer, et al, *Genetics* (1998), 149:633–639), producing pJG261/PD.

Example 9

Production of GAL4 Binding Site/Minimal CaMV 35S Antisense PBGD Transgenic Plants pJG261/PD was electro-transformed (Bio-Rad Laboratories, Hercules, Calif.) into *Agrobacterium tumefaciens* strain GV3101, and Arabidopsis plants (Ecotype Columbia) were transformed by infiltration (Bechtold, et al., (1993) *C. R. Acad. Sci. Paris,* 316: 1188–93). Seeds from the infiltrated plants were selected on germination medium (Murashige-Skoog salts at 4.3 g/liter, MES at 0.5 g/liter, 1% sucrose, thiamine at 10 ug/liter, pyridoxine at 5 ug/liter, nicotinic acid at 5 ug/liter, myo-inositol at 1 mg/liter, pH 5.8) containing Basta at 15 mg/liter.

Example 10

Antisense Inhibition of PBGD Using a GAL4/C1 Transactivator and a GAL4 Binding Site/Minimal CaMV 35S Promoter Eighteen transgenic plants containing the GAL4 binding site/minimal CaMV 35S promoter/antisense PBGD construct were transplanted to soil and grown to maturity in the greenhouse. Flowers borne on the primary transformants were crossed to pollen from the homozygous GAL4/C1 transactivator line pAT53-103 (Guyer et al, *Genetics* (1998) 149:633–649). F1 seeds were plated on MS+2% sucrose medium (Murashige-Skoog salts at 4.3 g/liter, Mes at 0.5 g/liter, 2% sucrose) eight lines segregated about 50% seedlings with a bleached lethal phenotype on plates. Thus, the inventors are the first to demonstrate that the PBGD gene is essential for the growth of a plant.

Example 11

Isolation of a cDNA Encoding CPPO from Arabidopsis

Primer CR73 (5' TTG ACC CTT CCT TCT ATC CCC GAT TC 3': SEQ ID NO:30) is designed to anneal to the complementary strand at 733–758 nucleotides from the 5' end of the start codon of the predicted CPPO ORF from the BAC F21B7 genomic sequence (GenBank accession #AC002560), and primer CR75 (5' GTT GCC ATG CCT TGT GCT GCT CTG TA 3': SEQ ID NO:31) is designed to anneal to the coding strand from 958–933 nucleotides from the 5' end of the start codon of the predicted CPPO ORF from the BAC F21B7 genomic sequence (GenBank accession #AC002560). 3' RACE is performed using CR73 primer and 5' RACE is performed using CR75 primer with second strand cDNA from *Arabidopsis thaliana* v Columbia as the template (Marathon cDNA Amplification Kit User Manual, Clontech). The resulting PCR products are TA-ligated and cloned (Original TA Cloning Kit, Invitrogen), and sequenced.

There are two differences between the sequence of the present invention and the genomic sequence in the prior art. First, the genomic sequence contains GG at positions 67872–67873. However, the inventors are the first to provide experimental evidence that the correct sequence contains only one G at position 67872. In addition, the genomic DNA that contains the CPPO ORF was not annotated correctly in the prior art with respect to the number of exons and the exon boundaries, the inventors are the first to provide experimental documentation of the correct ORF for the CPPO gene. The prior art indicates these exon boundaries: 66178 . . . 66702, 66782 . . . 66857, 66946 . . . 67040, 67126 . . . 67209, 67391 . . . 67478, 67571 . . . 67695, 67801 . . . 67896. In the sequence of the present invention, base 66178 marks the first base of the cDNA's start codon and base 68050 (using the numbering of the deposited BAC which as indicated above is off by one nucleotide) marks the first base of the cDNA's stop codon. The 3' end of the exon 7 is 67900 (using the numbering of the deposited BAC which as indicated above is off by one nucleotide), and the 5' end of the exon containing the stop codon (i.e., exon 8) is 67984 (using the numbering of the deposited BAC which as indicated above is off by one nucleotide). The exon boundaries for the cDNA disclosed herein are: 66178 . . . 66702, 66782 . . . 66857, 66946 . . . 67040, 67126 . . . 67209, 67391 . . . 67478, 67571 . . . 67695, 67801 . . . 67900, 67984 . . . 68301.

The Arabidopsis cDNA sequence encoding the CPPO ORF is set forth in SEQ ID NO:9 and the encoded amino acid sequence is set forth in SEQ ID NO:10.

Example 12

Construction of a Vector Containing a GAL4 Binding Site/Minimal 35S CaMV Promoter Fused to Antisense CPPO pJG304ΔXhoI: Plasmid pJG304 (Guyer, et al, *Genetics* (1998), 149: 633–639) is partially digested with Asp718 to isolate a full-length linear fragment. This fragment is ligated with a molar excess of the 22 base oligonucleotide JG-L (5' GTA CCT CGA GTC TAG ACT CGA G 3'; SEQ ID NO:32). Restriction analysis is used to identify a clone with this linker inserted 5' to the GAL4 DNA binding site, and this plasmid is designated pJG304ΔXhoI.

pJG304/CO: Plasmid pJG304ΔXhoI is digested with NcoI and BglII to excise the GUS gene. The GUS gene from pJG304ΔXhoI is replaced with a CPPO PCR product also digested with NcoI and BGlII. This product is generated using primers CPPGO-F2 (5' CCC AGA TCT ATG GCT TCT CAC TCG TCG 3'; SEQ ID NO:33) and CPPGO-R2 (5' CAT GCC ATG GTA TTC CCA TCT TGC TGA AA 3'; SEQ ID NO:34) and the pFL61 cDNA library as a template. Plasmid pJG304/CO is constructed from the pJG304 digested vector ligated to the CPPO PCR product.

Example 13

Plant Transformation Vectors for CPPO Antisense Expression from the GAL4 Binding Site/CaMV Minimal 35S Promoter pJG261/CO: pJG304/CO is cut with XhoI to excise the cassette containing the GAL4 DNA binding site/35S minimal promoter/antisense CPPO/CaMV terminator fusion. This cassette is ligated into XhoI-digested pJG261 (Guyer, et al, *Genetics* (1998), 149:633–639.), producing pJG261/CO.

Example 14

Production of GAL4 Binding Site/Minimal CaMV 35S Antisense CPPO Transgenic Plants pJG261/CO was electro-transformed (Bio-Rad Laboratories, Hercules, Calif.) into *Agrobacterium tumefaciens* strain GV3101, and Arabidopsis plants (Ecotype Columbia) were transformed by infiltration (Bechtold, et al., (1993) *C. R. Acad. Sci. Paris,* 316: 1188–93). Seeds from the infiltrated plants were selected on germination medium (Murashige-Skoog salts at 4.3 g/liter, Mes at 0.5 g/liter, 1% sucrose, thiamine at 10 ug/liter, pyridoxine at 5 ug/liter, nicotinic acid at 5 ug/liter, myo-inositol at 1 mg/liter, pH 5.8) containing Basta at 15 mg/liter.

Example 15

Antisense Inhibition of CPPO Using a GAL4/C1 Transactivator and a GAL4 Binding Site/Minimal CaMV 35S Promoter

Fifteen transgenic plants containing the GAL4 binding site/minimal CaMV 35S promoter/antisense CPPO construct were transplanted to soil and grown to maturity in the greenhouse. Flowers borne on the primary transformants were crossed to pollen from the homozygous GAL4/C1 transactivator line pAT53-103 (Guyer et al, *Genetics* (1998) 149:633–649). F1 seeds were plated on MS+2% sucrose medium (Murashige-Skoog salts at 4.3 g/liter, Mes at 0.5 g/liter, 2% sucrose)13 lines segregated about 50% seedlings with a bleached lethal phenotype on plates. Thus, the inventors are the first to demonstrate that the CPPO gene is essential for the growth of a plant. Previously, it has been shown that tobacco plants expressing a transgenic antisense construct for this gene with 30–40% residual CPPO activity are sick (Kruse et al. *EMBO J* (1995) 14: 3712–3720).

Example 16

Construction of a Vector Containing a GAL4 Binding Site/Minimal 35S CaMV Promoter Fused to Antisense Enoyl-ACP Reductase (ENR-A) pJG304/ENR-A

Plasmid pJG304ΔXhoI (Guyer, et al, *Genetics* (1998), 149: 633–639) is digested with NcoI and BglII to excise the GUS gene. The GUS gene from pJG304ΔXhoI is replaced with a ENR-A PCR product digested NcoI and BglII. This product is generated using primers ENR-A-F2 (5'-CCC AGA TCT AAT GGC GGC TAC AGC AGC TT-3'; SEQ ID NO:12) and ENR-A-R2 (5'-CAT GCC ATG GCT AAT TCT TGC TGT TAA GG-3'; SEQ ID NO:13) and the pFL61 Arabidopsis cDNA library (Minet et al. (1992) Plant J. 2: 417–422) as a template. Plasmid pJG304/ENR-A is constructed from the pJG304ΔXhoI digested vector ligated to the ENR-A PCR product.

Example 17

Plant Transformation Vectors for Enoyl-ACP Reductase (ENR-A) Antisense Expression from the GAL4 Binding Site/CaMV Minimal 35S Promoter pJG261/ENR-A pJG304/ENR-A is cut with XbaI to excise the cassette containing the GAL4 DNA binding site/35S minimal promoter/antisense enoyl-ACP reductase/CaMV terminator fusion. This cassette is ligated into SpeI-digested pJG261 (Guyer, et al, *Genetics* (1998), 149:633–639), producing pJG261/ENR-A.

Example 18

Production of GAL4 Binding Site/Minimal CaMV 35S Antisense ENR-A Transgenic Plants pJG261/ENR-A was electro-transformed (Bio-Rad Laboratories, Hercules, Calif.) into *Agrobacterium tumefaciens* strain GV3101, and Arabidopsis plants (Ecotype Columbia) were transformed by infiltration (Bechtold, et al., (1993) *C. R. Acad. Sci. Paris,* 316: 1188–93). Seeds from the infiltrated plants were selected on germination medium (Murashige-Skoog salts at 4.3 g/liter, MES at 0.5 g/liter, 1% sucrose, thiamine at 10 ug/liter, pyridoxine at 5 ug/liter, nicotinic acid at 5 ug/liter, myo-inositol at 1 mg/liter, pH 5.8) containing Basta at 15 mg/liter.

Example 19

Antisense Inhibition of ENR-A Using a GAL4/C1 Transactivator and a GAL4 Binding Site/Minimal CaMV 35S Promoter

Sixteen transgenic plants containing the GAL4 binding site/minimal CaMV 35S promoter/antisense enoyl-ACP reductase construct were transplanted to soil and grown to maturity in the greenhouse. Flowers borne on the primary transformants were crossed to pollen from the homozygous GAL4/C1 transactivator line pAT53-103 (Guyer et al, *Genetics* (1998) 149:633–649). F1 seeds were plated on MS+2% sucrose medium (Murashige-Skoog salts at 4.3 g/liter, Mes at 0.5 g/liter, 2% sucrose). Two lines segregated about 50% seedling with a bleached phenotype on plates. These affected seedlings died shortly after transplanting to soil. Thus, the inventors are the first to demonstrate that the ENR-A gene is essential for the growth of a plant.

Example 20a

**Expression of Recombinant CBL Protein in *E. coli***

The coding region of the protein, corresponding to the cDNA clone SEQ ID NO:3, is subcloned into an appropriate expression vector, and transformed into *E. coli* using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of CBL activity is confirmed. Protein conferring CBL activity is isolated using standard techniques.

Example 20b

**Expression of Recombinant UROD Protein in *E. coli***

The coding region of the protein, corresponding to the cDNA clone SEQ ID NO:5, is subcloned into an appropriate expression vector, and transformed into *E. coli* using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of UROD activity is confirmed. Protein conferring UROD activity is isolated using standard techniques.

Example 20c

Expression of Recombinant PBGD Protein in *E. coli*

The coding region of the protein, corresponding to the cDNA clone SEQ ID NO:7, is subcloned into an appropriate expression vector, and transformed into *E. coli* using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of PBGD activity is confirmed. Protein conferring PBGD activity is isolated using standard techniques.

Example 20d

Expression of Recombinant CPPO Protein in *E. coli*

The coding region of the protein, corresponding to the cDNA clone SEQ ID NO:9, is subcloned into an appropriate expression vector, and transformed into *E. coli* using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of CPPO activity is confirmed. Protein conferring CPPO activity is isolated using standard techniques.

Example 20e

Expression of Recombinant ENR-A Protein in *E. coli*

The coding region of the protein, corresponding to the cDNA clone SEQ ID NO:1, is subcloned into an appropriate expression vector, and transformed into *E. coli* using the manufacturer's conditions. Specific examples include plasmids such as pBluescript (Stratagene, La Jolla, Calif.), pFLAG (International Biotechnologies, Inc., New Haven, Conn.), and pTrcHis (Invitrogen, La Jolla, Calif.). *E. coli* is cultured, and expression of ENR-A activity is confirmed. Protein conferring ENR-A activity is isolated using standard techniques.

Example 21

In vitro Recombination of ENR-A Genes by DNA Shuffling

The nucleotide sequence of SEQ ID NO:1, SEQ ID NO:3, SEQ ID NO:5, SEQ ID NO:7, or SEQ ID NO:9, respectively, is amplified by PCR. The resulting DNA fragment is digested by DNaseI treatment essentially as described (Stemmer et al. (1994) *PNAS* 91: 10747–10751) and the PCR primers are removed from the reaction mixture. A PCR reaction is carried out without primers and is followed by a PCR reaction with the primers, both as described (Stemmer et al. (1994) *PNAS* 91: 10747–10751). The resulting DNA fragments are cloned into pTRC99a (Pharmacia, Cat no: 27-5007-01) for use in bacteria, and transformed into a bacterial strain deficient in ENR-A, CBL, UROD, PBGD, or CPPO activity, respectively, by electroporation using the Biorad Gene Pulser and the manufacturer's conditions. The transformed bacteria are grown on medium that contains inhibitory concentrations of an inhibitor of ENR-A, CBL, UROD, PBGD, or CPPO activity, respectively, and those colonies that grow in the presence of the inhibitor are selected. Colonies that grow in the presence of normally inhibitory concentrations of inhibitor are picked and purified by repeated restreaking. Their plasmids are purified and the DNA sequences of cDNA inserts from plasmids that pass this test are then determined. Alternatively, the DNA fragments are cloned into expression vectors for transient or stable transformation into plant cells, which are screened for differential survival and/or growth in the presence of an inhibitor of ENR-A, CBL, UROD, PBGD, or CPPO activity, respectively. In a similar reaction, PCR-amplified DNA fragments comprising the Arabidopsis ENR-A, CBL, UROD, PBGD, or CPPO gene, respectively, encoding the protein and PCR-amplified DNA fragments derived from or comprising another ENR-A, CBL, UROD, PBGD, or CPPO gene, respectively, are recombined in vitro and resulting variants with improved tolerance to the inhibitor are recovered as described above.

Example 22a

In vitro Recombination of CBL Genes by Staggered Extension Process

The Arabidopsis CBL gene and another CBL gene, or homologs thereof, or fragments thereof, are each cloned into the polylinker of a pBluescript vector. A PCR reaction is carried out essentially as described (Zhao et al. (1998) *Nature Biotechnology* 16: 258–261) using the "reverse primer" and the "M13-20 primer" (Stratagene Catalog). Amplified PCR fragments are digested with appropriate restriction enzymes and cloned into pTRC99a and mutated CBL genes are screened as described in Example 21.

Example 22b

In vitro Recombination of UROD Genes by Staggered Extension Process

The Arabidopsis UROD gene and another UROD gene, or homologs thereof, or fragments thereof, are each cloned into the polylinker of a pBluescript vector. A PCR reaction is carried out essentially as described (Zhao et al. (1998) *Nature Biotechnology* 16: 258–261) using the "reverse primer" and the "M13-20 primer" (Stratagene Catalog). Amplified PCR fragments are digested with appropriate restriction enzymes and cloned into pTRC99a and mutated UROD genes are screened as described in Example 21.

Example 22c

In vitro Recombination of PBGD Genes by Staggered Extension Process

The Arabidopsis PBGD gene and another PBGD gene, or homologs thereof, or fragments thereof, are each cloned into the polylinker of a pBluescript vector. A PCR reaction is carried out essentially as described (Zhao et al. (1998) *Nature Biotechnology* 16: 258–261) using the "reverse primer" and the "M13-20 primer" (Stratagene Catalog).

Amplified PCR fragments are digested with appropriate restriction enzymes and cloned into pTRC99a and mutated PBGD genes are screened as described in Example 21.

Example 22d

In vitro Recombination of CPPO Genes by Staggered Extension Process

The Arabidopsis CPPO gene and another CPPO gene, or homologs thereof, or fragments thereof, are each cloned into the polylinker of a pBluescript vector. A PCR reaction is carried out essentially as described (Zhao et al. (1998) *Nature Biotechnology* 16: 258–261) using the "reverse primer" and the "M13-20 primer" (Stratagene Catalog). Amplified PCR fragments are digested with appropriate restriction enzymes and cloned into pTRC99a and mutated CPPO genes are screened as described in Example 21.

Example 22e

In vitro Recombination of ENR-A Genes by Staggered Extension Process

The Arabidopsis ENR-A gene and another ENR-A gene, or homologs thereof, or fragments thereof, are each cloned into the polylinker of a pBluescript vector. A PCR reaction is carried out essentially as described (Zhao et al. (1998) *Nature Biotechnology* 16: 258–261) using the "reverse primer" and the "M13-20 primer" (Stratagene Catalog). Amplified PCR fragments are digested with appropriate restriction enzymes and cloned into pTRC99a and mutated ENR-A genes are screened as described in Example 21.

Example 23

In Vitro Binding Assays

Recombinant ENR-A, CBL, UROD, PBGD, or CPPO protein, respectively, is obtained, for example, according to Example 20. The protein is immobilized on chips appropriate for ligand binding assays using techniques which are well known in the art. The protein immobilized on the chip is exposed to sample compound in solution according to methods well know in the art. While the sample compound is in contact with the immobilized protein measurements capable of detecting protein-ligand interactions are conducted. Examples of such measurements are SELDI, biacore and FCS, described above. Compounds found to bind the protein are readily discovered in this fashion and are subjected to further characterization.

Various modifications of the invention described herein will become apparent to those skilled in the art. Such modifications are intended to fall within the scope of the appended claims.

Example 24

CBL Activity Assay

The CBL activity assay is derived from Stintjes et al. (1992) *Anal. Biochem.* 206, 334–343. The reaction volumes are preferably the ones described below, but can be varied depending on the experimental requirements. $0.01-1.0 \times 10^{-3}$ unit of an enzyme having CBL activity (one unit of activity is defined as the amount of enzyme required to produce 1 $\mu$mol/min of product) and 0.5–5 mM, but preferably 1 mM L(+)cystathionine (cyn) are mixed in a final volume of 10 $\mu$L 10 mM Tris-HCl (pH 7.0–9.0, but preferably 8.5) and 1–20 $\mu$M, but preferably 10 $\mu$M pyridoxal 5'-phosphate. The production of pyruvate is determined preferably according to Stintjes et al. (1992) *Anal. Biochem.* 206, 334–343 by adding 5 $\mu$L of 20mM o-phenylenediamine in 0.6 M hydrochloric acid. Fluorescence intensity is measured for the solution with an excitation wavelength of 410±10 nm and an emission wavelength of 535±10 nm. Alternatively, the absorbance of the solution may be measured with a wavelength of 410±10 nm.

Alternatively, pyruvate formation is quantified by a coupled reaction procedure. In this case, 0.5 units of lactate dehydrogenase and 0.2 mM NADH are added and the fluorescence intensity of the solution is measured with an excitation wavelength of 340±10 nm and an emission wavelength of 410±10 nm. Alternatively, the absorbance of the solution may be measured at 340 nm. Other ways to measure the activity of this enzyme known in the art may be used.

Example 25

In Vitro Functional Assay for PBGD Activity

Recombinant PBGD protein is obtained, for example, according to Example 5. The protein can be used in a functional PBGD activity assay as described in Jones and Leadbeater (1997) *Meth. Enz.* 281, 327–336. The reaction volumes are preferably the ones described below, but can be varied depending on the experimental requirements. $0.01-1.0 \times 10^{-3}$ unit of an enzyme having PBGD activity (one unit of activity is defined as the amount of enzyme required to produce 1 $\mu$mol/min of product) and 0.01–5 mM, but preferably 0.05 mM, porphobilinogen are mixed in a final volume of 10 $\mu$L 20 mM Tris-HCl (pH 7.0–9.0, but preferably 8.0) and 0.1–10 mM, but preferably 2 mM, dithiothreitol. The production of hydroxymethylbilane is determined indirectly preferably according to Jones and Leadbeater (1997) *Meth. Enz.* 281, 327–336 by adding 5 $\mu$L of 5 mM hydrochloric acid followed by 5 $\mu$L of 0.1% benzoquinone in methanol. Fluorescence intensity is measured for the solution with an excitation wavelength of 405±10 nm and an emission wavelength of 620±10 nm.

Example 26

In vitro Enzymatic Assay for CPPO Activity

Recombinant CPPO protein is obtained, for example, according to Example 6. The protein is used for in vitro enzymatic assays. At least three procedures are used by one skilled in the art. First, CPPO is combined with a protoporphyrinogen oxidase. In this procedure, coproporphyrinogen III is converted to protoporphyrinogen IX by CPPO and protoporphyrinogen IX is converted to protoporphyrin IX by protoporphyrinogen oxidase (Labbe, Camadro, and Chambon (1985) *Anal. Biochem.*, 149: 248–260). The formation of protoporphyrin IX is measured calorimetrically or fluorimetrically. Alternatively, CPPO is assayed singularly by converting protoporphyrinogen IX, the product of the CPPO enzymatic activity, to protoporphyrin IX chemically using an oxidizing agent known to one skilled in the art (Yoshinga (1997) *Meth. Enz.* 281: 355–367). The formation of protoporphyrin IX can be measured colorimetrically or fluorimetrically. Additionally, the formation of protoporphyrinogen IX from coproporphyrinogen III is measured by HPLC (Rossi, Garcia-Webb, and Costin (1989) *Clin. Chim. Acta* 181: 115–117).

Example 27

Plastid Transformation

Transformation Vectors

For expression of a nucleotide sequence encoding a polypeptide having ENR-A, CBL, UROD, PBGD, or CPPO activity, respectively, encoding in plant plastids, plastid transformation vector pPH143 or pPH145 (WO 97/32011) is used; and this reference is incorporated herein by reference. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH 143 so that it replaces the aadH gene. In this case, transformants are selected for resistance to PROTOX inhibitors.

Plastid Transformation

Seeds of *Nicotiana tabacum* c.v. 'Xanthi nc' are germinated seven per plate in a 1" circular array on T agar medium and bombarded 12–14 days after sowing with 1 μm tungsten particles (M10, Biorad, Hercules, Calif.) coated with DNA from plasmids pPH143 and pPH145 essentially as described (Svab, Z. and Maliga, P. (1993) *Proc. Natl. Acad. Sci. USA* 90, 913–917). Bombarded seedlings are incubated on T medium for two days after which leaves are excised and placed abaxial side up in bright light (350–500 μmol photons/m$^2$/s) on plates of RMOP medium (Svab, Z., Hajdukiewicz, P. and Maliga, P. (1990) *Proc. Natl. Acad. Sci. USA* 87, 8526–8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). Homoplasmic shoots are rooted aseptically on spectinomycin-containing MS/IBA medium (McBride, K. E. et al. (1994) *Proc. Natl. Acad. Sci. USA* 91, 7301–7305) and transferred to the greenhouse.

Various modifications of the invention described herein will become apparent to those skilled in the art. Such modifications are intended to fall within the scope of the appended claims.

What is claimed is:

1. A method of identifying herbicidal compounds, comprising:
   a) combining a plant polypeptide having porphobilinogen deaminase activity and comprising an amino acid sequence at least 90% identical to SEQ ID NO:8 with a compound to be tested for the ability to bind to said polypeptide, under conditions conducive to binding;
   b) selecting a compound identified in step (a) that binds to said polypeptide;
   c) applying a compound selected in step (b) to a plant to test for herbicidal activity; and
   d) selecting a compound identified in step (c) that has herbicide activity.

2. The method according to claim 1, wherein said polypeptide comprises an amino acid sequence at least 95% identical to SEQ ID NO:8.

3. The method according to claim 1, wherein said polypeptide comprises an amino acid sequence at least 99% identical to SEQ ID NO:8.

4. The method according to claim 1, wherein said polypeptide comprises SEQ ID NO:8.

5. A method of identifying herbicidal compounds, comprising:
   a) combining a plant polypeptide having porphobilinogen deaminase activity and comprising an amino acid sequence at least 90% identical to SEQ ID NO:8 with a compound to be tested for the ability to inhibit said polypeptide, under conditions conducive to inhibition;
   b) selecting a compound identified in step (a) that inhibits said polypeptide;
   c) applying a compound selected in step (b) to a plant to test for herbicidal activity; and
   d) selecting a compound identified in step (c) that has herbicidal activity.

6. The method according to claim 5, wherein said polypeptide comprises an amino acid sequence at least 95% identical to SEQ ID NO:8.

7. The method according to claim 5, wherein said polypeptide comprises an amino acid sequence at least 99% identical to SEQ ID NO:8.

8. The method according to claim 5, wherein said polypeptide comprises SEQ ID NO:8.

* * * * *